US012790617B2

(12) United States Patent
Kim et al.

(10) Patent No.: US 12,790,617 B2
(45) Date of Patent: Nov. 10, 2026

(54) RECOMBINANT VECTOR COMPRISING HYBRID SIGNAL SEQUENCE, AND SECRETORY PREPARATION METHOD OF HUMAN INSULIN-LIKE GROWTH FACTOR-1 USING THE SAME

(71) Applicant: INDUSTRY FOUNDATION OF CHONNAM NATIONAL UNIVERSITY, Gwangju (KR)

(72) Inventors: Geun-Joong Kim, Gwangju (KR); Dae-Eun Cheong, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 914 days.

(21) Appl. No.: 18/062,926

(22) Filed: Dec. 7, 2022

(65) Prior Publication Data

US 2023/0365978 A1 Nov. 16, 2023

(30) Foreign Application Priority Data

May 16, 2022 (KR) ........................ 10-2022-0059486

(51) Int. Cl.

| | |
|---|---|
| ***C12N 15/62*** | (2006.01) |
| ***C07K 14/475*** | (2006.01) |
| ***C12N 15/80*** | (2006.01) |
| ***C12P 21/02*** | (2006.01) |

(52) U.S. Cl.

CPC ............ *C12N 15/62* (2013.01); *C07K 14/475* (2013.01); *C12N 15/80* (2013.01); *C12P 21/02* (2013.01); *C07K 2319/02* (2013.01)

(58) Field of Classification Search

CPC ...................................................... C12N 15/62

See application file for complete search history.

(56) References Cited

U.S. PATENT DOCUMENTS 5,521,086 A 5/1996 Scott et al.

FOREIGN PATENT DOCUMENTS

| | | |
|---|---|---|
| KR | 100755727 B1 | 9/2007 |
| KR | 20140146163 A | 12/2014 |

OTHER PUBLICATIONS

Munoz, G. et al., "Hydrophobin gene srh1, expressed during sporulation of the biocontrol agent Trichoderma harzianum," Current Genetics, vol. 32, No. 3, Sep. 1997, 6 pages.

Vai, M. et al., "Improved secretion of native human insulin-like growth factor 1 from gas1 mutant *Saccharomyces cerevisiae* cells," Applied and Environmental Microbiology, vol. 66, No. 12, Dec. 2000, 4 pages.

Korean Intellectual Property Office, Notice of Allowance Issued in Application No. 10-2022-0059486, Apr. 4, 2025, 18 pages.

*Primary Examiner* — Suzanne M Noakes
(74) *Attorney, Agent, or Firm* — McCoy Russell LLP

(57) ABSTRACT

Provided is a recombinant expression vector containing a hybrid signal sequence and a method for secretory production of a human insulin-like growth factor-1 using the same. A heterologous signal sequence that significantly improves secretory expression of the human insulin-like growth factor-1 (hIGF1) is introduced into *Komagataella phaffii*, which is a unicellular eukaryotic cell, used as a host, such that various types of available signal sequences may be secured, and significantly improved secretion productivity may be achieved.

9 Claims, 23 Drawing Sheets

Specification includes a Sequence Listing.

| signal sequence | C-score max[1] | Mean S-score[2] | Predicted signal sequence | |
|---|---|---|---|---|
| Cu | 0.639 | 0.878 | MQFSIATIALFLSSAMA | SEQ. ID NO. 47 |
| Cu(R) | 0.633 | 0.883 | MRQFSIATIALFLSSAMA | SEQ. ID NO. 48 |
| Mhp1 | 0.451 | 0.861 | MQFSTIIATIFVAATGAVA | SEQ. ID NO. 49 |
| Mhp(R)1 | 0.410 | 0.869 | MRQFSTIIATIFVAATGAVA | SEQ. ID NO. 50 |
| Hcf5 | 0.179 | 0.908 | MQFLVLALASLAAA | SEQ. ID NO. 51 |
| Hcf(R)5 | 0.331 | 0.906 | MRQFLVLALASLAAA | SEQ. ID NO. 52 |
| Srh1 | 0.452 | 0.898 | MQFSIVALFATGALA | SEQ. ID NO. 53 |
| Srh(R)1 | 0.556 | 0.899 | MRQFSIVALFATGALA | SEQ. ID NO. 54 |

[1]C-score max : The first N-terminal residue of the mature pepide
[2]S-core mean : The average probability all residue analyzed belong to a signal peptide ;

FIG. 4

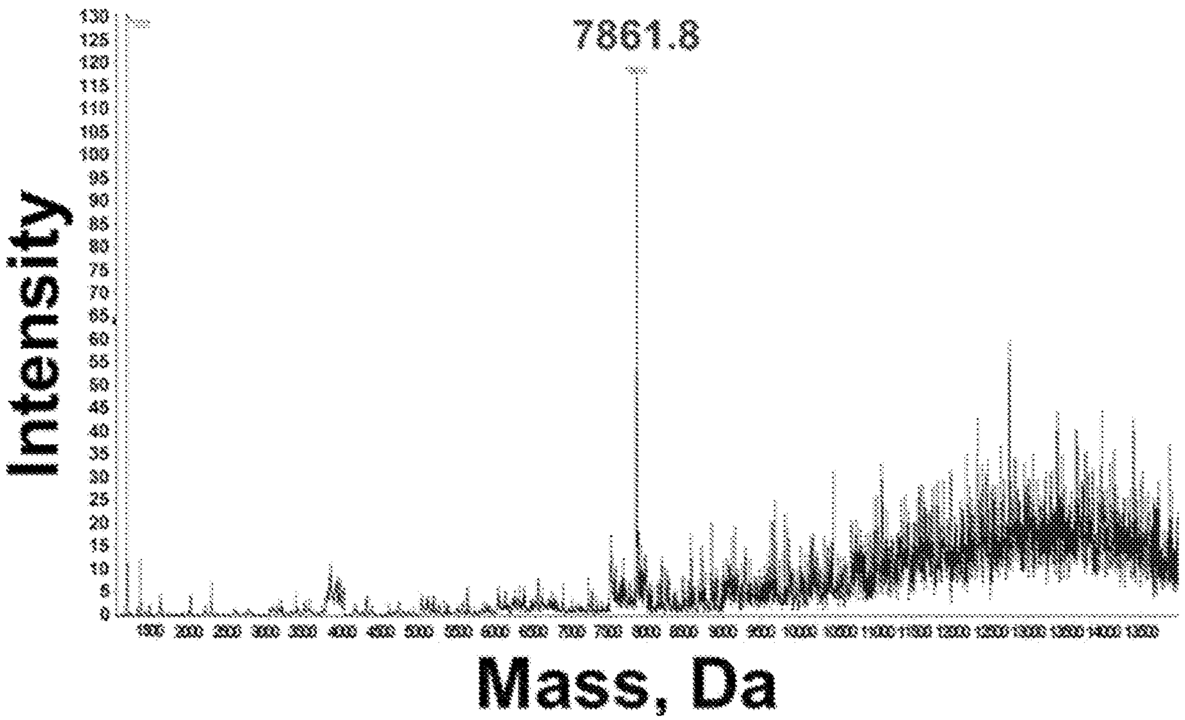

FIG. 18A

| Best sequence | Mw (mono.) | Mw (avg.) | 1DS bond | 2DS bond | 3DS bond |
|---|---|---|---|---|---|
| EAEAGRGPETLCGAELVDALQFVCGDRGFYFNKPTGYG SSSRRAPQTGIVDECCFRSCDLRRLEMYCAPLKPAKSA | 8262.92 | 8268.37 | 8266.37 | 8264.37 | 8262.37 |
| AEAGRGPETLCGAELVDALQFVCGDRGFYFNKPTGYGS SSRRAPQTGIVDECCFRSCDLRRLEMYCAPLKPAKSA | 8133.87 | 8139.26 | 8137.26 | 8135.26 | 8133.26 |
| EAGRGPETLCGAELVDALQFVCGDRGFYFNKPTGYGSS SRRAPQTGIVDECCFRSCDLRRLEMYCAPLKPAKSA | 8062.84 | 8068.18 | 8066.18 | 8064.18 | 8062.18 |
| AGRGPETLCGAELVDALQFVCGDRGFYFNKPTGYGSSS RRAPQTGIVDECCFRSCDLRRLEMYCAPLKPAKSA | 7933.79 | 7939.06 | 7937.06 | 7935.06 | 7933.06 |
| GRGPETLCGAELVDALQFVCGDRGFYFNKPTGYGSSSR RAPQTGIVDECCFRSCDLRRLEMYCAPLKPAKSA | 7862.76 | 7867.98 | 7865.98 | 7863.98 | 7861.98 |
| RGPETLCGAELVDALQFVCGDRGFYFNKPTGYGSSSRR APQTGIVDECCFRSCDLRRLEMYCAPLKPAKSA | 7805.73 | 7810.93 | 7808.93 | 7806.93 | 7804.93 |
| GPETLCGAELVDALQFVCGDRGFYFNKPTGYGSSSRRA PQTGIVDECCFRSCDLRRLEMYCAPLKPAKSA | 7649.63 | 7654.74 | 7652.74 | 7650.74 | 7648.74 |
| * DS bond : disulfide-bond (-2.0Da) | | | | | |

FIG. 18B

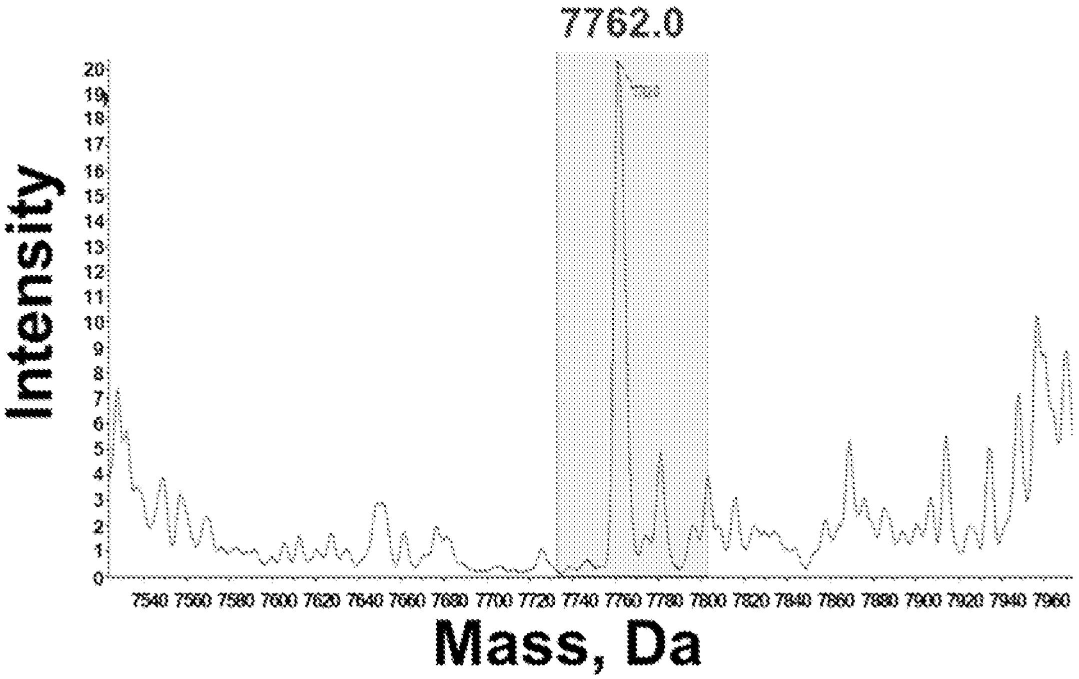

FIG. 19A

| Best sequence | Mw (mono.) | Mw (avg.) | 1DS bond | 2DS bond | 3DS bond |
|---|---|---|---|---|---|
| EAEANGFETLCGAELVDALQFVCGDRGFYFNKPTGYGS SSRRAPQTGIVDECCFRSCDLRRLEMYCAPLKPAKSA | 8163.84 | 8169.24 | 8167.24 | 8165.24 | 8163.24 |
| AEANGFETLCGAELVDALQFVCGDRGFYFNKPTGYGSS SRRAPQTGIVDECCFRSCDLRRLEMYCAPLKPAKSA | 8034.79 | 8040.12 | 8038.12 | 8036.12 | 8034.12 |
| EANGFETLCGAELVDALQFVCGDRGFYFNKPTGYGSSS RRAPQTGIVDECCFRSCDLRRLEMYCAPLKPAKSA | 7963.76 | 7969.04 | 7967.04 | 7965.04 | 7963.04 |
| ANGFETLCGAELVDALQFVCGDRGFYFNKPTGYGSSSR RAPQTGIVDECCFRSCDLRRLEMYCAPLKPAKSA | 7834.71 | 7839.93 | 7837.93 | 7835.93 | 7833.93 |
| NGFETLCGAELVDALQFVCGDRGFYFNKPTGYGSSSRR APQTGIVDECCFRSCDLRRLEMYCAPLKPAKSA | 7763.68 | 7768.85 | 7766.85 | 7764.85 | 7762.85 |
| GFETLCGAELVDALQFVCGDRGFYFNKPTGYGSSSRRA PQTGIVDECCFRSCDLRRLEMYCAPLKPAKSA | 7649.63 | 7654.74 | 7652.74 | 7650.74 | 7648.74 |
| FETLCGAELVDALQFVCGDRGFYFNKPTGYGSSSRRAP QTGIVDECCFRSCDLRRLEMYCAPLKPAKSA | 7592.61 | 7597.69 | 7595.69 | 7593.69 | 7591.69 |
| * DS bond : disulfide-bond (-2.0Da) | | | | | |

FIG. 19B

RECOMBINANT VECTOR COMPRISING HYBRID SIGNAL SEQUENCE, AND SECRETORY PREPARATION METHOD OF HUMAN INSULIN-LIKE GROWTH FACTOR-1 USING THE SAME

CROSS-REFERENCE TO RELATED APPLICATION

The present application claims priority to Korean Patent Application No. 10-2022-0059486, filed on May 16, 2022. The entire contents of the above-listed application are hereby incorporated by reference for all purposes.

SEQUENCE LISTING

The material in the accompanying sequence listing submitted electronically in XML format is hereby incorporated by reference in its entirety into this application. The accompanying file, named PLS22320_sequence_listing_ST26.XML was created on Nov. 30, 2022 and is 223 KB.

TECHNICAL FIELD

The following disclosure relates to a recombinant vector containing a hybrid signal sequence and a method for secretory production of a human insulin-like growth factor-1 (hIGF1) using the same, and more particularly, to a method of producing a hIGF1 that may implement improvement of secretory expression of hIGF1 by fusing, to the N-terminus of hIGF1, a hybrid signal sequence obtained by fusing a signal sequence of hydrophobin gene Srh1 of *Trichoderma harzianum* with a pro-sequence of an α-mating factor of yeast (*Saccharomyces cerevisiae*) and expressing hIGF1.

BACKGROUND

An insulin-like growth factor-1 (IGF1), also called somatomedin C, is mainly produced and secreted by the liver and also by most tissues without any specific restrictions. The IGF1 produced through stimulation of growth hormone secreted by the pituitary gland plays an important role in regulating cell proliferation, differentiation, and apoptosis through induction of tyrosine phosphorylation by stimulating IGF1 receptors on surfaces of various types of cells of muscle, bone, nerve, ovary, kidney, and the like through mechanisms such as endocrine, paracrine, and autocrine mechanisms.

Accordingly, the IGF1 has availability not only as a material for treating diseases such as growth deficiency, peripheral nerve regeneration, Type 1 diabetes, rheumatoid arthritis, and osteoporosis but also as a functional material for cosmetics, and thus, various attempts have been made for mass production thereof.

However, hIGF1 having a structure similar to that of insulin is a single-chain protein consisting of 70 amino acids and having a size of about 7 kDa and has three disulfide bonds. For these reasons, there is a problem in that it is difficult to express the IGF1 as an active form having a proper three-dimensional structure in *Escherichia coli* (*E. coli*), which is a prokaryotic host widely used for production of a useful recombinant protein. Recently, it has been reported that the above problem is alleviated by using *E. coli* Shuffle T7 as a host that has an improved disulfide bond-forming ability in the cytoplasm by fusing disulfide bond oxidoreductase (DsbA) to the amino terminus of IGF1 and inhibiting the activity of thioredoxin reductase (trxB) and glutathione reductase (gor) (Emamipour N, Vossouqhi M, Mahboudi F, Golkar M, Fard-Esfahani P, Applied Microbiology and Biotechnology, 103, 3393-3406 (2019)). In addition to such a disulfide bond-forming ability, when a medical protein such as an IGF1 is a target protein, the typical endotoxin of *E. coli*, which is a gram-negative bacterium, may be another problem.

A unicellular eukaryotic host such as yeast, for example, *Saccharomyces cerevisiae* or *Komagataella phaffii* (reclassified name for *Phichia pastoris*) is attracting attention as a host for producing various medical proteins because it has an endoplasmic reticulum, which is an organelle that may support proper disulfide bonds, is endotoxin-free, and generally recognized as a safe (GRAS) organism that may be relatively rapidly grown and cultured at a high concentration in a minimal medium. In these yeasts, foreign proteins are mainly produced by a secretory expression method in which a signal sequence is fused to an amino terminus of a target protein and secreted into the medium. The secretory expression efficiency varies greatly depending on the type of signal sequence and the target protein fused therewith, whereas the standard for compatibility between the protein and the signal sequence is not clearly established. Therefore, it may be important to discover various types of secretion signal sequences. In particular, in the case of hIGF1, it has been reported that only an α-mating factor among known signal sequences may be used to induce secretory expression (U.S. Patent Publication No. 5,521,086). Therefore, there is an urgent need to discover various signal sequences or develop a rational design method for secretory expression and production of a hIGF1.

RELATED ART DOCUMENTS

Patent Documents (Patent Document 1) Korean Patent Laid-Open Publication No. 2014-0146163

(Patent Document 2) U.S. Patent Publication No. 5,521,086

SUMMARY

An embodiment of the present invention is directed to providing a method of producing a hIGF1 that may implement significant improvement of secretory expression of the hIGF1 in *Komagataella phaffii* by producing a hybrid signal sequence synthesized by fusion of heterologous secretion signal sequences.

In one general aspect, there is provided a hybrid signal sequence consisting of an amino acid sequence for secretory expression of a hIGF11 (hIGF1) and obtained by fusing a pro-sequence of an α-mating factor to the C-terminus of a signal sequence of hydrophobin Srh1 containing one or two or more amino acid mutations.

The amino acid mutation may be obtained by inserting arginine into an amino acid at position 2 of the N-terminus of the signal sequence of the hydrophobin Srh1.

The hydrophobin Srh1 may be derived from *Trichoderma harzianum*, and the α-mating factor may be derived from yeast (*Saccharomyces cerevisiae*).

In another general aspect, there is provided a polynucleotide encoding the hybrid signal sequence.

The resulting polynucleotide encoding hybrid signal sequence may consist of a base sequence of SEQ ID NO: 5.

In still another general aspect, a recombinant expression vector contains the polynucleotide encoding hybrid signal sequence and a hIGF1.

The resulting polynucleotides may be repeated 2 to 10 times, thus present the corresponding copy in chromosome.

The recombinant expression vector may consist of a base sequence of SEQ ID NO: 6.

In still another general aspect, there is provided a non-human transformant transformed by introducing the recombinant expression vector into a chromosome.

The transformant may be *Komagataella phaffii.*

In still another general aspect, a method of producing a recombinant protein includes: preparing the recombinant expression vector; transforming the recombinant expression vector into a non-human transformable host to obtain a transformant; culturing the transformant to overexpress a hIGF1; and purifying and recovering an overexpressed recombinant protein.

In still another general aspect, there is provided a recombinant protein produced by the method of producing a recombinant protein.

The recombinant protein may be a recombinant protein from which a hybrid signal sequence is completely removed.

Other features and aspects will be apparent from the following detailed description, the drawings, and the claims.

BRIEF DESCRIPTION OF THE FIGURES

FIG. 4 depicts a prediction of a cleavage site and efficiency of each of the wild-type and arginine-inserted signal sequences of the four types of the hydrophobins using SignalP.

FIGS. 10A to 10C illustrate the vector map of pPinkHC_α-IGF1 for comparison of secretory expression levels of scvSrh(R)1-αpro, in which copy numbers of corresponding genes with the selected hybrid signal sequences are increased to 6, in which FIG. 10A is a map of a vector containing the hybrid signal sequence scvSrh(R)1-αpro of the present invention, and FIGS. 10B and 10C are maps of vectors containing the copy numbers of α-IGF1 with the signal sequence of the α-mating factor only are 1 and 6, respectively, as control groups.

FIGS. 18A and 18B are an LC-MS-MS analysis result of hIFG1 and a calculation result for confirmation of hIGF1, respectively, the hIGF1 being secreted by culturing *Komagataella phaffii* transformed with a vector in which a gene copy number of scvSrh(R)1-αpro-GR-hIGF1 is increased to 6 in a BMMY medium.

FIGS. 19A and 19B are an LC-MS-MS analysis result of hIGF1 and a calculation result for confirmation of hIGF1, respectively, the hIFG1 being secreted by culturing *Komagataella phaffii* transformed with a vector in which a gene copy number of scvSrh(R)1-αpro-N-hIGF1 is increased to 6 in a BMMY medium.

DETAILED DESCRIPTION

Figure 1A:
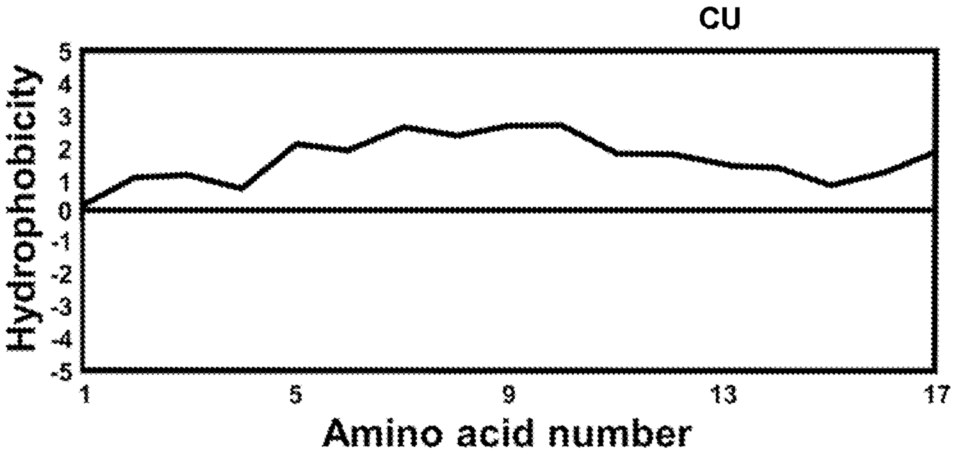
FIG. 1A-I are graphs depicting a change in hydropathy profile of each signal sequences of nine types of hydrophobins derived from fungi.
Figure 1B:
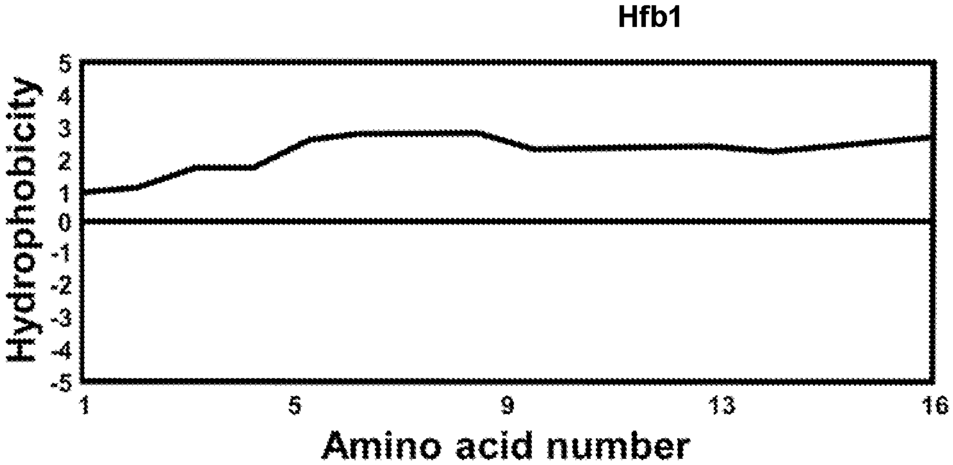
Figure 1C:
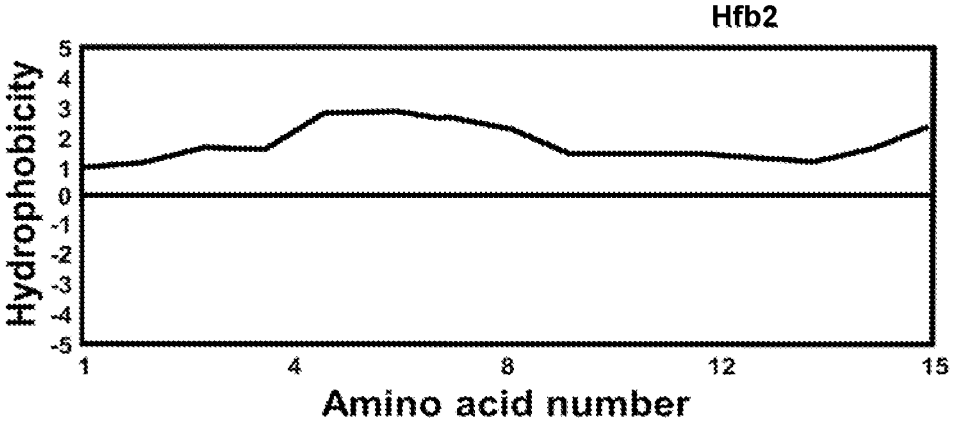
Figure 1D:
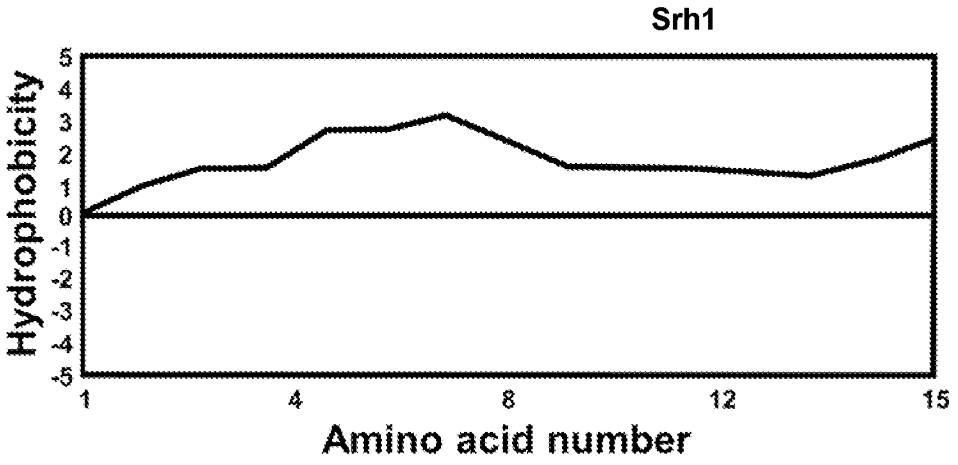
Figure 1E:
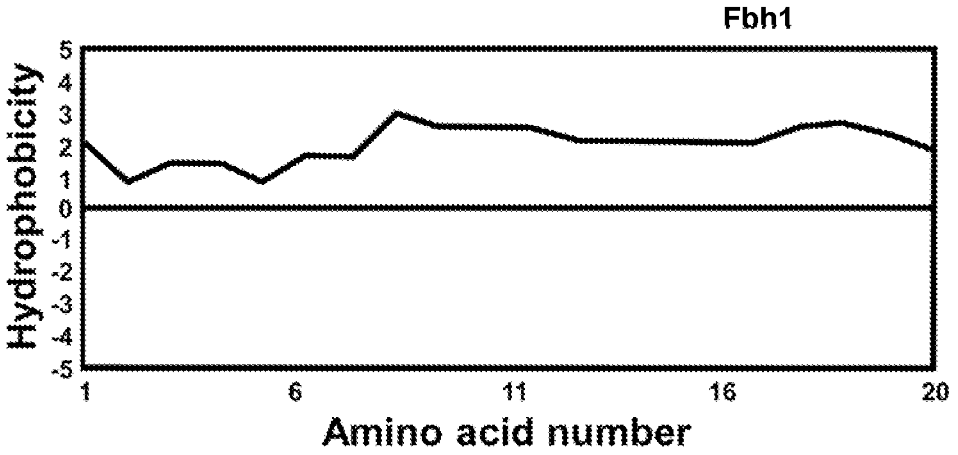
Figure 1F:
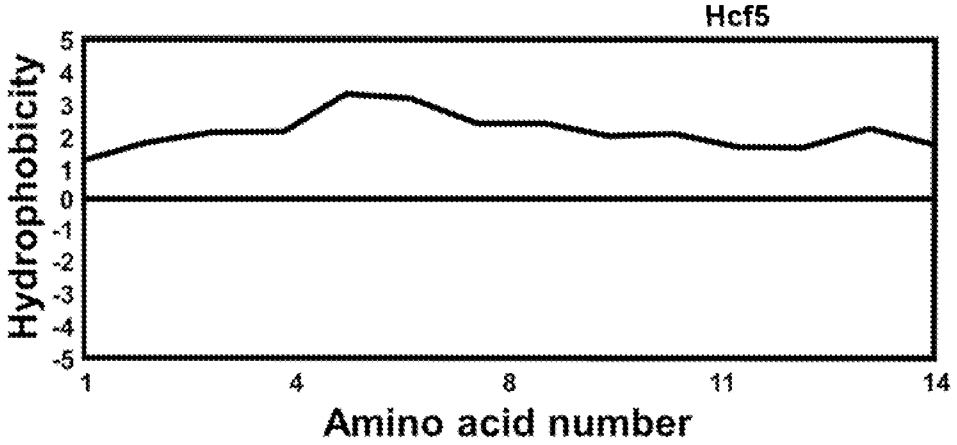
Figure 1G:
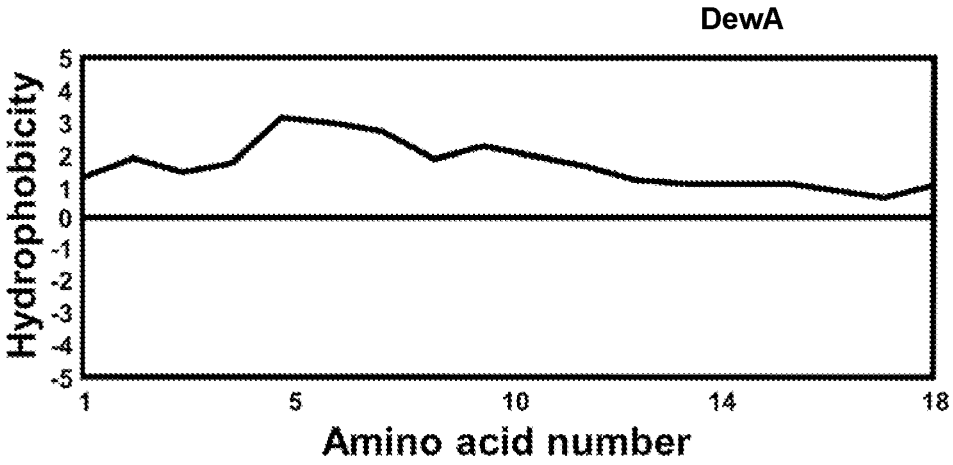
Figure 1H:
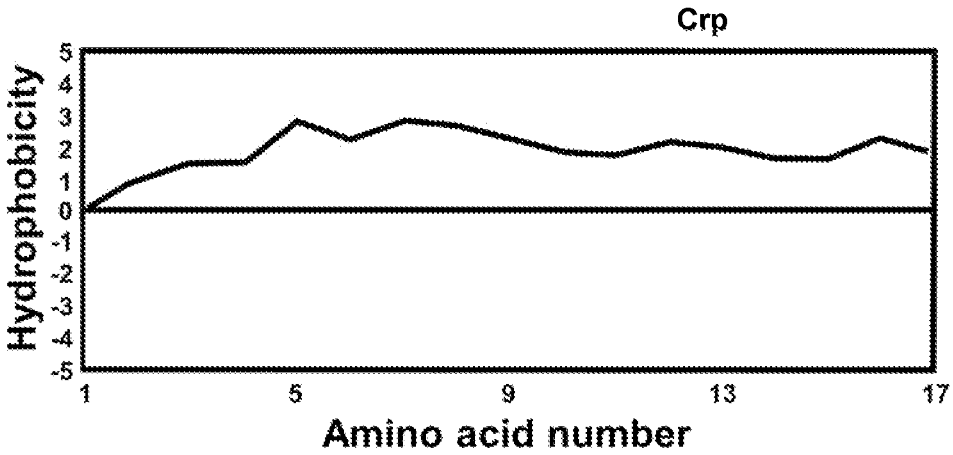
Figure 1I:
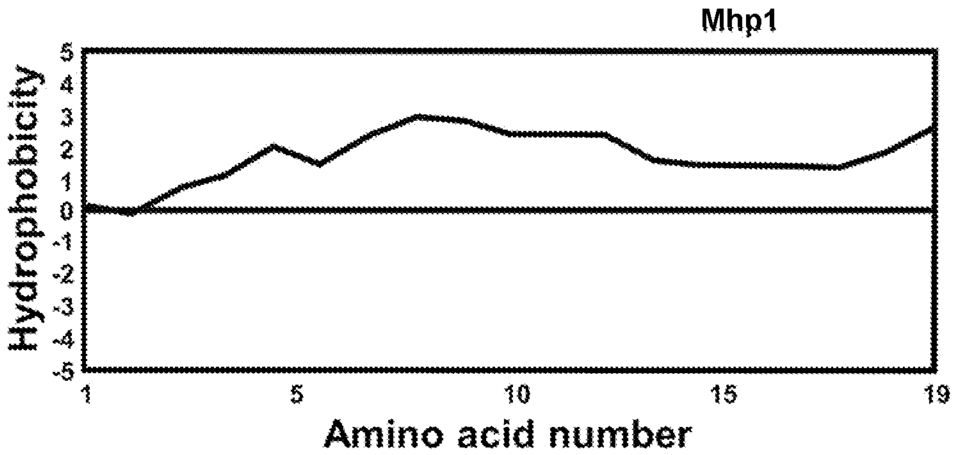

Hereinafter, a production method and use of a hIGF1 based on a hybrid signal sequence of the present invention will be described in detail with reference to the accompanying tables and drawings.

The drawings described herein are provided by way of example so that the spirit of the present invention can be sufficiently transferred to those skilled in the art. Therefore, the present invention is not limited to the drawings and may be implemented in other forms. In addition, the drawings will be exaggerated in order to provide the spirit of the present invention.

Terms "first", "second", and the like may be used to describe various elements, but the elements should not be limited by the terms. The terms are only used to distinguish one element from another element. For example, a first element may be named a second element and the second element may also be similarly named the first element without departing from the scope of the present invention.

Technical terms and scientific terms used herein have the general meanings understood by those skilled in the art to which the present invention pertains unless otherwise defined, and a description for the known function and configuration unnecessarily obscuring the gist of the present invention will be omitted in the following description and the accompanying drawings. Terms defined in commonly used dictionaries should be interpreted as having meanings that are consistent with their meanings in the context of the related art, and will not be interpreted as having ideal or excessively formal meanings unless otherwise clearly defined in the present specification.

In addition, unless the context clearly indicates otherwise, singular forms used in the specification of the present invention may be intended to include plural forms.

In addition, a unit used in the specification of the present invention without special mention is based on weight, and as an example, a unit of % or a ratio refers to wt % or a weight ratio.

In addition, the expression "comprise(s)" used in the specification of the present invention is intended to be an open-ended transitional phrase having an equivalent meaning as "include(s)", "contain(s)", "have (has)", or "is (are) characterized by" and does not exclude an element, a material, or a step that is not further listed. In addition, the expression "consist(s) essentially of" means that a specific element, material, or step that is not listed in combination with another element, material, or step may be present in an amount having no unacceptably significant influence on at least one basic and novel technical idea of the present invention. In addition, the expression "consist(s) of" means the presence of only the listed element, material, or step.

The terms "component", "composition", "composition of compound", "compound", "drug", "pharmacologically active agent", "active agent", "cure", "therapy", "treatment", and "medicine" are used interchangeably to refer to a compound or compounds or a composition of a substance that induces a desired pharmacological and/or physiologic effect by a local and/or systemic action when administered to a subject (human or animal).

The terms "treatment" and "therapy" (as well as different forms thereof) used in the specification of the present invention include preventative (for example, prophylactic), curative, or palliative treatments. The term "treating" used herein includes alleviating or reducing at least one adverse or negative effect or symptom of a condition, disease, or disorder.

The term "sample" or "specimen" used in the present invention refers to a subject for analysis, and is used in the same meaning throughout the specification.

The term "vector", "expression vector", or "recombinant expression vector" used in the specification of the present invention is a linear or circular DNA molecule that includes an element and an additional fragment provided for gene transcription and translation, and encodes a polynucleotide operably linked thereto. The additional fragment includes a promoter, a transcription termination sequence, and the like. The vector, the expression vector, or the recombinant expression vector includes one or more replication origins, one or more selection markers, and the like. The vector, the expression vector, or the recombinant expression vector is generally derived from a plasmid or viral DNA or contains both elements. The vector, the expression vector, or the recombinant expression vector may be linearized and recombined to be introduced into a chromosome of a host, if necessary.

The term "recombinant protein" used in the specification of the present invention refers to a common expression protein that expresses a gene derived from a cell of another species using a heterologous host and includes a protein in which another protein is linked to an amino or carboxyl terminus of a target protein sequence, or another amino acid sequence is added, if necessary.

An aspect of the present invention relates to a hybrid signal sequence consisting of an amino acid sequence for secretory expression of a hIGF1 and obtained by fusing a pro-sequence of an α-mating factor to the C-terminus of a signal sequence of hydrophobin Srh1 containing one or two or more amino acid mutations.

The hIGF1 has three pairs of disulfide bonds although it is a single-chain protein having a small size. The disulfide bond plays an important role in formation of a proper three-dimensional structure having a function and is one of the main causes of insoluble expression in *Escherichia coli* (*E. coli*), which is a prokaryotic organism having a reductive cytoplasm in which the proper formations of disulfide bonds are difficult, and the like. In addition to the disulfide bond-forming ability, when a medical protein such as an IGF1 is the target protein, endotoxin of *E. coli*, which is a gram-negative bacterium, may be another problem. Therefore, it is important for the hIGF1 to be designed to induce functional secretory expression as a recombinant protein in a eukaryotic cell that has an endoplasmic reticulum, which is an organelle that may form proper disulfide bonds and is classified as an endotoxin-free generally recognized as safe (GRAS) organism, instead of in a prokaryote cell.

Hydrophobin is a 10 to 15-kDa protein secreted by mycelial fungi, which are eukaryotic cells, and has four disulfide bonds. The exact pathway by which the hydrophobin is secreted by fungi is not well documented.

The amino acid mutation may mean, but is not limited to, substitution, addition, deletion, and the like of an amino acid. As a specific example of the present invention, the amino acid mutation may mean that arginine is inserted into an amino acid at position 2 of the N-terminus of the signal sequence of hydrophobin Srh1. The amino acid at position 2 of the N-terminus is known to affect the N-end rule that determines a localization, folding landscape, and interaction with chaperones (thus, protein fate) of a normally expressed protein.

The signal sequence of the hydrophobin Srh1 may be derived from, but is not limited to, different species. As a specific example of the present invention, the signal sequence of the hydrophobin Srh1 may be derived from *Trichoderma harzianum*. The signal sequence of the α-mating factor may also be derived from, but is not limited to, different species, which may be different from that of the hydrophobin. As a specific example of the present invention, the signal sequence of the α-mating factor may be derived from yeast (*Saccharomyces cerevisiae*).

Another aspect of the present invention relates to a polynucleotide encoding the hybrid signal sequence.

The polynucleotide is not particularly limited as long as it is a base sequence encoding the hybrid signal sequence. As an example, the polynucleotide may consist of a base sequence of SEQ ID NO: 5. In a process of producing the hybrid signal sequence, in order to improve transcriptional efficiency, the polynucleotide may introduce a kozak sequence and also randomly substitute a synonymous codon for a codon of the base sequence encoding about 10 or more amino acids at the N-terminus. For efficient transcription and translation of hIGF1, when a kozak sequence is designed, a process such as a rational design may be introduced so that a base that appears with a high frequency in a known kozak sequence may be located at a position other than the adenine (A) position that appears with the highest frequency, but the present invention is not limited thereto.

Still another aspect of the present invention relates to a recombinant expression vector containing the polynucleotide and a polynucleotide encoding a hIGF1. The recombinant expression vector may consist of, but is not limited to, a base sequence of SEQ ID NO: 6.

The recombinant expression vector may use a plasmid vector, a cosmid vector, a bacteriophage vector, a viral vector, or the like, as a template, but the present invention is not limited thereto. As a preferred example, the recombinant expression vector may optionally contain expression control elements such as a promoter, an operator, an initiation codon, a termination codon, a polyadenylation signal, and an enhancer, and may be prepared in various forms depending on a purpose.

In order to screen a transformant into which the recombinant expression vector is introduced, the recombinant expression vector may contain an antibiotic resistance marker, and the antibiotic resistance marker may be internal to the vector or may be externally introduced, but the present invention is not limited thereto.

The polynucleotides may be repeated 2 to 10 times in a host chromosome, but are not limited thereto. An expression level of the protein may be efficiently increased by increasing the copy number of the gene through the above process, which is preferable.

Still another aspect relates to a non-human transformant transformed with the recombinant expression vector.

The transformant may be used without limitation except for a human transformant as long as it may efficiently secrete and produce a recombinant protein. As a specific example of the present invention, *Komagataella phaffii*, which is a eukaryote, may be used, and a hIGF1 may be effectively secreted and produced using the transformant, which is preferable.

When the transformant is prepared, a transformation may be performed by a conventional method known in the art, and may be performed by, for example, a method of introducing a vector into a host by a natural introduction method, a thermal shock method, an electric shock method, or the like, and re-introducing the vector into a chromosome by homologous recombination, but the present invention is not limited thereto.

Still another aspect relates to a method of producing a recombinant protein, the method including: preparing the recombinant expression vector; transforming the recombinant expression vector into a non-human transformable host to obtain a transformant; culturing the transformant to overexpress a hIGF1; and purifying and recovering an overexpressed recombinant protein.

In culturing of the transformant, culture conditions are not particularly limited, and known culture conditions may be introduced and used. As a specific example, the culture may be performed at 28 to 32° C., preferably 29 to 31° C., and more preferably 30° C., and soluble expression of 90% or more of a target protein may be implemented in the above culture temperature range. A medium for culturing microorganisms may also be appropriately introduced from known media. As a specific example, a buffered methanol complex (BMMY) (100 mM potassium phosphate, pH 5.4, 1% yeast extract, 2% Bacto peptone, 1.34% YNB, and 400 μg/L biotin) medium may be used, but the present invention is not limited thereto.

The method of producing a recombinant protein may be performed by isolating and purifying a protein variant from a culture of the transformant. In this case, the culture may be a transformant or a culture medium thereof, and the culture medium may be a medium containing the transformant or a medium obtained by isolating the transformant.

Still another aspect relates to a recombinant protein produced by the method of producing a recombinant protein. The recombinant protein is not limited and may be an hIGF1 from which a hybrid signal sequence is completely removed through secretory expression and purification processes.

Hereinafter, the contents of the present invention will be described in more detail with reference to Examples. Examples are only for illustrating the present invention in more detail, and the scope of the present invention is not limited by Examples.

Strains, Reagents, Materials, and Experimental Protocols

In the present invention, reagents, materials, and protocols used for a polymerase chain reaction (PCR), DNA cloning, transformation, and the like are as follows, which will be apparent to those skilled in the art.

Other reagents were purchased from Sigma-Aldrich (USA) and the like.

Example 1 Selection of Signal Sequence for Secretory Expression of hIGF1

For secretory expression of a hIGF1, usability of each of signal sequences of nine types of hydrophobins derived from seven species was evaluated using SignalP.

The signal sequences of the hydrophobins are summarized in Table 1.

TABLE 1

| SEQ ID NO | Species | Gene | Amino acid sequence |
|---|---|---|---|
| 13 | *Ophiostoma novo-ulmi* | cu | MQFSIATIALFLSSAMA↓APYSGNSNSDSYDPCTG LLQKSPQCCNTDILGVANLDCHGPPSVPTSPSQF QASCVADGGRSARCCTLSLLGLALVCTDPVGI* |
| 14 | *Trichoderma reesei* | hfb1 | MKFFAIAALFAAAAVA↓QPLEDRSNGNGNVCPPG LFSNPQCCATQVLGLIGLDCKKVPSQNVYDGTD FRNVCAKTGAQPLCCVAPVAGQALLCQTAVGA* |

TABLE 1-continued

| SEQ ID NO | Species | Gene | Amino acid sequence |
|---|---|---|---|
| 15 | *Trichoderma reesei* | hfb2 | MQFFAVALFATSALA↓AVCPTGLFSNPLCCATNVL DLIGVDCKKTPTIAVDTGAIFQAHCASKGSKPLC CVAPVADQALLCQKAIGTF* |
| 16 | *Trichoderma viride* | srh1 | MQFSIVALFATGALA↓SVSVCPNGLYSNPRCCGA NVLGVAALDCHTPRVDVLTGPIFQAVCAAEGGQ PLCCVVPVAGQDLLCEEAQGTF* |
| 17 | *Pleurotus ostreatus* | fbh1 | MFSIRIATVVLAASALLAAA↓SPITNTETPVNQCG SGSIQCCESVQSASAAQAAGILGPLDILTNLQGLV ASHCSPLAAVGVSGTSCSSQTVCCKDVSKSGLVN LGCSPINLNL* |
| 18 | *Cladosporium fulvum* | hcf5 | MQFLVLALASLAAA↓APSIKLRAPSDVCPALDTP LCCQADVLGVLDLTCEAPSDDTSVSNFEAACAA TTGLTARCCTLPLLGEALLCTTP* |
| 19 | *Aspergillus nidulans* FGSC A4 | dewA | MRFIVSLLAFTAAATATA↓LPASAAKNKALATSA AFAKQAEGTCNVGSIACCNSPAETNNDSLLSGLL GAGLLNGLSGNTGSACAKASLIDQLGLLALVDH TEEGPVCKKNIVACCPEGTTNCVVAVDNAGAGT KAE* |
| 20 | *Endothia parasitica* | crp | MQFSIIAISFLASLAMA↓SPAKRGGGGGGSGSGS GSGSGSGSGGGSTTYTACSSTLYSEAQCCATDVL GVADLDCETVPETPTSASSFESICATSGRDAKCCT IPLLGQALLCQDPVGL* |
| 21 | *Magnaporthe grisea* | mhp1 | MQFSTIIATIFVAATGAVA↓LPAEVQERQVPYTPCS GLYGSAQCCATDILGLANLDCGQPSDAPVDADN FSEICAAIGQRARCCVLPILDQGILCNTPAGVTP* |

↓indicates the predicted signal sequence and cleavage site using SignalP.

The hydrophobicity of each of the signal sequences of the nine types of the hydrophobins shown in Table 1 were analyzed and compared with a signal sequence of yeast (*Saccharomyces cerevisiae*) Ost1 in which signal recognition particle (SRP)-dependent secretory expression was confirmed.

The results are illustrated in FIG. 1A-I.

Figure 2A:
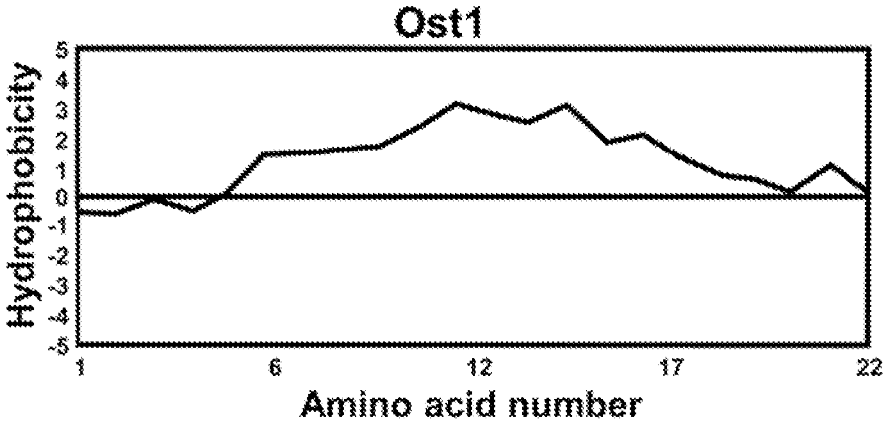
FIG. 2A-C are graphs depicting a change in hydropathy profile of each signal sequences known to have excellent secretory expression efficiency in yeast.
Figure 2B:
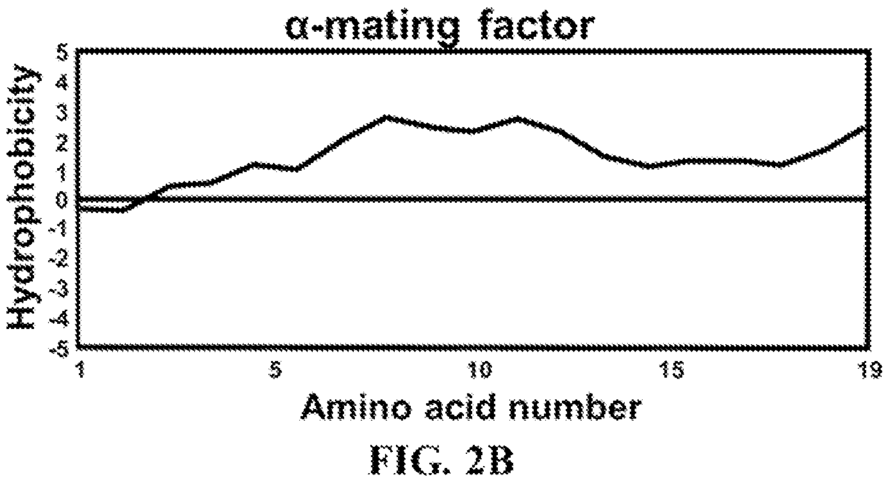
Figure 2C:
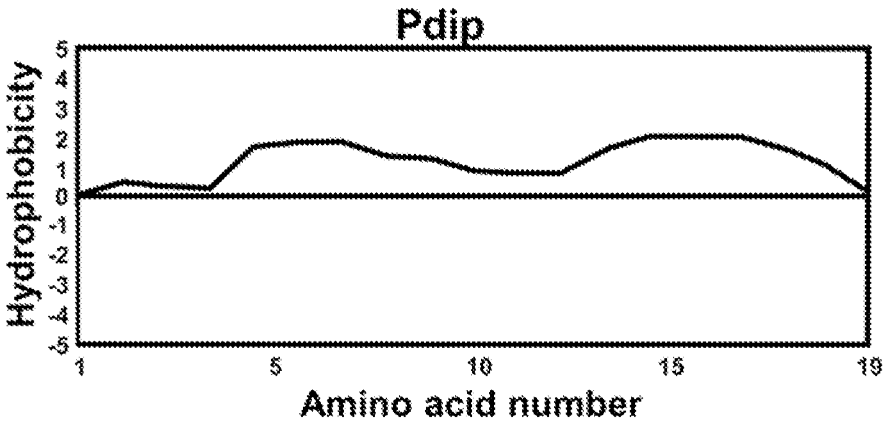
Figure 3A:
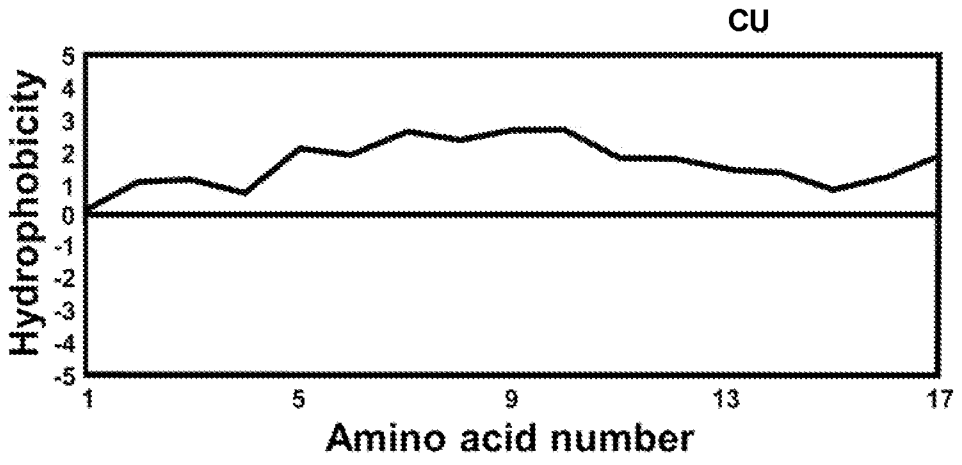
FIG. 3A-H are graphs depicting a change in hydropathy profile of each signal sequences of four types of hydrophobins selected from the analysis results of the change in hydropathy of FIGS. 1A, 1D, 1F, and 1I and 2A-C and a change in hydropathy of each signal sequences of the four types of hydrophobins changed by inserting arginine into the amino acid at position 2 for inducing the change in hydropathy.
Figure 3B:
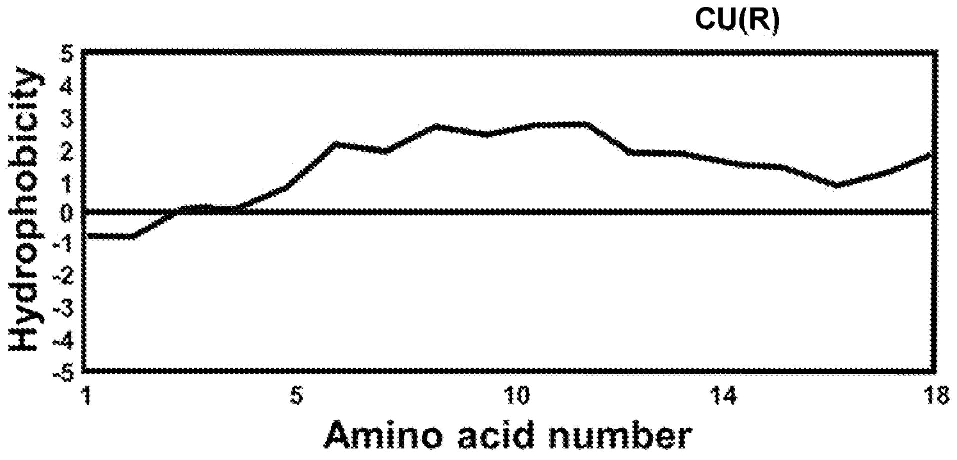
Figure 3C:
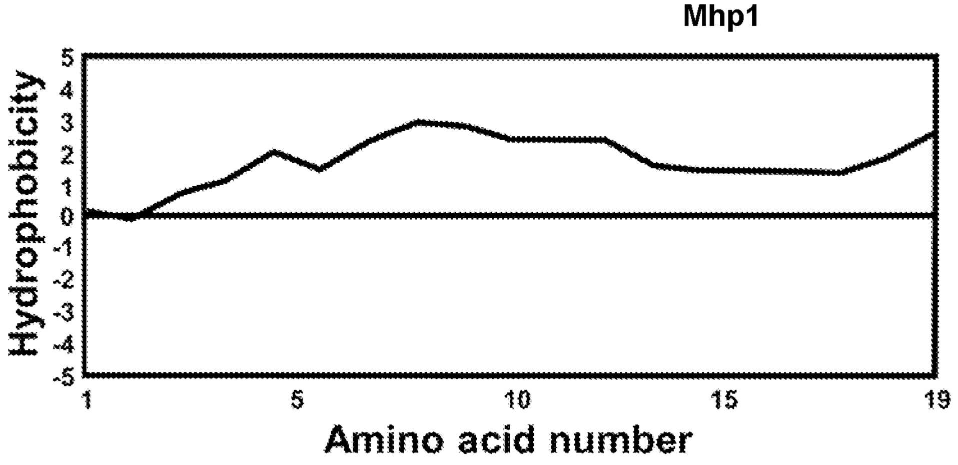
Figure 3D:
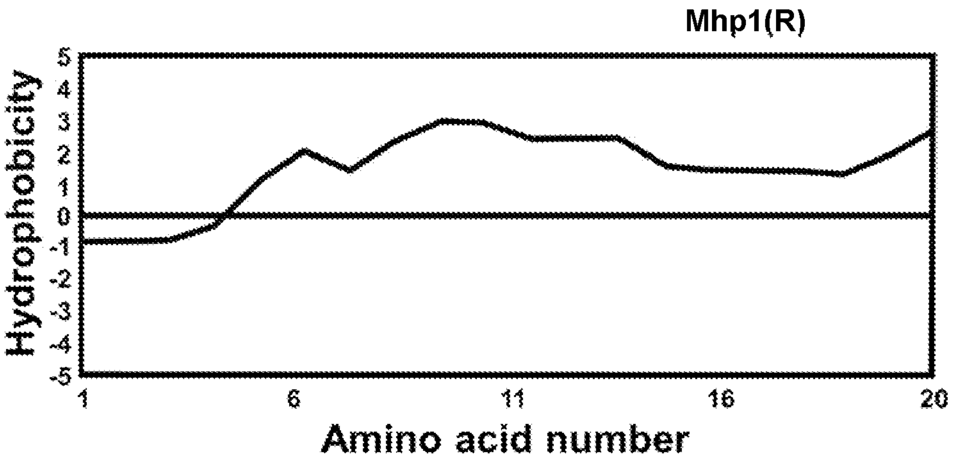
Figure 3E:
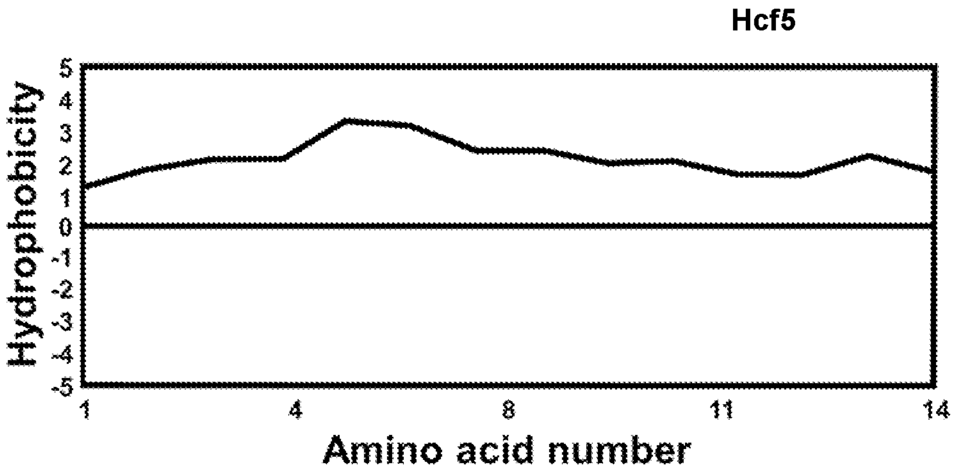
Figure 3F:
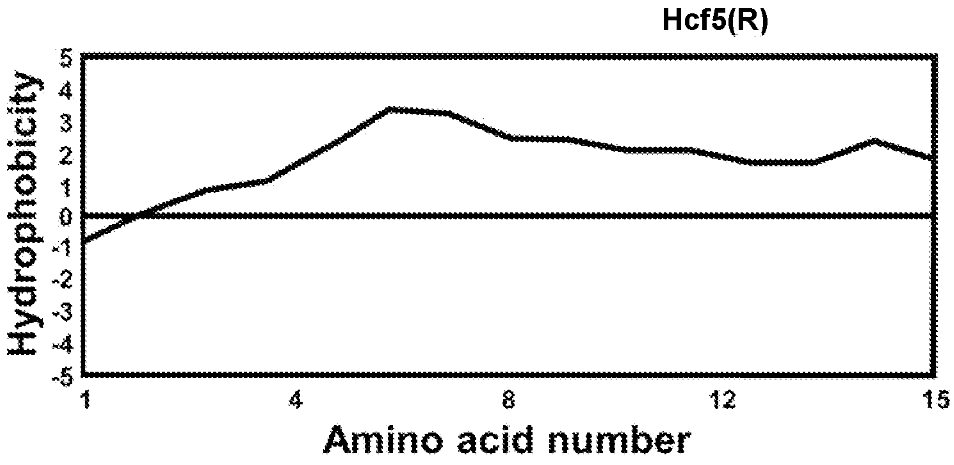
Figure 3G:
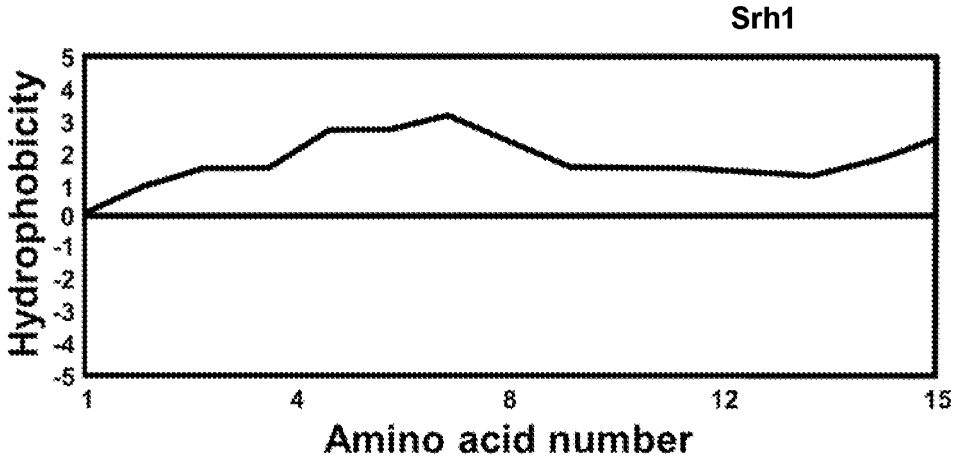
Figure 3H:
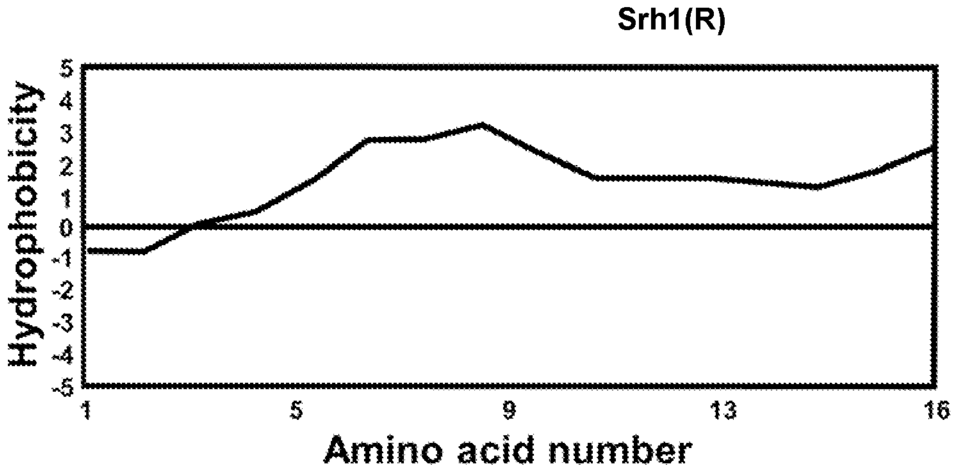
Figure 5A:
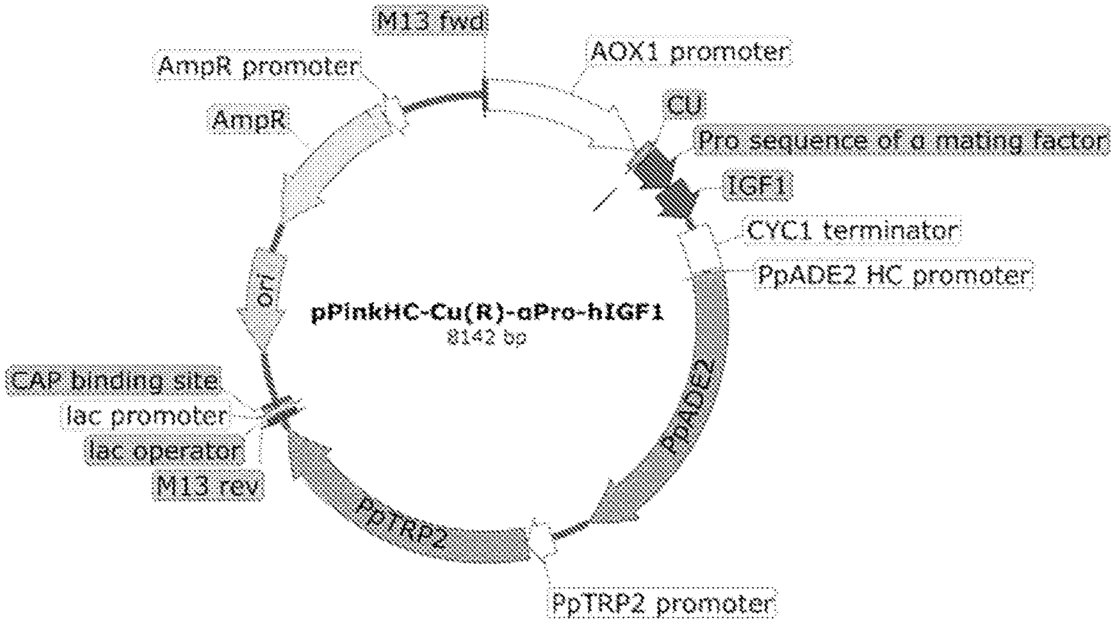
FIGS. 5A-D illustrate maps of four types of vectors having fused IGF1 constructs with modified hybrid signal sequences of four types of hydrophobins based on a rational design with pro-sequences of α-mating factors for secretory expression of hIGF1 (divided into two types in FIGS. 5A-5B and 5C-5D).
Figure 5B:
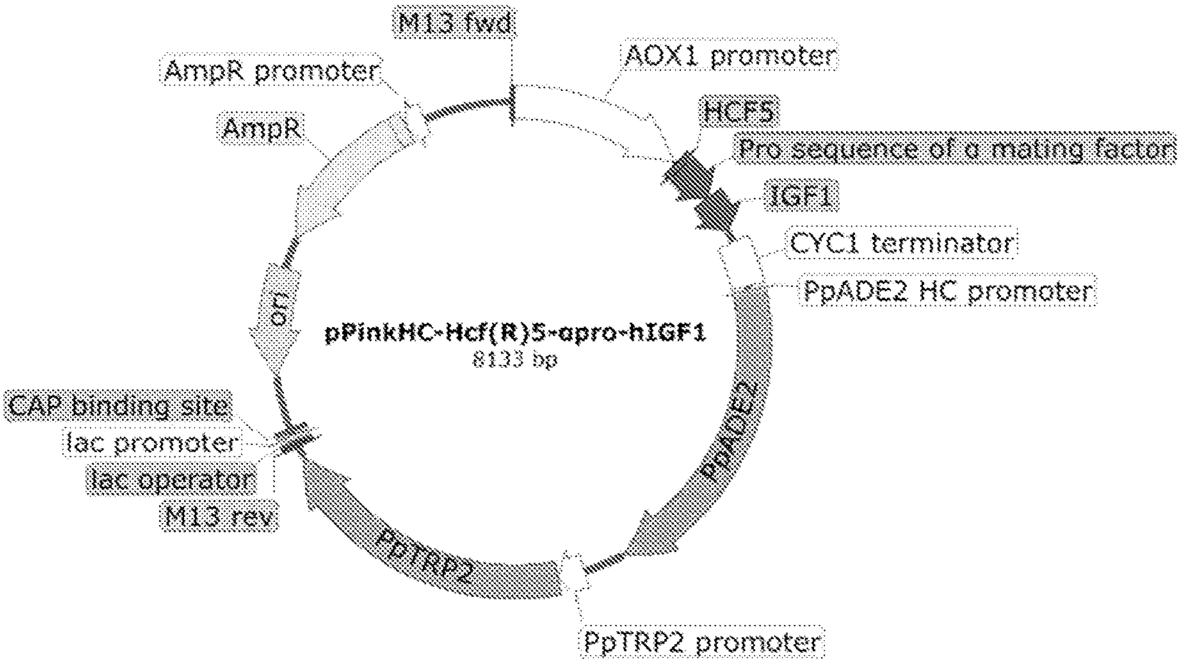
Figure 5C:
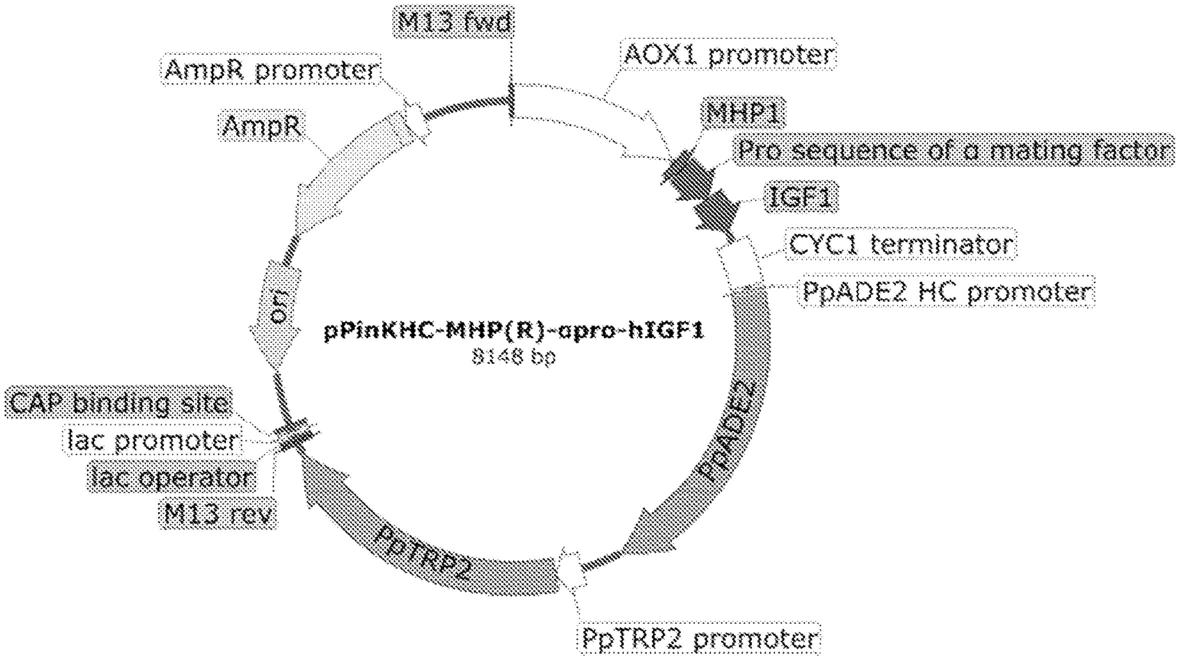
Figure 5D:
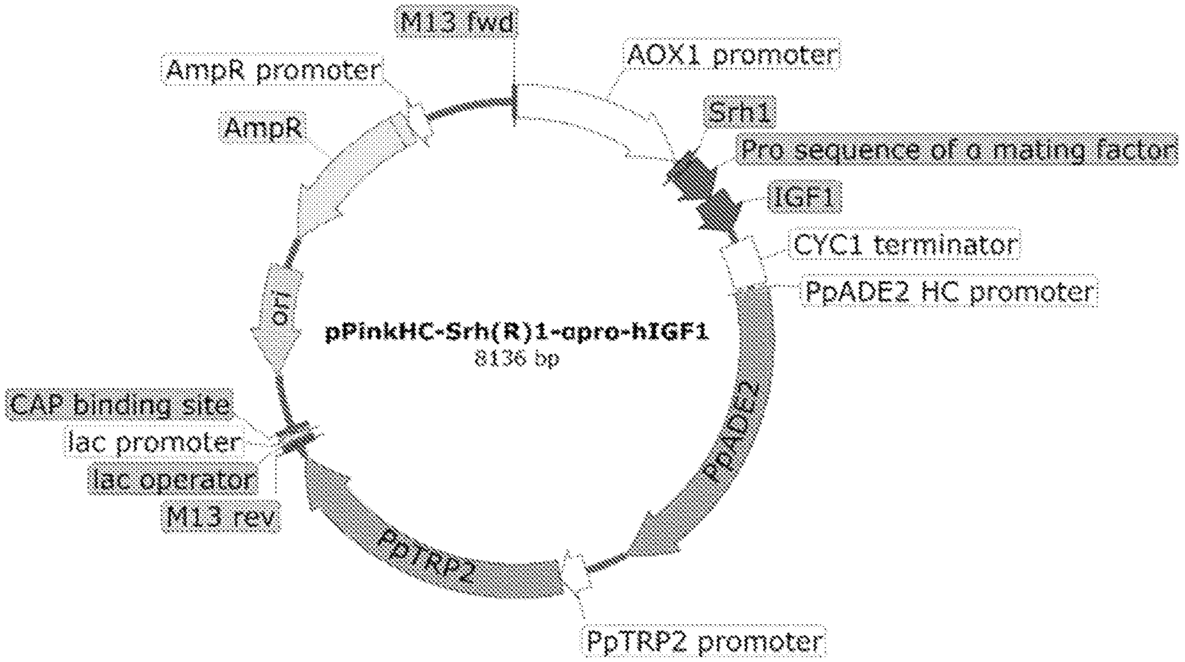

When the signal sequences of the SRP-dependent Ost1 and the α-mating factor were compared with the signal sequence of the SRP-independent Pdip, it was confirmed that both types of the signal sequences had a hydrophobic core, but the changes in hydropathy thereof were significantly different (also see FIG. 2).

Based on the assumption from this result that the factors determining the efficiency and SRP dependence of the signal sequence may be affected by the change in hydropathy, four types of CU, Hcf5, Mhp1, and Srh1 were selected as candidates and used in the following Examples, the CU and Hcf5 were predicted to be SRP-independent signal sequences due to a small change in hydropathy of the amino acid of the signal sequence, and the Mhp1 and Srh1 were predicted to be SRP-dependent signal sequences due to a large change in hydropathy.

Example 2 Modification of Signal Sequence of Hydrophobin Based on Rational Design Based on the report that the basic amino acid located at the N-terminus of the signal sequence is closely related to the post-translational translocation efficiency of exocrine proteins from the cytoplasm to the endoplasmic reticulum, a change in hydropathy of each of the signal sequences selected in Example 1 was analyzed again by inserting hydrophilic amino acid arginine (R) between amino acids at positions 2 and 3 of the N-terminus of the signal sequence of the hydrophobin having a relatively small change in hydropathy.

The results are illustrated in FIG. 3.

It was confirmed from this that the change in hydropathy of the signal sequence was increased by inserting the hydrophilic amino acid into the N-terminus, and it was also confirmed through SignalP analysis that the signal sequence was predicted in the same region even after the amino acid was inserted.

It was confirmed that, after the insertion of hydrophilic amino acid arginine, in the case of the signal sequence predicted to be SRP-dependent, the value indicating the probability of functioning as a signal sequence and the value predicting the probability of cleavage for exocytosis were increased in the results obtained using SignalP, whereas in the case of Cu and Mhp1 predicted to be SRP-independent, all of the above values were decreased.

Example 3 Design and Production of Hybrid Signal Sequence Obtained by Fusing Hydrophobin-Derived Signal Sequence Modified Through Re-Design with Pro-Sequence of α-Mating Factor 3.1 Design of Hybrid Signal Sequence In order to improve the extracellular secretion efficiency of the hIGF1, a hybrid signal sequence was designed by fusing a pro-sequence of an α-mating factor to the C-terminus of the signal sequence of the hydrophobin modified through redesign in Example 2.

In order to prepare a vector in which the hybrid signal sequence and the hIGF1 were cloned, a pair of primers and restriction enzymes shown in Table 2 were used.

TABLE 2

| SEQ ID NO | Name | Base sequence (5'→3') | Restriction enzyme |
|---|---|---|---|
| 22 | CU(R) F | ATAGAATTCATGCGNCAGTTCTCCATTGCCACC ATCGCCCTCTTCCTGTCCTCCGCCATGGC | EcoRI |
| 23 | CU(R)_α F | TTCCTGTCCTCCGCCATGGCGGCTCCAGTCAAC ACTACAACAG | — |
| 24 | α_IGF1 R | CACACAGGGTTTCCGGGCCAGCTTCAGCCTCTC TTTTCTC | — |
| 25 | α_IGF1 F | GAGAAAAGAGAGGCTGAAGCTGGCCCGGAAA CCCTGTGTGG | — |
| 26 | IGF1 R | ATAGCATGCTCACGCCGATTTCGCCGGTTTC | SphI |
| 27 | HCF(R)5 F | ATAGAATTCATGATGCGNCAATTCCTCGTCCTCG CCCTTGCATCGCTTGCAGCCGCAGCTCCAGTC | EcoRI |
| 28 | HCF5(R)_a F | CTTGCAGCCGCAGCTCCAGTCAACACTACAAC AG | — |
| 29 | MHP(R)1 F | ATAGAATTCATGCGNCAGTTCTCCACCATCATC GCCACCATCTTCGTCGCGGCCACCGGTG | EcoRI |
| 30 | MHP1(R)_α F | TTCGTCGCGGCCACCGGTGCCGTTGCCGCTCCA GTCAACACTACAACAG | — |
| 31 | Srh(R)1 F | ATAGAATTCATGCGNCAGTTCTCCATCGTTGCC CTCTTCGCTACTGGCGCTCTCGCCGCTCC | EcoRI |
| 32 | Srh1(R)1-α F | ACTGGCGCTCTCGCCGCTCCAGTCAACACTACA ACAG | — |
| 33 | SeqF | AGGAAGCTGCCCTGTCTTAAAC | — |
| 34 | SeqR | CAAATTAAAGCCTTCGAGCGTC | — |
| 35 | AOX1 F | GTTGAATGAAACCTTTTTGCCATC | |
| 36 | AOX1 R | TCATGAACGTTAGGCTATCAGC | |
| 37 | scvSrh1 | ATAGAATTC**WAMAM**ATGCGNCARTTYTCNATH GTNGCNCTN**TTYGC**NACTGGCGCTCTCGCCGCT CC | EcoRI |

*The bold underline text represents a kozak sequence, W is A or T, and M is A or C.

3.2 Construction of Hybrid Signal Sequence-Fused hIGF1

In order to generate the hybrid signal sequence designed by the above process, a polymerase chain reaction (PCR) was performed with pGAPzα (Invitrogen, ThermoFisher Scientific (Waltham, MA, USA)) as a template using a combination of CU(R)_α, HCF5(R)_α, MHP1(R)_α, and Srh1(R)1_α F forward primers and α_IGF1 R reverse primer, thereby obtaining a pro-sequence of an α-mating factor containing a portion of the C-terminal sequence of each signal sequence of hydrophobin.

Subsequently, a gene encoding IGF1 without the innate signal sequence from pET22a-IGF1 provided by the Korea Institute of Ocean Science and Technology (KIOST) was amplified using α_IGF1 F and α_IGF1 R, and a gene in which a portion of the C-terminal sequence of the signal sequence of the hydrophobin, the pro-sequence of the α-mating factor, and the hIGF1 were fused was obtained through overlapping PCR of the obtained two DNA fragments.

A polymerase chain reaction (PCR) was performed with partial δCU-αpro-IGF1, δHCF5-αpro-IGF1, δMHP1-αpro-IGF1, and δSrh1-αpro-IGF1 (here, δ means to contain only the C-terminus of each signal sequence of hydrophobin) obtained through the above process as templates using a combination of CU(R)_α, HCF5(R)_α, MHP1(R)_α, and Srh1(R)1_α F forward primers and IGF1 R reverse primer. Through this, a whole gene fragment in which a hybrid signal sequence obtained by fusing an intact signal sequence of hydrophobin with a pro-sequence of an α-mating factor (αpro) was fused with hIGF1.

Subsequently, the gene was cleaved with EcoRI and SphI restriction enzymes, ligation with pPinK-HC (Thermo Fisher Scientific (Waltham, MA, USA)) cleaved with the same enzymes was performed, and cloning was performed in *E. coli* XL1-Blue.

From the *E. coli* XL1-Blue, the four types of the prepared plasmids pPinkHC-CU(R)_αpro-hIGF1, pPinkHC-HCF(R)5_αpro-hIGF1, pPinkHC-MHP(R)1_αpro-hIGF1 and pPinkHC-Srh1(R)1_αpro-hIGF1 (see SEQ ID NOS: 1 to 4 and FIG. 5) were obtained and then linearized through cleavage with a restriction enzyme SpeI to induce homologous recombination into the chromosome of *Komagataella phaffii.*

Example 4 Secretory Expression of hIGF1 Using Hybrid Secretion Signal Sequence 4.1 Gene Copy Number Analysis and Hybrid Secretion Signal Sequence Selection Each of the plasmids linearized through the treatment with the restriction enzyme SpeI in 3.2 of Example 3 was introduced into the chromosome of *Komagataella phaffii* by electroporation, and the transformant was plated on a minimal dextrose (MD) medium (1.34% yeast nitrogen base (YNB) without amino acids, 2% dextrose, and 1.5% Bacto agar).

The cells were cultured at 30° C. for 3 to 5 days and the three colonies to reach a size of 1.5 to 2.0 mm first were selected, the selected colonies were plated on the same medium again, the cells were cultured a second time at 30° C. for 3 days, the grown colonies were inoculated into a BMG (100 mM potassium phosphate buffer, pH 5.4, 1.34% YNB, 2% glycerol) medium, and then, culture was performed at 30° C. and 240 rpm for 2 days.

Figure 6A:
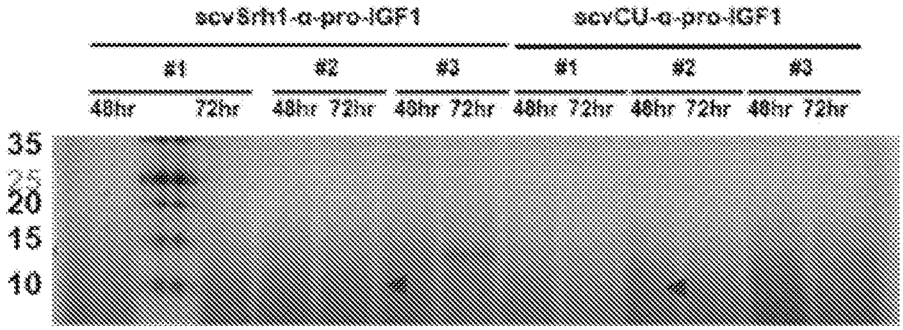
FIGS. 6A and B are SDS-PAGE results of analyzing the secretory expression of hIGF1 in *Komagataella phaffii* using the constructed hybrid signal sequence.
Figure 6B:
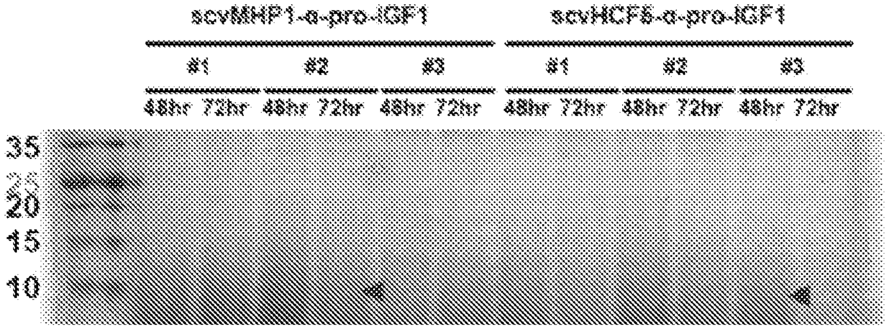

Thereafter, the cells cultured in the BMG medium were inoculated into a BMMY (100 mM potassium phosphate, pH 5.4, 1% yeast extract, 2% Bacto peptone, 1.34% YNB, 1% methanol) liquid medium so that an absorbance ($OD_{600}$) was 0.5, and the cells were cultured under the same conditions. The cells were cultured for 72 hours while adding 1% methanol at intervals of 24 hours, the supernatant was separated when 48 hours and 72 hours have elapsed, and the total protein present in the separated supernatant was concentrated 10 times by trichloroacetic acid (TCA) precipitation. The hIGF1 present in the prepared concentrate was subjected to 15% SDS-PAGE analysis (see FIGS. 6A and B).

In order to evaluate the difference in secretory expression of the hIGF1 by limitation to the difference in hybrid signal sequence, an expression level was normalized by the copy number of genes introduced into the chromosome of *Komagataella phaffii*. The genome of the recombinant *Komagataella phaffii* was extracted with a YeaStar Genomic DNA kit (Zymo Research (Irvine, CA)), and a real-time quantitative polymerase chain reaction (qPCR) was performed by repeating 40 cycles of a process performed at 98° C. for 2 minutes and a process performed at 98° C. for 30 seconds, 58° C. for 30 seconds, and 72° C. for 30 seconds using a pair of CU(R)_α, HCF5(R)_α, MHP1(R)_α, and Srh1(R)1_α F forward and α_IGF1 R reverse primers using an AirMax real-time PCR system (Agilent). The genome of *Komagataella phaffii* having one AOX1 promoter into which no gene was introduced and a pair of AOX1 F (SEQ ID NO: 31) and AOX1 R (SEQ ID NO: 32) primers were used as control groups. The qPCR results were normalized using a gene encoding glyceraldehyde 3 phosphate dehydrogenase (GAPDH) commonly used as an internal standard, and the measured gene copy numbers were compared.

As a result, when the number of inserted genes and the results of SDS-PAGE and ELISA (IGF1 ELISA kit, Enzo Life Sciences, Inc. (Farmingdale, NY)) were comprehensively analyzed, it was confirmed that among the four hybrid signal sequences, Srh1(R)1_α(pro) and CU(R)_α(pro) were more useful for secretory production of the hIGF1 in comparison to the other two types.

4.2 Quantification of Secretory Protein Expression Using Hybrid Signal Sequence

The secretory expression of the hIGF1 by each of the two types of the selected hybrid signal sequences was reconfirmed using an ELISA kit. The results thereof are illustrated in FIG. 7.

Through the results of analyzing the copy number by the method in 4.1 of Example 4, it was confirmed that the reason for the difference in productivity in spite of the same hybrid signal sequence was due to the number of genes inserted into the chromosome of *Komagataella phaffii.*

Therefore, hybrid Srh1(R)1_αpro was finally selected as a signal sequence for secretory expression of the hIGF1.

Figure 7:
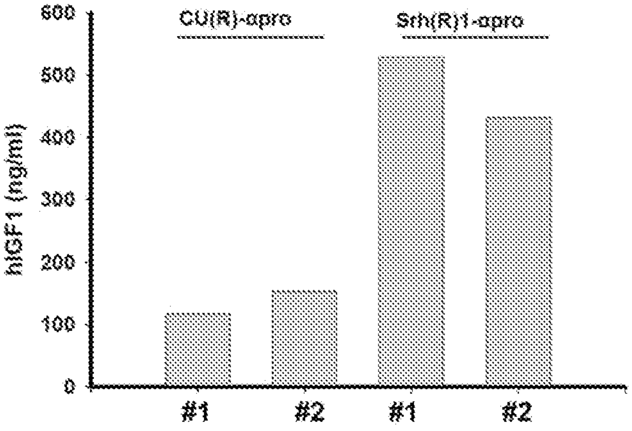
FIG. 7 is a result of quantifying the secretory expression of hIGF1 by ELISA using the selected two types of hybrid signal sequences CU(R)-αpro and Srh(R)1-αpro from the SDS-PAGE result among the produced hybrid signal sequences.

4.3 Preparation and Selection of Synonymous Codon-Substituted Library of Hybrid Secretion Signal Sequence It may be confirmed in FIG. 7 that when the selected Srh1(R)1_αpro was used as a signal sequence, the secretion productivity of the hIGF1 was about 500 μg/L, which was lower than expected. In order to increase the secretion productivity of the hIGF1, a DNA fragment (Srh1(R)1_αpro-hIGF1) in which 10 codons except for the initiation codon ATG were substituted with synonymous codons at the amino termini of the gene including the hybrid signal sequence of the pPinkHC-Srh1(R)1_αpro-hIGF1 produced in 3.2 of Example 3 as a template using primers scvSrh1 (SEQ ID NO: 37) and IGF1 R (SEQ ID NO: 26). The amplified DNA fragment was cleaved with EcoRI and SphI and ligated with pPinkHC cleaved with the same restriction enzymes, and then the recombinant vector was transformed into *E. coli* XL1-Blue. Thereafter, the transformant was plated on an LB solid medium containing 100 μg/ml of ampicillin to prepare an *E. coli* host-based synonymous codon library. When the plated *E. coli* was cultured at 37° C. to a colony size of about 0.5 mm, all colonies present in the solid medium were recovered to isolate plasmids. The obtained plasmids were linearized through cleavage with SpeI, and then the plasmid was transformed into *Komagataella phaffii* by electroporation. Thereafter, the transformant was suspended in 1 mL of YPDS (1% yeast extract, 2% Bacto peptone, 2% dextrose, 1 M sorbitol), cells were recovered by culture at 30° C. and 230 rpm for 2 to 4 hours, and the cells were plated on an MD medium, thereby preparing a *Komagataella phaffii*-based synonymous codon-substituted library.

The prepared library was cultured at 30° C. and the recombinant *Komagataella phaffii* was selected based on a colony phenotype without growth retardation. The results obtained by normalizing the secretory expression level of hIGF1 by the copy number through the processes 4.1 and 4.2 of Example 4 are illustrated in FIG. 8.

4.4 Final Selection of Hybrid Secretion Signal Sequence

Figure 8:
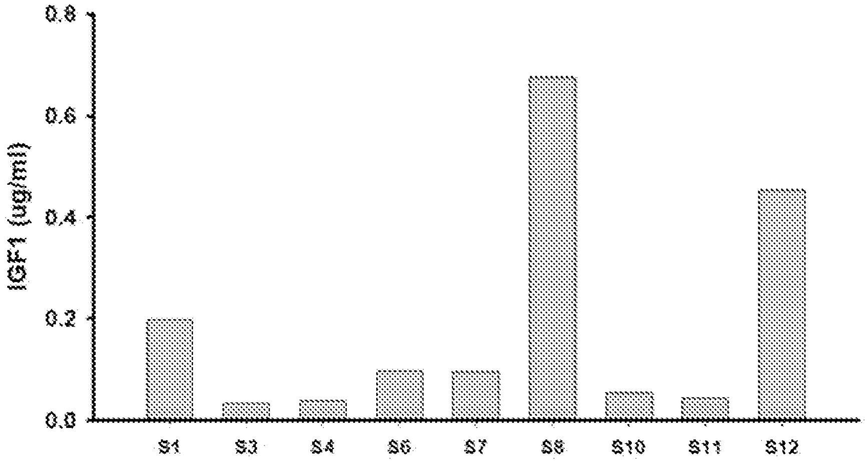
FIG. 8 is a result of quantifying the secreted expression of the screened hIGF1 mutants from synonymous codon-substituted libraries of the selected hybrid signal sequence Srh(R)1-αpro by ELISA.

From the chromosome of *Komagataella phaffii* into which the scvSrh1(R)1_αpro #8 hybrid signal sequence showing the highest productivity was inserted with reference to FIG. 8 illustrating the results of the secretory production of the hIGF1 of 4.3 of Example 4, a gene fragment containing scvSrh(R)1-αpro-hIGF1 was obtained using the pair of seqF and seqR primers shown in Table 2.

Figure 9:
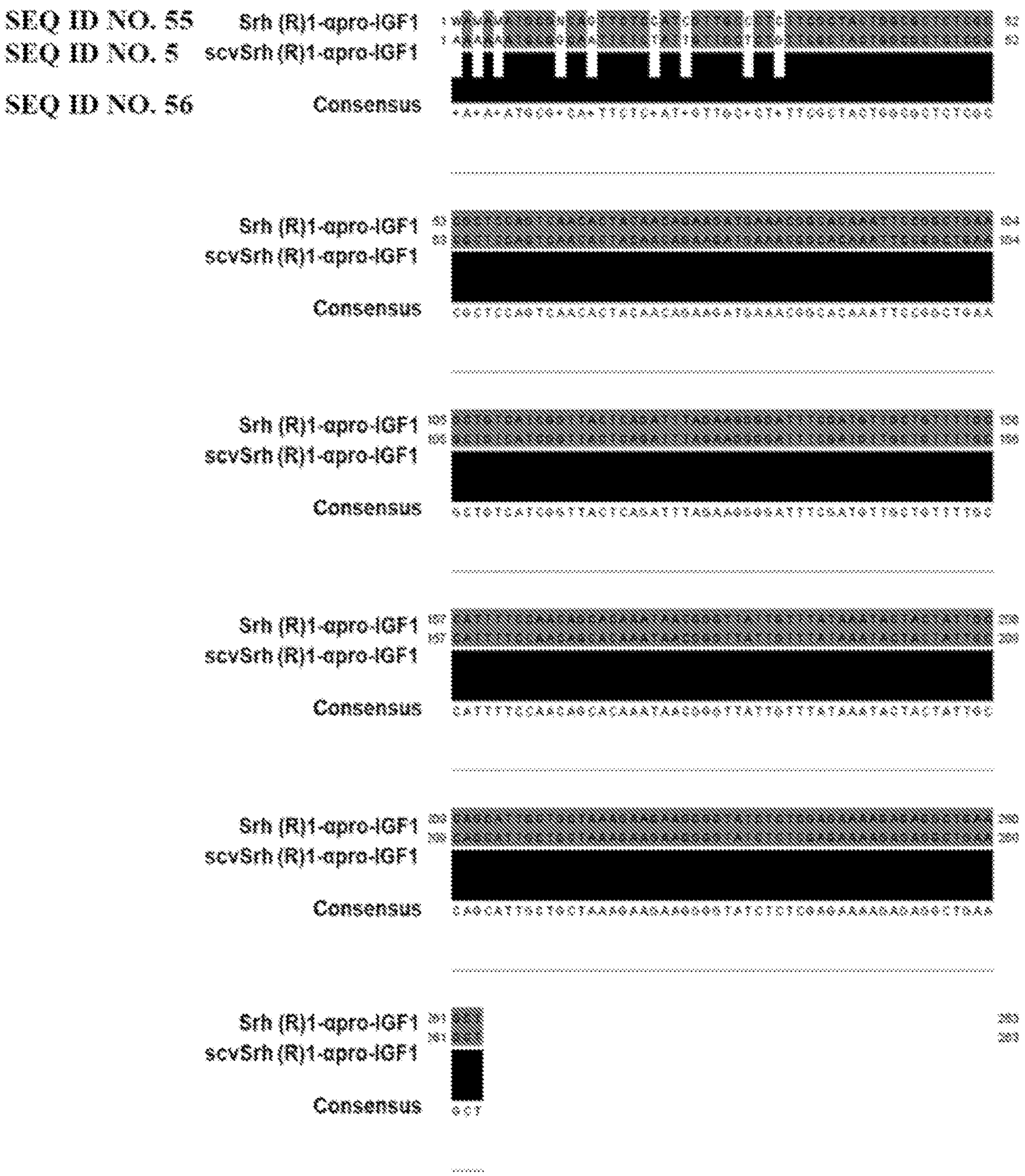
FIG. 9 is a result of aligning and comparing the base sequences of the wild-type Srh(R)1 and the screened synonymous codon substituent scvSrh(R)1.

From this, the base sequence of scvSrh(R)1-αpro was obtained through analysis of the base sequence by DNA sequencing (see SEQ ID NO: 5 and FIG. 9).

Hereinafter, an additional experiment was carried out using the resulting hybrid signal sequence.

Example 5 Preparation of Vector for Increasing Copy Number of hIGF1 Fused With Hybrid Signal Sequence or Signal Sequence of α-Mating Factor in Chromosome 5.1 Preparation of Vector for Increasing Copy Number of hIGF1 in Chromosome It was confirmed that the productivity of hIGF1 was increased by about 1.2 times through the synonymous codon substitution of the above Example. As in Example 4, in the case where the copy number of genes encoding a target protein was high in the chromosome of *Komagataella phaffii*, the effect of increasing the productivity of the foreign protein was confirmed.

Figure 10A:
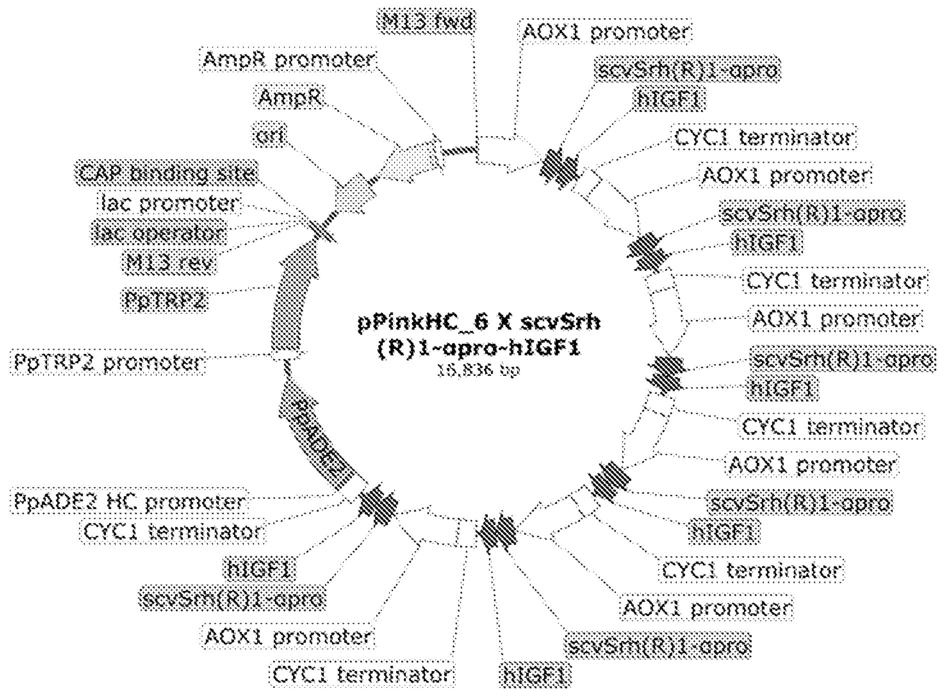

However, in a case where a single gene was introduced into a recombinant vector as in the above method, it was difficult to control the copy number of genes introduced into the chromosome to increase. Therefore, in order to solve this problem, a method of simultaneously introducing several genes into a chromosome by repeating cloning of the same gene into one recombinant vector was applied. That is, the scvSrh(R)1-αpro base sequence selected in Example 4 was repeatedly introduced several times to prepare a plasmid in which the scvSrh(R)1-αpro hybrid signal sequences along with hIGF1 were repeated 6 times (see SEQ ID NO: 6 and FIG. 10A).

Figure 10B:
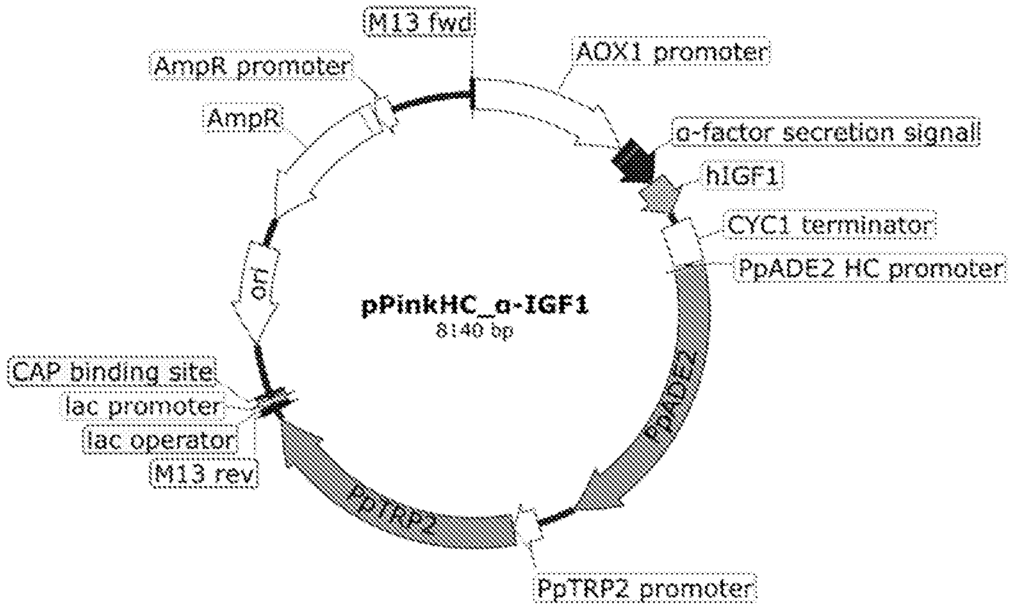
Figure 10C:
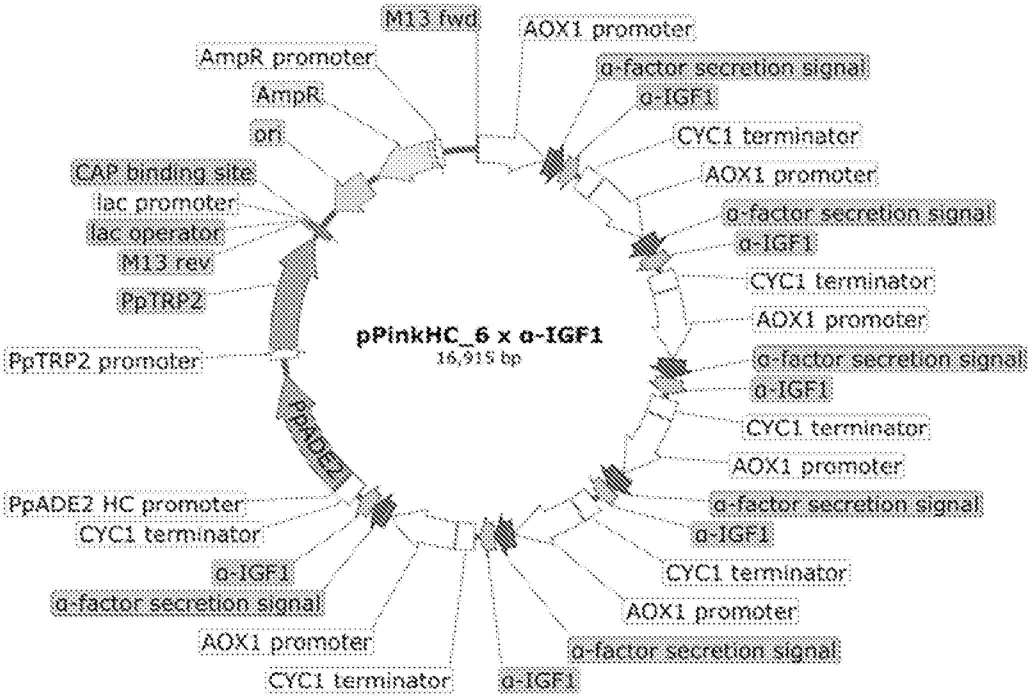

As a control group, an α-IGF1 (see SEQ ID NO: 7 and FIG. 10B) plasmid for the comparison of secretion efficiency with the signal sequence of the α-mating factor was prepared and used.

The pair of primers for preparing the plasmid are as shown in Table 3.

TABLE 3

| SEQ ID NO | Name | Base sequence (5'→3') | Restriction enzyme |
|---|---|---|---|
| 38 | In multi X F | CTTTAATTTGCAAGCTGGATCTAACATCCAAAGACGAAAGGTTG | |
| 39 | In multi X R | TTTGGAAGGCGGCCGCGGATC | |
| 40 | αF | TATTCGAAACGGAATTCATGAGATTTCCTTCAATTTTTACTGCAG | EcoRI |
| 41 | α_IGF1 R | CACACAGGGTTTCCGGGCCAGCTTCAGCCTCTCTTTTCTC | |
| 42 | α_IGF1 F | GAGAAAAGAGAGGCTGAAGCTGGCCCGGAAACCCTGTGTGG | |
| 43 | IGF1 R | ATAGCATGCTCACGCCGATTTCGCCGGTTTC | SphI |

The entire signal sequence of the α-mating factor for producing pPink-HC-α-hIGF1 was amplified through a polymerase chain reaction using the pGAPzα plasmid as a template and αF (SEQ ID NO: 40) and α_IGF1 R (SEQ ID NO: 41) as primers, and a hIGF1 containing a portion of the C-terminal sequence of the signal sequence of α-mating factor was amplified using α_IGF1 F (SEQ ID NO: 42) and IGF1 R(SEQ ID NO: 43).

The two genes were fused by overlapping PCR, and an α-hIGF1 gene fused with the signal sequence of the α-mating factor was obtained through PCR amplification using αF (SEQ ID NO: 40) and IGF1 R (SEQ ID NO: 43).

The obtained genes were treated with restriction enzymes EcoRI and SphI, and the treated genes were cloned into a pPinkHC vector treated with the same restriction enzymes, thereby producing pPinkHC_α-IGF1.

Thereafter, a polymerase chain reaction was performed with pPinkHC-scvSrh1(R)1-αpro-hIGF1 #8 and pPink-HC_α-hIGF1 as templates using In multi X F and In multi X R primers to amplifyan AOX promoter-scvSrh1(R)1-αpro-hIGF1/αIGF1-CYC terminator was amplified, and then ligated with pPink-HC-scvSrh1(R)1-αpro-hIGF1 and pPink-HC-α_IGF1 treated with a restriction enzyme BamHI, thereby preparing a vector in which the promoter-gene-end signal was repeated two times. The whole process was repeated to obtain each of pPink-HC-6XSrh(R)1-αpro-hIGF1 and pPinkHC-6Xα-IGF1 cloned with a total of six promoter-gene-end signals.

Example 6 Comparison of Secretory Expression of hIGF1 Fused With Hybrid Signal Sequence and Signal Sequence of α-Mating Factor 6.1 Secretory Expression Level of hIGF1 Fused With Hybrid Signal Sequence Each of the two types of the vectors pPinkHC-6XSrh(R)1-αpro-hIGF1 and pPinkHC-6Xα-IGF1 prepared in Example 5 was linearized through cleavage with a restriction enzyme SpeI, a transformation was induced by introducing each vector into *Komagataella phaffii* by electroporation, the transformant was suspended in a YPDS (1% yeast extract, 2% Bacto peptone, 2% glucose, 1 M sorbitol) medium, and culture was performed for 2 hours while mixing the cells at 28° C. and 240 rpm.

Thereafter, the cells were plated on a minimal dextrose (MD) (1.34% yeast nitrogen base (YNB) without amino acids, 2% dextrose, and 1.5% Bacto agar) medium, the cells were stationary-cultured at 30° C. for 2 to 5 days, colonies whose diameters reached 1.5 to 2.0 mm first were selected, and the selected colonies were plated on the same medium again.

Subsequently, additional stationary culture was performed at 30° C. for 3 days, the grown single colony was obtained and inoculated into a buffered minimal glycerol (BMG) (100 mM potassium phosphate buffer, pH 5.4, 1.34% YNB, and 400 μg/L biotin, 2% glycerol) medium, and then, culture was performed at 30° C. for a day while mixing the colonies at 240 rpm.

Thereafter, the culture cells were inoculated into a buffered minimal methanol (BMM) (100 mM potassium phosphate buffer, pH 5.4, 1% yeast extract, 2% Bacto peptone, 1.34% YNB, and 400 μg/L biotin, 1% methanol) liquid medium so that an absorbance ($OD_{600}$) was 0.5, and the cells were cultured in the same manner as that of Example 4.

Figure 11:
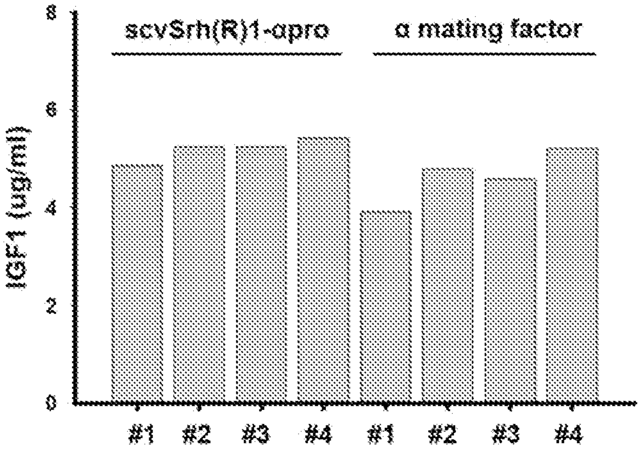
FIG. 11 is a result of quantifying an expression level of hIGF1 secreted by culturing *Komagataella phaffii* in a buffered minimal methanol (BMM) medium by ELISA.

After the culture for 3 days was completed, the human insulin-like growth factor-1 present in the medium was quantified by an ELISA kit. The results thereof are illustrated in FIG. 11.

It was confirmed from this that the measured secretory expression levels according to the two signal sequences were similar to each other, and in the case where the hybrid signal sequence scvSrh1(R)1-αpro was used, the reproducibility was remarkably excellent because the difference in productivity for each batch was insignificant in comparison to the case where the signal sequence of the α-mating factor was used.

6.2 Secretory Expression Level of hIGF1 Fused With Hybrid Signal Sequence According to Medium In order to confirm whether the difference in reproducibility as described above is also caused by a difference in the type of medium, the medium for secretory expression of hIGF1 was changed to a BMMY (100 mM potassium phosphate buffer, pH 5.4, 1% yeast extract, 2% Bacto peptone, 1.34% YNB, and 400 μg/L biotin, 1% methanol) liquid medium, and the secretion amount of hIGF1 was measured in the same manner as in 6.1 of Example 6.

Figure 12:
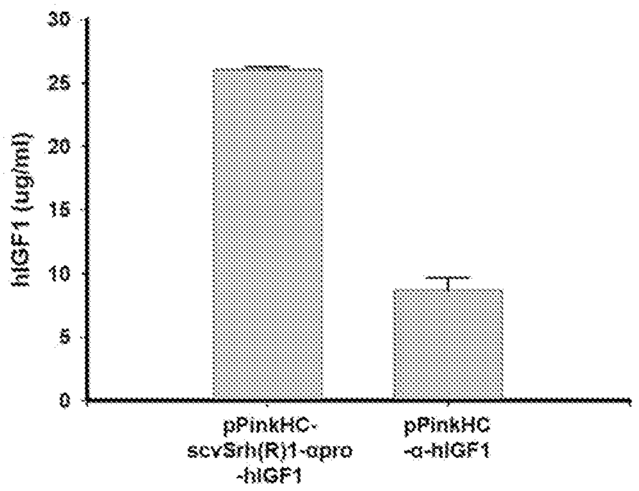
FIG. 12 is a result of quantifying an expression level of hIGF1 secreted by culturing *Komagataella phaffii* in a buffered methanol complex (BMMY) medium by ELISA.

As a result of measuring the secretion amount of hIGF1 in the medium by an ELISA kit after completion of the culture, it was confirmed that, similar to the BMM medium, in the case of the hybrid signal sequence scvSrh1(R)1-αpro, the reproducibility was significantly excellent and a concentration of 26.03 μg/mL of hIGF1 was exhibited, which showed that the production yield was about three times higher than that in the case where a concentration of hIGF1 was 8.68 μg/mL when the signal sequence of the α-mating factor as the control group was used (see FIG. 12).

Example 7 Purification and Verification of Secreted hIGF1

7.1 Purification of hIGF1

The pre-culture prepared in Example 6 was inoculated into a 3 L baffled flask containing 300 mL of a BMMY (100 mM potassium phosphate, pH 5.4, 1% yeast extract, 2% Bacto peptone, 1.34% YNB, and 400 μg/L biotin, 1% methanol) medium so that $OD_{600}$ was 0.5, culture was performed at 30° C. for 3 days under mixing at 220 rpm, and 1% methanol was added every 24 hours.

After completion of the culture, the culture medium was centrifuged at 4° C. and 6,000 rpm for 10 minutes to remove cells.

The culture medium removed by filtration of remaining cells with a filter having a pore size of 0.45 um was diluted 3-fold to a pH 4.0 with a 20 mM sodium acetate buffer. Thereafter, the diluted culture medium was loaded on a 5 mL Hitrap SP cation exchange column (GE Healthcare) equilibrated with the same buffer using fast protein liquid chromatography (FPLC), and washing was sufficiently performed with a 20 mM sodium acetate buffer (pH 4.0) to a level at which UV absorption at 280 nm was not observed.

Thereafter, hIGF1 was eluted (50 mL in total) by inducing a concentration gradient from 0 to 100% using a 20 mM sodium acetate buffer to which 1 M NaCl was added.

The eluted fractions were subjected to 15% SDS-PAGE and western blot analysis using anti-hIGF1 mouse IgG antibodies (R&D System) and goat anti-mouse IgG (Elabscience (Houston, TX, USA)).

Figure 13:
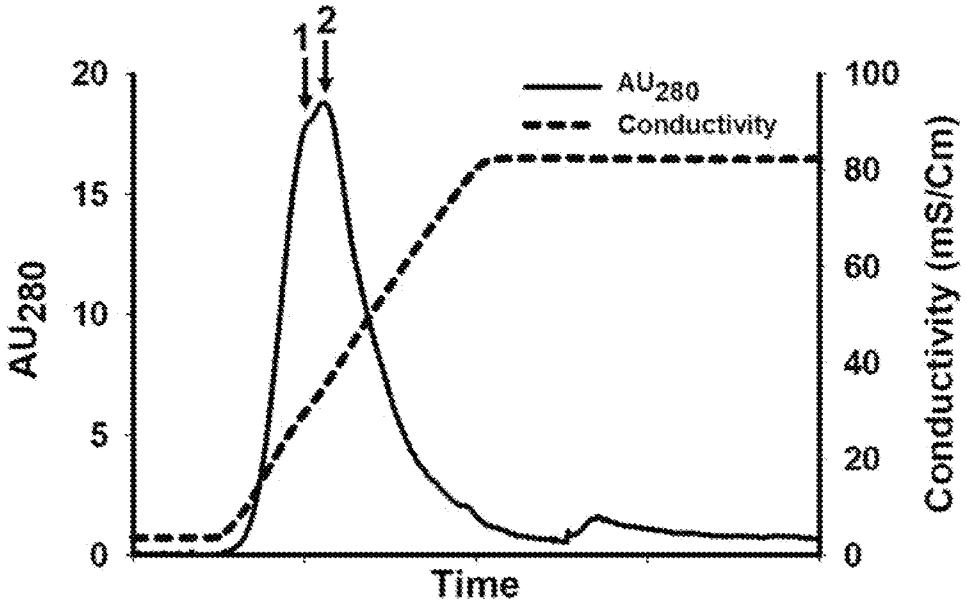
FIG. 13 is a result of an elution profile derived in a process of purifying hIGF1 secreted through culture in a BMMY medium using an ion exchange resin.
Figure 14A:
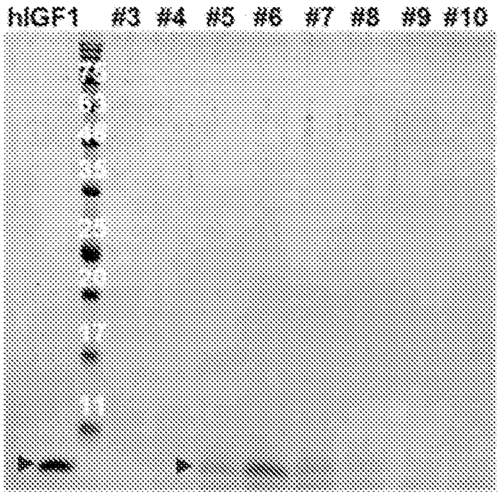
FIGS. 14A and B illustrate results of analyzing hIGF1 whose separation and purification are confirmed based on the elution profile by SDS-PAGE (14A) and western blot (14B), respectively.
Figure 14B:
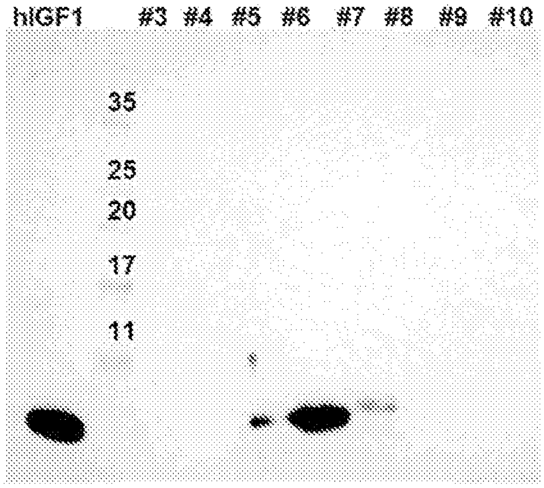

The results thereof are illustrated in FIGS. 13 and 14 A and B.

FIG. 13 illustrates UV absorption and conductivity during the elution process, and the peak marked with 1 in the chromatogram corresponds to a protein appeared in a position similar to hIGF1 (Procell) used as a positive control group in FIGS. 14A and B.

In the elution chromatogram, the peak 2 with a high absorbance was found adjacent to the fraction from which the hIGF1 was eluted, and it was presumed that a salt or pigment present in the medium was detected because there was no protein detected in SDS-PAGE.

It was confirmed from the results that the protein observed in SDS-PAGE through western blot was hIGF1. hIGF1 having a high purity of about 90% or more was purified by a single process using cation exchange chromatography, and 21 mg/L of hIGF1 (>80% recovery yield) was recovered from culture medium.

Example 8 Insertion of Protease Recognition Sequence for Complete Removal of Signal Sequence and Analysis of Amino Acid Sequence 8.1 Insertion of Protease Recognition Sequence In the case of a recombinant protein for pharmaceutical use, modification of the protein primary sequence (amino acid sequence) acts as an important variable for re-clinical consideration. In the case of the signal sequence of the α-mating factor, after cleavage of the signal sequence during extracellular secretion, four amino acids (EAEA) remaining at the N-terminal region of the protein are generally removed by STE13 (peptidyl-dipeptidase A) in human cells. On the other hand, the presence or absence of this scar of the recombinant protein differs depending on the type of protein fused with the signal sequence of the α-mating factor.

In order to completely remove the four residual amino acids that were likely to remain from the recombinant protein recovered through the above Example, asparagine (N) or glycine/arginine (GR), which was an amino acid that was cleavable by hydroxylamine or thrombin, was inserted between the hybrid signal sequence and hIGF1 by the following method, respectively.

Figure 15A:
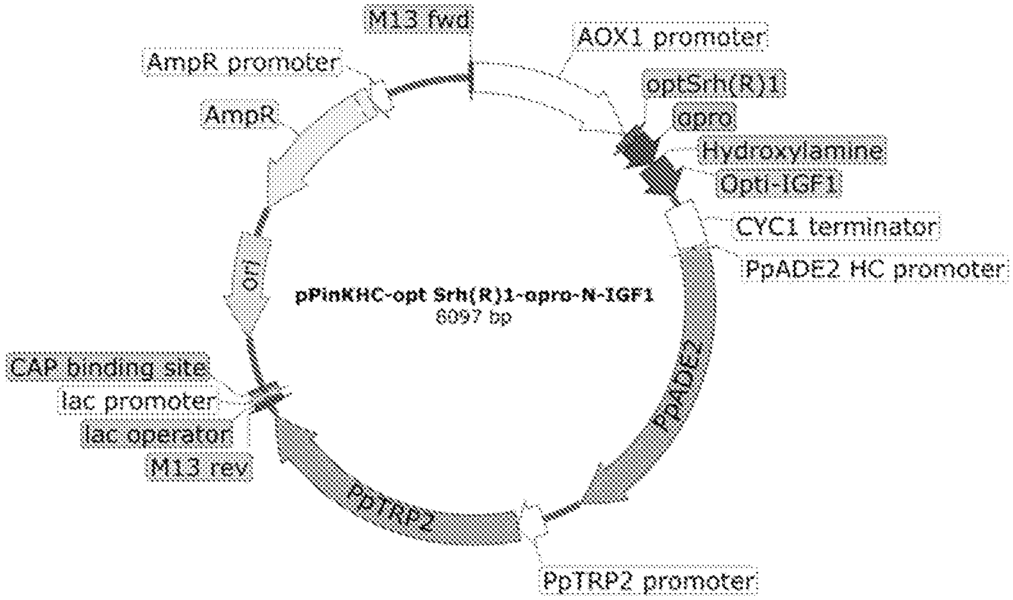
FIGS. 15A and 15B illustrate maps of vectors into which amino acid asparagine (N) and glycine-arginine (GR) are inserted, respectively, to cleave between the hybrid signal sequence and hIGF1 with hydroxylamine or thrombin.
Figure 15B:
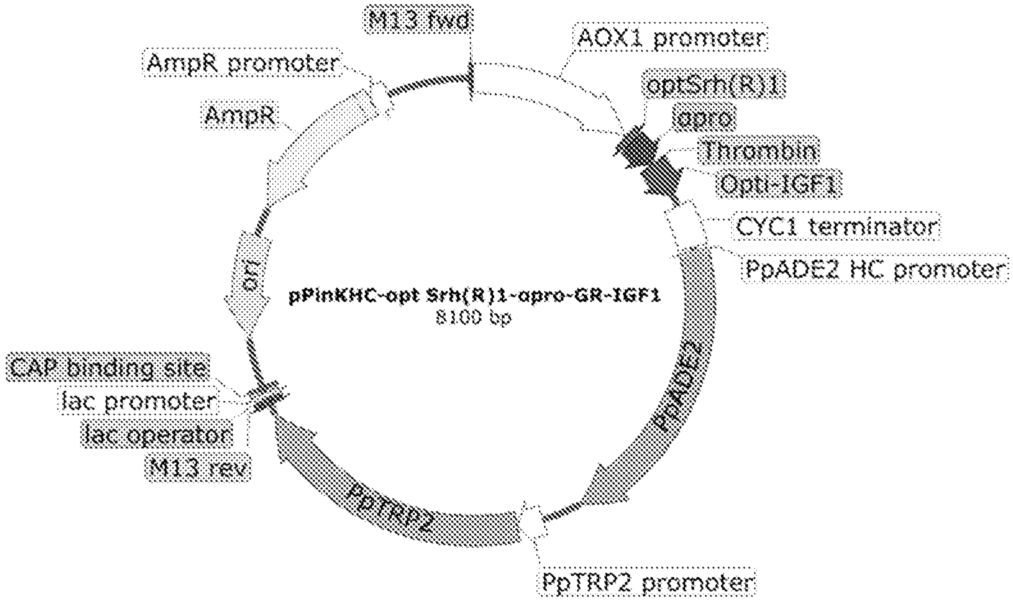

First, linear pPinkHC-scvSrh1(R)1_αpro-N-hIGF1 and pPinkHC-scvSrh1(R)1_αpro-GR-hIGF1 were amplified through a polymerase chain reaction using a set of primers, IGF GR/N 2F and IGF N 2R or IGF GR/N 2F and InIGF GR 2R, with pPinkHC-scvSrh1(R)1_αpro-hIGF1 as a template, and ligation independent cloning was performed, thereby obtaining recombinant plasmids (see FIGS. 15A and 15B).

TABLE 4

| SEQ ID NO | Name | Base sequence (5'→3') | Cleavage method |
|---|---|---|---|
| 44 | IGF GR/N 2F | GGCCCGGAAACCCTGTGTGG | |
| 45 | IGF N 2R | CAGGGTTTCCGGGCCGTTAGCTTCAG CCTCTCTTTTCTCG | Hydroxyl-amine |
| 46 | InIGF GR 2R | CAGGGTTTCCGGGCCCCGACCAGCTT CAGCCTCTCTTTTCTCG | Thrombin |

Figure 16A:
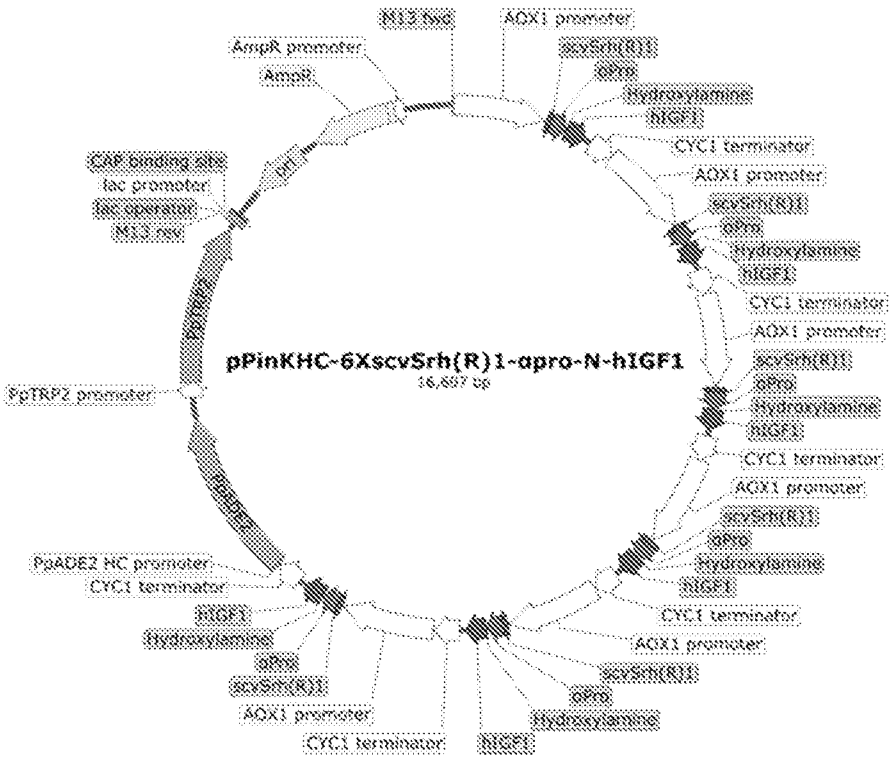
FIGS. 16A and 16B illustrate maps of vectors in which gene copy numbers of scvSrh(R)1-αpro-GR-hIGF1 and scvSrh(R)1-αpro-N-hIGF1 are increased to 6, respectively.
Figure 16B:
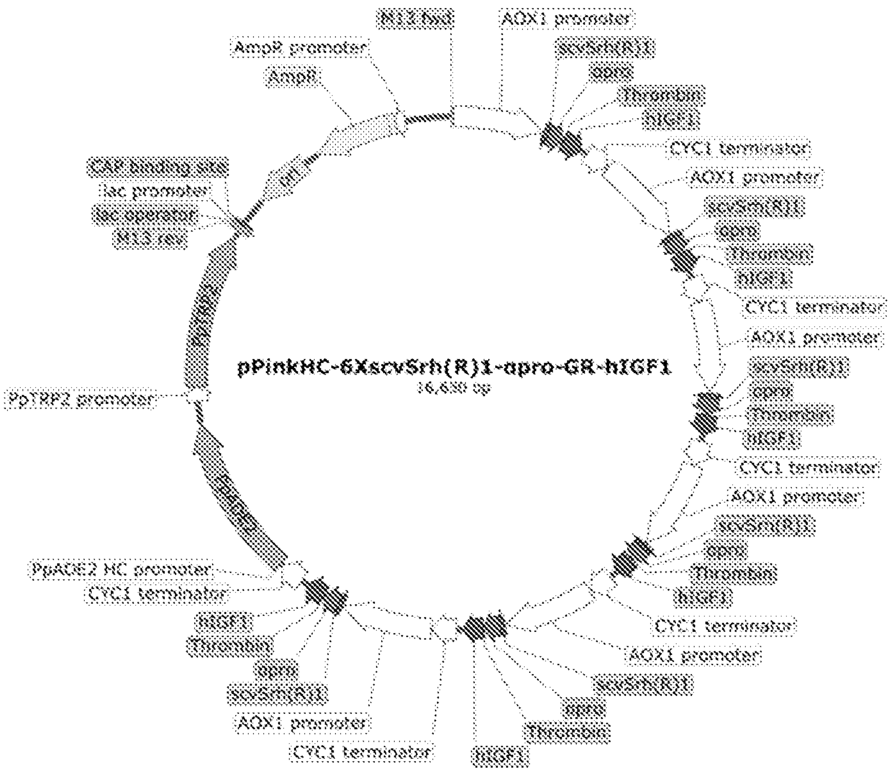

After confirming that there was no change except for the inserted base sequence by analyzing the base sequence of the cloned inserts, recombinant cells in which pPinkHC-6X scvSrh1(R)1_αpro-N-hIGF1 and pPinkHC-6X scvSrh1(R) 1_αpro-GR-hIGF1 were transformed were obtained in the same manner as that of Example 5 (see FIGS. 16A and 16B).

Figure 17:
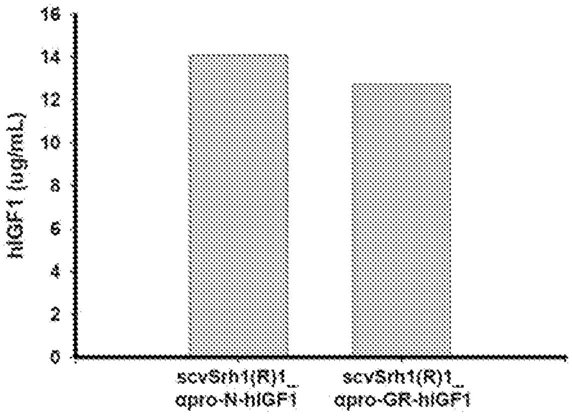
FIG. 17 is a result of quantifying hIFG1 secreted by culturing *Komagataella phaffii* transformed with each of vectors in which gene copy numbers of scvSrh(R)1-αpro-GR-hIGF1 and scvSrh(R)1-αpro-N-hIGF1 are increased to 6 in a BMMY medium by ELISA.

Thereafter, the productivity was measured by purifying hIGF1 by the methods of Examples 6 and 7 (see FIG. 17), required treatment (treatment with hydroxylamine or thrombin under common conditions) was performed, and the amino acid sequence was confirmed by analyzing the molecular weight with an LC-MS-MS method by eMass (see FIGS. 18A and 18B and FIGS. 19A and 19B).

From the results obtained by using the N and GR sequences additionally inserted into the amino terminus of hIGF1, it was confirmed that in the case where the hIGF1 was secreted and expressed using the hybrid signal sequence, the residual sequence was completely removed by introducing a new strategy for removing the residual sequence such as chemical cleavage or addition of a thrombin recognition sequence. In addition, although the exact mechanism was unknown, it was also confirmed that the hybrid signal sequence was completely removed during the analysis process using, as the control group, hIGF1 secreted by pPinkHC-6X scvSrh1(R)1_αpro-hIGF1 to which such a method was not applied.

As set forth above, according to an exemplary embodiment of the present invention, a heterologous signal sequence that significantly improves secretory expression of the human insulin-like growth factor-1 (hIGF1) is introduced into *Komagataella phaffii*, which is a unicellular eukaryotic cell, used as a host, such that various types of available signal sequences may be secured, and significantly improved secretory production may be achieved.

Special portions of contents of the present invention have been described in detail hereinabove, and it will be obvious to those skilled in the art that this detailed description is only an exemplary embodiment and the scope of the present invention is not limited by this detailed description. Therefore, the substantial scope of the present invention will be defined by the appended claims and equivalents thereof.

SEQUENCE LISTING

Sequence total quantity: 70
SEQ ID NO: 1 moltype = DNA length = 8137
FEATURE Location/Qualifiers
misc_feature 1..8137
note = pPinkHC-CU(R)-alphapro-hIGF1
misc_feature 952
note = n is A, T, G, or C
source 1..8137
mol_type = other DNA
organism = synthetic construct
SEQUENCE: 1
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg gaattcatgc gncagttctc 960
cattgccacc atcgccctct tcctgtcctc cgccatggcg gctccagtca acactacaac 1020
agaagatgaa acggcacaaa ttccggctga agctgtcatc ggttactcag atttagaagg 1080
ggatttcgat gttgctgttt tgccattttc caacagcaca aataacgggt tattgtttat 1140
aaatactact attgccagca ttgctgctaa agaagaaggg gtatctctcg agaaaagaga 1200
ggctgaagct ggcccggaaa ccctgtgtgg tgcggaactg gtggatgctc tgcaattcgt 1260
ctgtggtgac cgtggcttct acttcaataa accgaccggc tatggtagct ctagtcgtcg 1320
cgcgccgcag accggtattg tggatgaatg ctgttttcgt agctgtgacc tgcgtcgtct 1380
ggaaatgtat tgtgccccgc tgaaaccggc gaaatcggcg tgagcatgcc aaggcctcag 1440
gtaccggccg gccatttaaa tacaggcccc ttttcctttg tcgatatcat gtaattagtt 1500
atgtcacgct tacattcacg ccctcctccc acatccgctc taaccgaaaa ggaaggagtt 1560
agacaacctg aagtctaggt ccctatttat ttttttttaat agttatgtta gtattaagaa 1620
cgttatttat atttcaaatt tttctttttt ttctgtacaa acgcgtgtac gcatgtaaca 1680
ttatactgaa aaccttgctt gagaaggttt tgggacgctc gaaggcttta atttgcaagc 1740
tggatccgcg gccgccttcc aaactctcat ggattctcag gtaataggta ttctaggagg 1800
aggccagcta ggccgaatga ttgttgaggc cgctagcagg ctcaatatca agaccgtgat 1860
tcttgatgat ggtttttcac ctgctaagca cattaatgct gcgcaagacc acatcgacgg 1920
atcattcaaa gatgaggagg ctatcgccaa gttagctgcc aaatgtgatg ttctcactgt 1980
agagattgag catgtcaaca cagatgctct aaagagagtt caagacagaa ctggaatcaa 2040
gatatatcct ttaccagaga caatcgaact aatcaaggat aagtacttgc aaaaggaaca 2100
tttgatcaag cacaacattt cggtgacaaa gtctcagggt atagaatcta atgaaaaggc 2160
gctgcttttg tttggagaag agaatggatt tccatatctg ttgaagtccc ggactatggc 2220
ttatgatgga agaggcaatt ttgtagtgga gtctaaagag gacatcagta aggcattaga 2280
gttcttgaaa gatcgtccat tgtatgccga gaagtttgct cctttttgtta aagaattagc 2340
ggtaatggtt gtgagatcac tggaaggcga agtattctcc tacccaaccg tagaaactgt 2400
gcacaaggac aatatctgtc atattgtgta tgctccggcc agagttaatg acaccatcca 2460
aaagaaagct caaatattag ctgaaaacac tgtgaagact ttcccaggcg ctggaatctt 2520
cggagttgag atgttcctat tgtctgatgg agaacttctt gtaaatgaga ttgctccaag 2580
gccccacaat tctggtcact atacaatcga tgcatgtgta acatctcagt tcgaagcaca 2640
tgtaagagcc ataactggtc tgccaatgcc actagatttc accaaactat ctacttccaa 2700
caccaacgct attatgctca atgttttggg tgctgaaaaa tctcacgggg aattagagtt 2760
ttgtagaaga gccttagaaa caccccggtgc ttctgtatat ctgtacggaa agaccacccg 2820
attggctcgt aagatgggtc atatcaacat aataggatct tccatgttgg aagcagaaca 2880
aaagttagag tacattctag aagaatcaac ccacttacca tccagtactg tatcagctga 2940
cactaaaccg ttggttggag ttatcatggg ttcagactct gatctacctg tgatttcgaa 3000
aggttgcgat attttaaaac agtttggtgt tccattcgaa gttactattg tctctgctca 3060
tagaacacca cagagaatga ccagatatgc ctttgaagcc gctagtagag gtatcaaggc 3120
tatcattgca ggtgctggtg gtgctgctca tcttccagga atggttgctg ccatgactcc 3180
gttgccagtc attggtgttc ctgtcaaggg ctctacgttg gatggtgtag actcgctaca 3240
ctcgattgtc caaatgccta gaggtgttcc tgtggctacg gttgctatca acaacgccac 3300
caatgccgct ctgttggcca tcaggatttt aggtacaatt gaccacaaat ggcaaaagga 3360
aatgtccaag tatatgaatg caatggagac cgaagtgttg ggaaggcat ccaacttgga 3420
atctgaaggg tatgaatcct atttgaagaa tcgtctttga atttagtatt gtttttttaat 3480
agatgtatat ataatagtac acgtaactta tctattccat tcataatttt attttaaagg 3540
ttcggtagaa atttgtcctc caaaaaagttg gttagagcct ggcagttttg ataggcatta 3600
ttatagattg ggtaatattt accctgcacc tggaggaact ttgcaaagag cctcatgtgc 3660
ggcgcgccag gccataatgg ccaaacggtt tctcaattac tatatactac taaccattta 3720
cctgtagcgt atttcttttc cctcttcgcg aaagctcaag ggcatcttct tgactcatga 3780
aaaatatctg gatttcttct gacagatcat caccccttgag cccaactctc tagcctatga 3840
gtgtaagtga tagtcatctt gcaacagatt attttggaac gcaactaaca aagcagatac 3900
acccttcagc agaatccttt ctggatattg tgaagaatga tcgccaaagt cacagtcctg 3960
agacagttcc taatctttac cccatttaca agttcatcca atcagacttc ttaacgcctc 4020

-continued

```
atctggctta tatcaagctt accaacagtt cagaaactcc cagtccaagt ttcttgcttg  4080
aaagtgcgaa gaatggtgac accgttgaca ggtacacctt tatgggacat tcccccagaa  4140
aaataatcaa gactgggcct ttagagggtg ctgaagttga ccccttggtg cttctggaaa  4200
aagaactgaa gggcaccaga caagcgcaac ttcctggtat tcctcgtcta agtggtggtg  4260
ccataggata catctcgtac gattgtatta agtactttga accaaaaact gaaagaaaac  4320
tgaaagatgt tttgcaactt ccggaagcag ctttgatgtt gttcgacacg atcgtggctt  4380
ttgacaatgt ttatcaaaga ttccaggtaa ttggaaacgt ttctctatcc gttgatgact  4440
cggacgaagc tattcttgag aaatattata agacaagaga agaagtggaa aagatcagta  4500
aagtggtatt tgacaataaa actgttccct actatgaaca gaaagatatt attcaaggcc  4560
aaacgttcac ctctaatatt ggtcaggaag ggtatgaaaa ccatgttcgc aagctgaaag  4620
aacatattct gaaaggagac atcttccaag ctgttccctc tcaaagggta gccaggccga  4680
cctcattgca ccctttcaac atctatcgtc atttgagaac tgtcaatcct tctccataca  4740
tgttctatat tgactatcta gacttccaag ttgttggtgc ttcacctgaa ttactagtta  4800
aatccgacaa caacaacaaa atcatcacac atcctattgc tggaactctt cccagaggta  4860
aaactatcga agaggacgac aattatgcta agcaattgaa gtcgtctttg aaagacaggg  4920
ccgagcacgt catgctggta gatttggcca gaaatgatat taaccgtgtg tgtgagccca  4980
ccagtaccac ggttgatcgt ttattgactg tggagagatt ttctcatgtg atgcatcttg  5040
tgtcagaagt cagtggaaca ttgagaccaa acaagactcg cttcgatgct ttcagatcca  5100
ttttcccagc aggaaccgtc tccggtgctc cgaaggtaag agcaatgcaa ctcataggag  5160
aattggaagg agaaaagaga ggtgtttatg cgggggccgt aggacactgg tcgtacgatg  5220
gaaaatcgat ggacacatgt attgccttaa gaacaatggt cgtcaaggac ggtgtcgctt  5280
accttcaagc cggaggtgga attgtctacg attctgaccc ctatgacgag tacatcgaaa  5340
ccatgaacaa aatgagatcc aacaataaca ccatcttgga ggctgagaaa atctggaccg  5400
ataggttggc cagagacgag aatcaaagtg aatccgaaga aaacgatcaa tgaacggagg  5460
acgtaagtag gaatttatgg tttggccata atggcctagc ttggcgtaat catggtcata  5520
gctgtttcct gtgtgaaatt gttatccgct cacaattcca cacaacatac gagccggaag  5580
cataaagtgt aaagcctggg gtgcctaatg agtgagctaa ctcacattaa ttgcgttgcg  5640
ctcactgccc gctttccagt cgggaaacct gtcgtgccag ctgcattaat gaatcggcca  5700
acgcgcgggg agaggcggtt tgcgtattgg gcgctcttcc gcttcctcgc tcactgactc  5760
gctgcgctcg gtcgttcggc tgcggcgagc ggtatcagct cactcaaagg cggtaatacg  5820
gttatccaca gaatcagggg ataacgcagg aaagaacatg tgagcaaaag gccagcaaaa  5880
ggccaggaac cgtaaaaagg ccgcgttgct ggcgtttttc cataggctcc gcccccctga  5940
cgagcatcac aaaaatcgac gctcaagtca gaggtggcga aacccgacag gactataaag  6000
ataccaggcg tttccccctg gaagctccct cgtgcgctct cctgttccga ccctgccgct  6060
taccggatac ctgtccgcct ttctcccttc gggaagcgtg gcgctttctc atagctcacg  6120
ctgtaggtat ctcagttcgg tgtaggtcgt tcgctccaag ctgggctgtg tgcacgaacc  6180
ccccgttcag cccgaccgct gcgccttatc cggtaactat cgtcttgagt ccaacccggt  6240
aagacacgac ttatcgccac tggcagcagc cactggtaac aggattagca gagcgaggta  6300
tgtaggcggt gctacagagt tcttgaagtg gtggcctaac tacggctaca ctagaaggac  6360
agtatttggt atctgcgctc tgctgaagcc agttaccttc ggaaaaagag ttggtagctc  6420
ttgatccggc aaacaaacca ccgctggtag cggtggtttt tttgtttgca agcagcagat  6480
tacgcgcaga aaaaaaggat ctcaagaaga tcctttgatc ttttctacgg ggtctgacgc  6540
tcagtggaac gaaaactcac gttaagggat tttggtcatg agattatcaa aaaggatctt  6600
cacctagatc cttttaaatt aaaaatgaag ttttaaatca atctaaagta tatatgagta  6660
aacttggtct gacagttacc aatgcttaat cagtgaggca cctatctcag cgatctgtct  6720
atttcgttca tccatagttg cctgactccc cgtcgtgtag ataactacga tacgggaggg  6780
cttaccatct ggccccagtg ctgcaatgat accgcgagac ccacgctcac cggctccaga  6840
tttatcagca ataaaccagc cagccggaag ggccgagcgc agaagtggtc ctgcaacttt  6900
atccgcctcc atccagtcta ttaattgttg ccgggaagct agagtaagta gttcgccagt  6960
taatagtttg cgcaacgttg ttgccattgc tacaggcatc gtggtgtcac gctcgtcgtt  7020
tggtatggct tcattcagct ccggttccca acgatcaagg cgagttacat gatcccccat  7080
gttgtgcaaa aaagcggtta gctccttcgg tcctccgatc gttgtcagaa gtaagttggc  7140
cgcagtgtta tcactcatgg ttatggcagc actgcataat tctcttactg tcatgccatc  7200
cgtaagatgc ttttctgtga ctggtgagta ctcaaccaag tcattctgag aatagtgtat  7260
gcggcgaccg agttgctctt gcccggcgtc aatacgggat aataccgcgc cacatagcag  7320
aactttaaaa gtgctcatca ttggaaaacg ttcttcgggg cgaaaactct caaggatctt  7380
accgctgttg agatccagtt cgatgtaacc cactcgtgca cccaactgat cttcagcatc  7440
ttttactttc accagcgttt ctgggtgagc aaaaacagga aggcaaaatg ccgcaaaaaa  7500
gggaataagg gcgacacgga aatgttgaat actcatactc ttcctttttc aatattattg  7560
aagcatttat cagggttatt gtctcatgag cggatacata tttgaatgta tttagaaaaa  7620
taaacaaata ggggttccgc gcacatttcc ccgaaaagtg ccacctgacg tctaagaaac  7680
cattattatc atgacattaa cctataaaaa taggcgtatc acgaggccct ttcgtctcgc  7740
gcgtttcggt gatgacggtg aaaacctctg acacatgcag ctcccggaga cggtcacagc  7800
ttgtctgtaa gcggatgccg ggagcagaca agcccgtcag ggcgcgtcag cgggtgttgg  7860
cgggtgtcgg ggctggctta actatgcggc atcagagcag attgtactga gagtgcacca  7920
tatgcggtgt gaaataccgc acagatgcgt aaggagaaaa taccgcatca ggcgccattc  7980
gccattcagg ctgcgcaact gttgggaagg gcgatcggtg cgggcctctt cgctattacg  8040
ccagctggcg aaagggggat gtgctgcaag gcgattaagt tgggtaacgc cagggttttc  8100
ccagtcacga cgttgtaaaa cgacggccag tgaattg                          8137
```

| | |
|---|---|
| SEQ ID NO: 2 | moltype = DNA length = 8128 |
| FEATURE | Location/Qualifiers |
| misc_feature | 1..8128 |
| | note = pPinkHC-Hcf(R)5-alphapro-hIGF1 |
| misc_feature | 952 |
| | note = n is A, T, G, or C |
| source | 1..8128 |
| | mol_type = other DNA |
| | organism = synthetic construct |

-continued

SEQUENCE: 2
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggccccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aaccttttt tttatcatca ttattagctt 840
actttcataa ttgcgactgg ttccaattga caagcttttg attttaacga cttttaacga 900
caacttgaga agatcaaaaa acaactaatt attcgaaacg gaattcatgc gncaattcct 960
cgtcctcgcc cttgcatcgc ttgcagccgc agctccagtc aacactacaa cagaagatga 1020
aacggcacaa attccggctg aagctgtcat cggttactca gatttagaag gggatttcga 1080
tgttgctgtt ttgccatttt ccaacagcac aaataacggg ttattgttta taaatactac 1140
tattgccagc attgctgcta aagaagaagg ggtatctctc gagaaaagag aggctgaagc 1200
tggcccggaa accctgtgtg gtgcggaact ggtggatgct ctgcaattcg tctgtggtga 1260
ccgtggcttc tacttcaata aaccgaccgg ctatggtagc tctagtcgtc gcgcgccgca 1320
gaccggtatt gtggatgaat gctgttttcg tagctgtgac ctgcgtcgtc tggaaatgta 1380
ttgtgccccg ctgaaaccgg cgaaatcggc gtgagcatgc caaggcctca ggtaccggcc 1440
ggccatttaa atacaggccc cttttccttt gtcgatatca tgtaattagt tatgtcacgc 1500
ttacattcac gccctcctcc cacatccgct ctaaccgaaa aggaaggagt tagacaacct 1560
gaagtctagg tccctattta tttttttaa tagttatgtt agtattaaga acgttattta 1620
tatttcaaat ttttcttttt tttctgtaca aacgcgtgta cgcatgtaac attatactga 1680
aaaccttgct tgagaaggtt ttgggacgct cgaaggcttt aatttgcaag ctggatccgc 1740
ggccgccttc caaactctca tggattctca ggtaataggt attctaggag gaggccagct 1800
aggccgaatg attgttgagg ccgctagcag gctcaatatc aagaccgtga ttcttgatga 1860
tggtttttca cctgctaagc acattaatgc tgcgcaagac cacatcgacg gatcattcaa 1920
agatgaggag gctatcgcca agttagctgc caaatgtgat gttctcactg tagagattga 1980
gcatgtcaac acagatgctc taaagagagt tcaagacaga actggaatca agatatatcc 2040
tttaccagag acaatcgaac taatcaagga taagtacttg caaaaggaac atttgatcaa 2100
gcacaacatt tcggtgacaa agtctcaggg tatagaatct aatgaaaagg cgctgctttt 2160
gtttggagaa gagaatggat ttccatatct gttgaagtcc cggactatgg cttatgatgg 2220
aagaggcaat tttgtagtgg agtctaaaga ggacatcagt aaggcattag agttcttgaa 2280
agatcgtcca ttgtatgccg agaagtttgc tccttttgtt aaagaattag cggtaatggt 2340
tgtgagatca ctggaaggcg aagtattctc ctacccaacc gtagaaactg tgcacaagga 2400
caatatctgt catattgtgt atgctccggc cagagttaat gacaccatcc aaaagaaagc 2460
tcaaatatta gctgaaaaca ctgtgaagac tttcccaggc gctggaatct tcggagttga 2520
gatgttccta ttgtctgatg gagaacttct tgtaaatgag attgctccaa ggccccacaa 2580
ttctggtcac tatacaatcg atgcatgtgt aacatctcag ttcgaagcac atgtaagagc 2640
cataactggt ctgccaatgc cactagattt caccaaacta tctacttcca acaccaacgc 2700
tattatgctc aatgttttgg gtgctgaaaa atctcacggg gaattagagt tttgtagaag 2760
agccttagaa acacccggtg cttctgtata tctgtacgga aagaccaccc gattggctcg 2820
taagatgggt catatcaaca taataggatc ttccatgttg gaagcagaac aaaagttaga 2880
gtacattcta gaagaatcaa cccacttacc atccagtact gtatcagctg acactaaacc 2940
gttggttgga gttatcatgg gttcagactc tgatctacct gtgatttcga aaggttgcga 3000
tattttaaaa cagtttggtg ttccattcga agttactatt gtctctgctc atagaacacc 3060
acagagaatg accagatatg cctttgaagc cgctagtaga ggtatcaagg ctatcattgc 3120
aggtgctggt ggtgctgctc atcttccagg aatggttgct gccatgactc cgttgccagt 3180
cattggtgtt cctgtcaagg gctctacgtt ggatggtgta gactcgctac actcgattgt 3240
ccaaatgcct agaggtgttc ctgtggctac ggttgctatc aacaacgcca ccaatgccgc 3300
tctgttggcc atcaggattt taggtacaat tgaccacaaa tggcaaaagg aaatgtccaa 3360
gtatatgaat gcaatggaga ccgaagtgtt ggggaaggca tccaacttgg aatctgaagg 3420
gtatgaatcc tatttgaaga atcgtctttg aatttagtat tgttttttaa tagatgtata 3480
tataatagta cacgtaactt atctattcca ttcataattt tattttaaag gttcggtaga 3540
aatttgtcct ccaaaaaagtt ggttagagcc tggcagtttt gataggcatt attatagatt 3600
gggtaatatt taccctgcac ctggaggaac tttgcaaaga gcctcatgtg cggcgcgcca 3660
ggccataatg gccaaacggt ttctcaatta ctatatacta ctaaccattt acctgtagcg 3720
tatttctttt ccctcttcgc gaaagctcaa gggcatcttc ttgactcatg aaaaatatct 3780
ggatttcttc tgacagatca tcacccttga gcccaactct ctagcctatg agtgtaagtg 3840
atagtcatct tgcaacagat tattttggaa cgcaactaac aaagcagata cacccttcag 3900
cagaatcctt tctggatatt gtgaagaatg atcgccaaag tcacagtcct gagacagttc 3960
ctaatcttta ccccatttac aagttcatcc aatcagactt cttaacgcct catctggctt 4020
atatcaagct taccaacagt tcagaaactc ccagtccaag tttcttgctt gaaagtgcga 4080
agaatggtga caccgttgac aggtacacct ttatgggaca ttccccccaga aaaataatca 4140
agactgggcc tttagagggt gctgaagttg accccttggt gcttctggaa aaagaactga 4200
agggcaccag acaagcgcaa cttcctggta ttcctcgtct aagtggtggt gccataggat 4260
acatctcgta cgattgtatt aagtactttg aaccaaaaac tgaaagaaaa ctgaaagatg 4320
ttttgcaact tccggaagca gctttgatgt tgttcgacac gatcgtggct tttgacaatg 4380
tttatcaaag attccaggta attggaaacg tttctctatc cgttgatgac tcggacgaag 4440
ctattcttga gaaatattat aagacaagag aagaagtgga aaagatcagt aaagtggtat 4500
ttgacaataa aactgttccc tactatgaac agaaagatat tattcaaggc caaacgttca 4560
cctctaatat tggtcaggaa gggtatgaaa accatgttcg caagctgaaa gaacatattc 4620
tgaaaggaga catcttccaa gctgttccct ctcaaagggt agccaggccg acctcattgc 4680

```
acccttcaa catctatcgt catttgagaa ctgtcaatcc ttctccatac atgttctata 4740
ttgactatct agacttccaa gttgttggtg cttcacctga attactagtt aaatccgaca 4800
acaacaacaa aatcatcaca catcctattg ctggaactct tcccagaggt aaaactatcg 4860
aagaggacga caattatgct aagcaattga agtcgtcttt gaaagacagg gccgagcacg 4920
tcatgctggt agatttggcc agaaatgata ttaaccgtgt gtgtgagccc accagtacca 4980
cggttgatcg tttattgact gtggagagat tttctcatgt gatgcatctt gtgtcagaag 5040
tcagtggaac attgagacca aacaagactc gcttcgatgc tttcagatcc attttcccag 5100
caggaaccgt ctccggtgct ccgaaggtaa gagcaatgca actcatagga gaattggaag 5160
gagaaaagag aggtgtttat gcgggggccg taggacactg gtcgtacgat ggaaaatcga 5220
tggacacatg tattgcctta agaacaatgg tcgtcaagga cggtgtcgct taccttcaag 5280
ccggaggtgg aattgtctac gattctgacc cctatgacga gtacatcgaa accatgaaca 5340
aaatgagatc caacaataac accatcttgg aggctgagaa aatctggacc gataggttgg 5400
ccagagacga gaatcaaagt gaatccgaag aaaacgatca atgaacggag gacgtaagta 5460
ggaatttatg gtttggccat aatggcctag cttggcgtaa tcatggtcat agctgtttcc 5520
tgtgtgaaat tgttatccgc tcacaattcc acacaacata cgagccggaa gcataaagtg 5580
taaagcctgg ggtgcctaat gagtgagcta actcacatta attgcgttgc gctcactgcc 5640
cgctttccag tcgggaaacc tgtcgtgcca gctgcattaa tgaatcggcc aacgcgcggg 5700
gagaggcggt ttgcgtattg ggcgctcttc cgcttcctcg ctcactgact cgctgcgctc 5760
ggtcgttcgg ctgcggcgag cggtatcagc tcactcaaag gcggtaatac ggttatccac 5820
agaatcaggg gataacgcag gaaagaacat gtgagcaaaa ggccagcaaa aggccaggaa 5880
ccgtaaaaag gccgcgttgc tggcgttttt ccataggctc cgcccccctg acgagcatca 5940
caaaaatcga cgctcaagtc agaggtggcg aaacccgaca ggactataaa gataccaggc 6000
gtttccccct ggaagctccc tcgtgcgctc tcctgttccg accctgccgc ttaccggata 6060
cctgtccgcc tttctccctt cgggaagcgt ggcgctttct catagctcac gctgtaggta 6120
tctcagttcg gtgtaggtcg ttcgctccaa gctgggctgt gtgcacgaac cccccgttca 6180
gcccgaccgc tgcgccttat ccggtaacta tcgtcttgag tccaacccgg taagacacga 6240
cttatcgcca ctggcagcag ccactggtaa caggattagc agagcgaggt atgtaggcgg 6300
tgctacagag ttcttgaagt ggtggcctaa ctacggctac actagaagga cagtatttgg 6360
tatctgcgct ctgctgaagc cagttacctt cggaaaaaga gttggtagct cttgatccgg 6420
caaacaaacc accgctggta gcggtggttt ttttgtttgc aagcagcaga ttacgcgcag 6480
aaaaaaagga tctcaagaag atcctttgat cttttctacg gggtctgacg ctcagtggaa 6540
cgaaaactca cgttaaggga ttttggtcat gagattatca aaaaggatct tcacctagat 6600
ccttttaaat taaaaatgaa gttttaaatc aatctaaagt atatatgagt aaacttggtc 6660
tgacagttac caatgcttaa tcagtgaggc acctatctca gcgatctgtc tatttcgttc 6720
atccatagtt gcctgactcc ccgtcgtgta gataactacg atacgggagg gcttaccatc 6780
tggccccagt gctgcaatga taccgcgaga cccacgctca ccggctccag atttatcagc 6840
aataaaccag ccagccggaa gggccgagcg cagaagtggt cctgcaactt tatccgcctc 6900
catccagtct attaattgtt gccgggaagc tagagtaagt agttcgccag ttaatagttt 6960
gcgcaacgtt gttgccattg ctacaggcat cgtggtgtca cgctcgtcgt ttggtatggc 7020
ttcattcagc tccggttccc aacgatcaag gcgagttaca tgatccccca tgttgtgcaa 7080
aaaagcggtt agctccttcg gtcctccgat cgttgtcaga agtaagttgg ccgcagtgtt 7140
atcactcatg gttatggcag cactgcataa ttctcttact gtcatgccat ccgtaagatg 7200
cttttctgtg actggtgagt actcaaccaa gtcattctga gaatagtgta tgcggcgacc 7260
gagttgctct tgcccggcgt caatacggga taataccgcg ccacatagca gaactttaaa 7320
agtgctcatc attggaaaac gttcttcggg gcgaaaactc tcaaggatct taccgctgtt 7380
gagatccagt tcgatgtaac ccactcgtgc acccaactga tcttcagcat cttttacttt 7440
caccagcgtt tctgggtgag caaaaacagg aaggcaaaat gccgcaaaaa agggaataag 7500
ggcgacacgg aaatgttgaa tactcatact cttccttttt caatattatt gaagcattta 7560
tcagggttat tgtctcatga gcggatacat atttgaatgt atttagaaaa ataaacaaat 7620
aggggttccg cgcacatttc cccgaaaagt gccacctgac gtctaagaaa ccattattat 7680
catgacatta acctataaaa ataggcgtat cacgaggccc tttcgtctcg cgcgtttcgg 7740
tgatgacggt gaaaacctct gacacatgca gctcccggag acggtcacag cttgtctgta 7800
agcggatgcc gggagcagac aagcccgtca gggcgcgtca gcgggtgttg gcgggtgtcg 7860
gggctggctt aactatgcgg catcagagca gattgtactg agagtgcacc atatgcggtg 7920
tgaaataccg cacagatgcg taaggagaaa ataccgcatc aggcgccatt cgccattcag 7980
gctgcgcaac tgttgggaag ggcgatcggt gcgggcctct tcgctattac gccagctggc 8040
gaaaggggga tgtgctgcaa ggcgattaag ttgggtaacg ccagggtttt cccagtcacg 8100
acgttgtaaa acgacggcca gtgaattg 8128
```

```
SEQ ID NO: 3          moltype = DNA  length = 8143
FEATURE               Location/Qualifiers
misc_feature          1..8143
                      note = pPinkHC-MHP(R)1-alphapro-hIGF1
misc_feature          952
                      note = n is A, T, G, or C
source                1..8143
                      mol_type = other DNA
                      organism = synthetic construct
SEQUENCE: 3
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
```

-continued

```
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aaccttttt tttatcatca ttattagctt  840
actttcataa ttgcgactgg ttccaattga caagcttttg attttaacga cttttaacga  900
caacttgaga agatcaaaaa acaactaatt attcgaaacg gaattcatgc gncagttctc  960
caccatcatc gccaccatct tcgtcgcggc caccggtgcc gttgccgctc cagtcaacac  1020
tacaacagaa gatgaaacgg cacaaattcc ggctgaagct gtcatcggtt actcagattt  1080
agaaggggat ttcgatgttg ctgttttgcc attttccaac agcacaaata acgggttatt  1140
gtttataaat actactattg ccagcattgc tgctaaagaa gaaggggtat ctctcgagaa  1200
aagagaggct gaagctggcc cggaaaccct gtgtggtgcg gaactggtgg atgctctgca  1260
attcgtctgt ggtgaccgtg gcttctactt caataaaccg accggctatg gtagctctag  1320
tcgtcgcgcg ccgcagaccg gtattgtgga tgaatgctgt tttcgtagct gtgacctgcg  1380
tcgtctggaa atgtattgtg ccccgctgaa accggcgaaa tcggcgtgag catgccaagg  1440
cctcaggtac cggccggcca tttaaataca ggcccctttt cctttgtcga tatcatgtaa  1500
ttagttatgt cacgcttaca ttcacgccct cctcccacat ccgctctaac cgaaaaggaa  1560
ggagttagac aacctgaagt ctaggtccct atttattttt tttaatagtt atgttagtat  1620
taagaacgtt atttatattt caaatttttc tttttttct gtacaaacgc gtgtacgcat  1680
gtaacattat actgaaaacc ttgcttgaga aggttttggg acgctcgaag gctttaattt  1740
gcaagctgga tccgcggccg ccttccaaac tctcatggat tctcaggtaa taggtattct  1800
aggaggaggc cagctaggcc gaatgattgt tgaggccgct agcaggctca atatcaagac  1860
cgtgattctt gatgatggtt tttcacctgc taagcacatt aatgctgcgc aagaccacat  1920
cgacggatca ttcaaagatg aggaggctat cgccaagtta gctgccaaat gtgatgttct  1980
cactgtagag attgagcatg tcaacacaga tgctctaaag agagttcaag acagaactgg  2040
aatcaagata tatcctttac cagagacaat cgaactaatc aaggataagt acttgcaaaa  2100
ggaacatttg atcaagcaca acatttcggt gacaaagtct cagggtatag aatctaatga  2160
aaaggcgctg cttttgtttg gagaagagaa tggatttcca tatctgttga agtcccggac  2220
tatggcttat gatggaagag gcaattttgt agtggagtct aaagaggaca tcagtaaggc  2280
attagagttc ttgaaagatc gtccattgta tgccgagaag tttgctcctt ttgttaaaga  2340
attagcggta atggttgtga gatcactgga aggcgaagta ttctcctacc caaccgtaga  2400
aactgtgcac aaggacaata tctgtcatat tgtgtatgct ccggccagag ttaatgacac  2460
catccaaaag aaagctcaaa tattagctga aaacactgtg aagactttcc caggcgctgg  2520
aatcttcgga gttgagatgt tcctattgtc tgatggagaa cttcttgtaa atgagattgc  2580
tccaaggccc cacaattctg gtcactatac aatcgatgca tgtgtaacat ctcagttcga  2640
agcacatgta agagccataa ctggtctgcc aatgccacta gatttcacca aactatctac  2700
ttccaacacc aacgctatta tgctcaatgt tttgggtgct gaaaaatctc acggggaatt  2760
agagttttgt agaagagcct tagaaacacc cggtgcttct gtatatctgt acggaaagac  2820
cacccgattg gctcgtaaga tggtcatat caacataata ggatcttcca tgttggaagc  2880
agaacaaaag ttagagtaca ttctagaaga atcaacccac ttaccatcca gtactgtatc  2940
agctgacact aaaccgttgg ttggagttat catgggttca gactctgatc tacctgtgat  3000
ttcgaaaggt tgcgatattt taaaacagtt tggtgttcca ttcgaagtta ctattgtctc  3060
tgctcataga acaccacaga gaatgaccag atatgccttt gaagccgcta gtagaggtat  3120
caaggctatc attgcaggtg ctggtggtgc tgctcatctt ccaggaatgg ttgctgccat  3180
gactccgttg ccagtcattg gtgttcctgt caagggctct acgttggatg gtgtagactc  3240
gctacactcg attgtccaaa tgcctagagg tgttcctgtg gctacggttg ctatcaacaa  3300
cgccaccaat gccgctctgt tggccatcag gattttaggt acaattgacc acaaatggca  3360
aaaggaaatg tccaagtata tgaatgcaat ggagaccgaa gtgttgggga aggcatccaa  3420
cttggaatct gaagggtatg aatcctattt gaagaatcgt ctttgaattt agtattgttt  3480
tttaatagat gtatatataa tagtacacgt aacttatcta ttccattcat aattttattt  3540
taaaggttcg gtagaaattt gtcctccaaa aagttggtta gagcctggca gttttgatag  3600
gcattattat agattgggta atatttaccc tgcacctgga ggaactttgc aaagagcctc  3660
atgtgcggcg cgccaggcca taatggccaa acggtttctc aattactata tactactaac  3720
catttacctg tagcgtattt cttttccctc ttcgcgaaag ctcaagggca tcttcttgac  3780
tcatgaaaaa tatctggatt tcttctgaca gatcatcacc cttgagccca actctctagc  3840
ctatgagtgt aagtgatagt catcttgcaa cagattattt tggaacgcaa ctaacaaagc  3900
agatacaccc ttcagcagaa tcctttctgg atattgtgaa gaatgatcgc caaagtcaca  3960
gtcctgagac agttcctaat ctttacccca tttacaagtt catccaatca gacttcttaa  4020
cgcctcatct ggcttatatc aagcttacca acagttcaga aactcccagt ccaagtttct  4080
tgcttgaaag tgcgaagaat ggtgacaccg ttgacaggta cacctttatg ggacattccc  4140
ccagaaaaat aatcaagact gggcctttag agggtgctga agttgacccc ttggtgcttc  4200
tggaaaaaga actgaagggc accagacaag cgcaacttcc tggtattcct cgtctaagtg  4260
gtggtgccat aggatacatc tcgtacgatt gtattaagta ctttgaacca aaaactgaaa  4320
gaaaactgaa agatgtttg caacttccgg aagcagcttt gatgttgttc gacacgatcg  4380
tggcttttga caatgtttat caaagattcc aggtaattgg aaacgtttct ctatccgttg  4440
atgactcgga cgaagctatt cttgagaaat attataagac aagagaagaa gtggaaaaga  4500
tcagtaaagt ggtatttgac aataaaactg ttccctacta tgaacagaaa gatattattc  4560
aaggccaaac gttcacctct aatattggtc aggaagggta tgaaaaccat gttcgcaagc  4620
tgaaagaaca tattctgaaa ggagacatct tccaagctgt tccctctcaa agggtagcca  4680
ggccgacctc attgcaccct ttcaacatct atcgtcattt gagaactgtc aatccttctc  4740
catacatgtt ctatattgac tatctagact tccaagttgt tggtgcttca cctgaattac  4800
tagttaaatc cgacaacaac aacaaaatca tcacacatcc tattgctgga actcttccca  4860
gaggtaaaac tatcgaagag gacgacaatt atgctaagca attgaagtcg tctttgaaag  4920
acagggccga gcacgtcatg ctggtagatt tggccagaaa tgatattaac cgtgtgtgtg  4980
agcccaccag taccacggtt gatcgtttat tgactgtgga gagattttct catgtgatgc  5040
atcttgtgtc agaagtcagt ggaacattga gaccaaacaa gactcgcttc gatgctttca  5100
gatccatttt cccagcagga accgtctccg gtgctccgaa ggtaagagca atgcaactca  5160
taggagaatt ggaaggagaa aagagaggtg tttatgcggg ggccgtagga cactggtcgt  5220
acgatggaaa atcgatggac acatgtattg ccttaagaac aatggtcgtc aaggacggtg  5280
tcgcttacct tcaagccgga ggtggaattg tctacgattc tgacccctat gacgagtaca  5340
```

-continued tcgaaaccat gaacaaaatg agatccaaca ataacaccat cttggaggct gagaaaatct 5400
ggaccgatag gttggccaga gacgagaatc aaagtgaatc cgaagaaaac gatcaatgaa 5460
cggaggacgt aagtaggaat ttatggtttg gccataatgg cctagcttgg cgtaatcatg 5520
gtcatagctg tttcctgtgt gaaattgtta tccgctcaca attccacaca acatacgagc 5580
cggaagcata aagtgtaaag cctggggtgc ctaatgagtg agctaactca cattaattgc 5640
gttgcgctca ctgcccgctt tccagtcggg aaacctgtcg tgccagctgc attaatgaat 5700
cggccaacgc gcggggagag gcggtttgcg tattgggcgc tcttccgctt cctcgctcac 5760
tgactcgctg cgctcggtcg ttcggctgcg gcgagcggta tcagctcact caaaggcggt 5820
aatacggtta tccacagaat caggggataa cgcaggaaag aacatgtgag caaaaggcca 5880
gcaaaaggcc aggaaccgta aaaaggccgc gttgctggcg tttttccata ggctccgccc 5940
ccctgacgag catcacaaaa atcgacgctc aagtcagagg tggcgaaacc cgacaggact 6000
ataaagatac caggcgtttc cccctggaag ctccctcgtg cgctctcctg ttccgaccct 6060
gccgcttacc ggatacctgt ccgcctttct cccttcggga agcgtggcgc tttctcatag 6120
ctcacgctgt aggtatctca gttcggtgta ggtcgttcgc tccaagctgg gctgtgtgca 6180
cgaacccccc gttcagcccg accgctgcgc cttatccggt aactatcgtc ttgagtccaa 6240
cccggtaaga cacgacttat cgccactggc agcagccact ggtaacagga ttagcagagc 6300
gaggtatgta ggcggtgcta cagagttctt gaagtggtgg cctaactacg gctacactag 6360
aaggacagta tttggtatct gcgctctgct gaagccagtt accttcggaa aaagagttgg 6420
tagctcttga tccggcaaac aaaccaccgc tggtagcggt ggtttttttg tttgcaagca 6480
gcagattacg cgcagaaaaa aaggatctca agaagatcct ttgatctttt ctacggggtc 6540
tgacgctcag tggaacgaaa actcacgtta agggattttg gtcatgagat tatcaaaaag 6600
gatcttcacc tagatccttt taaattaaaa atgaagtttt aaatcaatct aaagtatata 6660
tgagtaaact tggtctgaca gttaccaatg cttaatcagt gaggcaccta tctcagcgat 6720
ctgtctattt cgttcatcca tagttgcctg actccccgtc gtgtagataa ctacgatacg 6780
ggagggctta ccatctggcc ccagtgctgc aatgataccg cgagacccac gctcaccggc 6840
tccagattta tcagcaataa accagccagc cggaagggcc gagcgcagaa gtggtcctgc 6900
aactttatcc gcctccatcc agtctattaa ttgttgccgg gaagctagag taagtagttc 6960
gccagttaat agtttgcgca acgttgttgc cattgctaca ggcatcgtgg tgtcacgctc 7020
gtcgtttggt atggcttcat tcagctccgg ttcccaacga tcaaggcgag ttacatgatc 7080
ccccatgttg tgcaaaaaag cggttagctc cttcggtcct ccgatcgttg tcagaagtaa 7140
gttggccgca gtgttatcac tcatggttat ggcagcactg cataattctc ttactgtcat 7200
gccatccgta agatgctttt ctgtgactgg tgagtactca accaagtcat tctgagaata 7260
gtgtatgcgg cgaccgagtt gctcttgccc ggcgtcaata cgggataata ccgcgccaca 7320
tagcagaact ttaaaagtgc tcatcattgg aaaacgttct tcggggcgaa aactctcaag 7380
gatcttaccg ctgttgagat ccagttcgat gtaacccact cgtgcaccca actgatcttc 7440
agcatctttt actttcacca gcgtttctgg gtgagcaaaa acaggaaggc aaaatgccgc 7500
aaaaaaggga ataagggcga cacggaaatg ttgaatactc atactcttcc tttttcaata 7560
ttattgaagc atttatcagg gttattgtct catgagcgga tacatatttg aatgtattta 7620
gaaaaataaa caaatagggg ttccgcgcac atttccccga aaagtgccac ctgacgtcta 7680
agaaaccatt attatcatga cattaaccta taaaaatagg cgtatcacga ggccctttcg 7740
tctcgcgcgt ttcggtgatg acggtgaaaa cctctgacac atgcagctcc cggagacggt 7800
cacagcttgt ctgtaagcgg atgccgggag cagacaagcc cgtcagggcg cgtcagcggg 7860
tgttggcggg tgtcggggct ggcttaacta tgcggcatca gagcagattg tactgagagt 7920
gcaccatatg cggtgtgaaa taccgcacag atgcgtaagg agaaaatacc gcatcaggcg 7980
ccattcgcca ttcaggctgc gcaactgttg ggaagggcga tcggtgcggg cctcttcgct 8040
attacgccag ctggcgaaag ggggatgtgc tgcaaggcga ttaagttggg taacgccagg 8100
gttttcccag tcacgacgtt gtaaaacgac ggccagtgaa ttg 8143

SEQ ID NO: 4 moltype = DNA length = 8131
FEATURE Location/Qualifiers
misc_feature 1..8131
note = pPinkHC-Srh(R)1-alphapro-hIGF1
misc_feature 952
note = n is A,T, G, or C
source 1..8131
mol_type = other DNA
organism = synthetic construct
SEQUENCE: 4
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg gaattcatgc gncagttctc 960
catcgttgcc ctcttcgcta ctggcgctct cgccgctcca gtcaacacta caacagaaga 1020
tgaaacggca caaattccgg ctgaagctgt catcggttac tcagatttag aaggggattt 1080
cgatgttgct gttttgccat tttccaacag cacaaataac gggttattgt ttataaatac 1140
tactattgcc agcattgctg ctaaagaaga aggggtatct ctcgagaaaa gagaggctga 1200
agctggcccg gaaaccctgt gtggtgcgga actggtggat gctctgcaat tcgtctgtgg 1260

-continued

```
tgaccgtggc ttctacttca ataaaccgac cggctatggt agctctagtc gtcgcgcgcc  1320
gcagaccggt attgtggatg aatgctgttt tcgtagctgt gacctgcgtc gtctggaaat  1380
gtattgtgcc ccgctgaaac cggcgaaatc ggcgtgagca tgccaaggcc tcaggtaccg  1440
gccggccatt taaatacagg cccctttcc tttgtcgata tcatgtaatt agttatgtca  1500
cgcttacatt cacgccctcc tcccacatcc gctctaaccg aaaaggaagg agttagacaa  1560
cctgaagtct aggtccctat ttattttttt taatagttat gttagtatta agaacgttat  1620
ttatatttca aatttttctt ttttttctgt acaaacgcgt gtacgcatgt aacattatac  1680
tgaaaacctt gcttgagaag gttttgggac gctcgaaggc tttaatttgc aagctggatc  1740
cgcggccgcc ttccaaactc tcatggattc tcaggtaata ggtattctag gaggaggcca  1800
gctaggccga atgattgttg aggccgctag caggctcaat atcaagaccg tgattcttga  1860
tgatggtttt tcacctgcta agcacattaa tgctgcgcaa gaccacatcg acggatcatt  1920
caaagatgag gaggctatcg ccaagttagc tgccaaatgt gatgttctca ctgtagagat  1980
tgagcatgtc aacacagatg ctctaaagag agttcaagac agaactggaa tcaagatata  2040
tcctttacca gagacaatcg aactaatcaa ggataagtac ttgcaaaagg aacatttgat  2100
caagcacaac atttcggtga caaagtctca gggtatagaa tctaatgaaa aggcgctgct  2160
tttgtttgga gaagagaatg gatttccata tctgttgaag tcccggacta tggcttatga  2220
tggaagaggc aattttgtag tggagtctaa agaggacatc agtaaggcat tagagttctt  2280
gaaagatcgt ccattgtatg ccgagaagtt tgctcctttt gttaaagaat tagcggtaat  2340
ggttgtgaga tcactggaag gcgaagtatt ctcctaccca accgtagaaa ctgtgcacaa  2400
ggacaatatc tgtcatattg tgtatgctcc ggccagagtt aatgacacca tccaaaagaa  2460
agctcaaata ttagctgaaa acactgtgaa gactttccca ggcgctggaa tcttcggagt  2520
tgagatgttc ctattgtctg atggagaact tcttgtaaat gagattgctc caaggcccca  2580
caattctggt cactatacaa tcgatgcatg tgtaacatct cagttcgaag cacatgtaag  2640
agccataact ggtctgccaa tgccactaga tttcaccaaa ctatctactt ccaacaccaa  2700
cgctattatg ctcaatgttt tgggtgctga aaaatctcac ggggaattag agttttgtag  2760
aagagcctta gaaacacccg gtgcttctgt atatctgtac ggaaagacca cccgattggc  2820
tcgtaagatg ggtcatatca acataatagg atcttccatg ttggaagcag aacaaaagtt  2880
agagtacatt ctagaagaat caacccactt accatccagt actgtatcag ctgacactaa  2940
accgttggtt ggagttatca tgggttcaga ctctgatcta cctgtgattt cgaaaggttg  3000
cgatatttta aaacagtttg gtgttccatt cgaagttact attgtctctg ctcatagaac  3060
accacagaga atgaccagat atgcctttga agccgctagt agaggtatca aggctatcat  3120
tgcaggtgct ggtggtgctg ctcatcttcc aggaatggtt gctgccatga ctccgttgcc  3180
agtcattggt gttcctgtca agggctctac gttggatggt gtagactcgc tacactcgat  3240
tgtccaaatg cctagaggtg ttcctgtggc tacggttgct atcaacaacg ccaccaatgc  3300
cgctctgttg gccatcagga ttttaggtac aattgaccac aaatggcaaa aggaaatgtc  3360
caagtatatg aatgcaatgg agaccgaagt gttggggaag gcatccaact tggaatctga  3420
agggtatgaa tcctatttga agaatcgtct ttgaatttag tattgttttt taatagatgt  3480
atatataata gtacacgtaa cttatctatt ccattcataa ttttatttta aaggttcggt  3540
agaaatttgt cctccaaaaa gttggttaga gcctggcagt tttgataggc attattatag  3600
attgggtaat atttaccctg cacctggagg aactttgcaa agagcctcat gtgcggcgcg  3660
ccaggccata atggccaaac ggtttctcaa ttactatata ctactaacca tttacctgta  3720
gcgtatttct tttccctctt cgcgaaagct caagggcatc ttcttgactc atgaaaaata  3780
tctggatttc ttctgacaga tcatcaccct tgagcccaac tctctagcct atgagtgtaa  3840
gtgatagtca tcttgcaaca gattattttg gaacgcaact aacaaagcag atacaccctt  3900
cagcagaatc ctttctggat attgtgaaga atgatcgcca aagtcacagt cctgagacag  3960
ttcctaatct ttaccccatt tacaagttca tccaatcaga cttcttaacg cctcatctgg  4020
cttatatcaa gcttaccaac agttcagaaa ctcccagtcc aagtttcttg cttgaaagtg  4080
cgaagaatgg tgacaccgtt gacaggtaca cctttatggg acattccccc agaaaaataa  4140
tcaagactgg gcctttagag ggtgctgaag ttgacccctt ggtgcttctg gaaaaagaac  4200
tgaagggcac cagacaagcg caacttcctg gtattcctcg tctaagtggt ggtgccatag  4260
gatacatctc gtacgattgt attaagtact ttgaaccaaa aactgaaaga aaactgaaag  4320
atgttttgca acttccggaa gcagctttga tgttgttcga cacgatcgtg gcttttgaca  4380
atgtttatca aagattccag gtaattggaa acgtttctct atccgttgat gactcggacg  4440
aagctattct tgagaaatat tataagacaa gagaagaagt ggaaaagatc agtaaagtgg  4500
tatttgacaa taaaactgtt ccctactatg aacagaaaga tattattcaa ggccaaacgt  4560
tcacctctaa tattggtcag gaagggtatg aaaaccatgt tcgcaagctg aaagaacata  4620
ttctgaaagg agacatcttc caagctgttc cctctcaaag ggtagccagg ccgacctcat  4680
tgcacccttt caacatctat cgtcatttga gaactgtcaa tccttctcca tacatgttct  4740
atattgacta tctagacttc caagttgttg gtgcttcacc tgaattacta gttaaatccg  4800
acaacaacaa caaaatcatc acacatccta ttgctggaac tcttcccaga ggtaaaacta  4860
tcgaagagga cgacaattat gctaagcaat tgaagtcgtc tttgaaagac agggccgagc  4920
acgtcatgct ggtagatttg gccagaaatg atattaaccg tgtgtgtgag cccaccagta  4980
ccacggttga tcgtttattg actgtggaga gattttctca tgtgatgcat cttgtgtcag  5040
aagtcagtgg aacattgaga ccaaacaaga ctcgcttcga tgctttcaga tccattttcc  5100
cagcaggaac cgtctccggt gctccgaagg taagagcaat gcaactcata ggagaattgg  5160
aaggagaaaa gagaggtgtt tatgcggggg ccgtaggaca ctggtcgtac gatggaaaat  5220
cgatggacac atgtattgcc ttaagaacaa tggtcgtcaa ggacggtgtc gcttaccttc  5280
aagccggagg tggaattgtc tacgattctg accccatga cgagtacatc gaaaccatga  5340
acaaaatgag atccaacaat aacaccatct tggaggctga gaaaatctgg accgataggt  5400
tggccagaga cgagaatcaa agtgaatccg aagaaaacga tcaatgaacg gaggacgtaa  5460
gtaggaattt atggtttggc cataatggcc tagcttggcg taatcatggt catagctgtt  5520
tcctgtgtga aattgttatc cgctcacaat tccacacaac atacgagccg gaagcataaa  5580
gtgtaaagcc tggggtgcct aatgagtgag ctaactcaca ttaattgcgt tgcgctcact  5640
gcccgctttc cagtcgggaa acctgtcgtg ccagctgcat taatgaatcg gccaacgcgc  5700
ggggagaggc ggtttgcgta ttgggcgctc ttccgcttcc tcgctcactg actcgctgcg  5760
ctcggtcgtt cggctgcggc gagcggtatc agctcactca aaggcggtaa tacggttatc  5820
cacagaatca ggggataacg caggaaagaa catgtgagca aaaggccagc aaaaggccag  5880
gaaccgtaaa aaggccgcgt tgctggcgtt tttccatagg ctccgccccc ctgacgagca  5940
tcacaaaaat cgacgctcaa gtcagaggtg gcgaaacccg acaggactat aaagatacca  6000
```

```
ggcgtttccc cctggaagct ccctcgtgcg ctctcctgtt ccgaccctgc cgcttaccgg  6060
atacctgtcc gcctttctcc cttcgggaag cgtggcgctt tctcatagct cacgctgtag  6120
gtatctcagt tcggtgtagg tcgttcgctc caagctgggc tgtgtgcacg aaccccccgt  6180
tcagcccgac cgctgcgcct tatccggtaa ctatcgtctt gagtccaacc cggtaagaca  6240
cgacttatcg ccactggcag cagccactgg taacaggatt agcagagcga ggtatgtagg  6300
cggtgctaca gagttcttga agtggtggcc taactacggc tacactagaa ggacagtatt  6360
tggtatctgc gctctgctga agccagttac cttcggaaaa agagttggta gctcttgatc  6420
cggcaaacaa accaccgctg gtagcggtgg tttttttgtt tgcaagcagc agattacgcg  6480
cagaaaaaaa ggatctcaag aagatccttt gatcttttct acggggtctg acgctcagtg  6540
gaacgaaaac tcacgttaag ggattttggt catgagatta tcaaaaagga tcttcaccta  6600
gatcctttta aattaaaaat gaagttttaa atcaatctaa agtatatatg agtaaacttg  6660
gtctgacagt taccaatgct taatcagtga ggcacctatc tcagcgatct gtctatttcg  6720
ttcatccata gttgcctgac tccccgtcgt gtagataact acgatacggg agggcttacc  6780
atctggcccc agtgctgcaa tgataccgcg agacccacgc tcaccggctc cagatttatc  6840
agcaataaac cagccagccg gaagggccga gcgcagaagt ggtcctgcaa ctttatccgc  6900
ctccatccag tctattaatt gttgccggga agctagagta agtagttcgc cagttaatag  6960
tttgcgcaac gttgttgcca ttgctacagg catcgtggtg tcacgctcgt cgtttggtat  7020
ggcttcattc agctccggtt cccaacgatc aaggcgagtt acatgatccc ccatgttgtg  7080
caaaaaagcg gttagctcct tcggtcctcc gatcgttgtc agaagtaagt tggccgcagt  7140
gttatcactc atggttatgg cagcactgca taattctctt actgtcatgc catccgtaag  7200
atgcttttct gtgactggtg agtactcaac caagtcattc tgagaatagt gtatgcggcg  7260
accgagttgc tcttgcccgg cgtcaatacg ggataatacc gcgccacata gcagaacttt  7320
aaaagtgctc atcattggaa aacgttcttc ggggcgaaaa ctctcaagga tcttaccgct  7380
gttgagatcc agttcgatgt aacccactcg tgcacccaac tgatcttcag catcttttac  7440
tttcaccagc gtttctgggt gagcaaaaac aggaaggcaa aatgccgcaa aaaagggaat  7500
aagggcgaca cggaaatgtt gaatactcat actcttcctt tttcaatatt attgaagcat  7560
ttatcagggt tattgtctca tgagcggata catatttgaa tgtatttaga aaaataaaca  7620
aataggggtt ccgcgcacat ttccccgaaa agtgccacct gacgtctaag aaaccattat  7680
tatcatgaca ttaacctata aaaataggcg tatcacgagg ccctttcgtc tcgcgcgttt  7740
cggtgatgac ggtgaaaacc tctgacacat gcagctcccg gagacggtca cagcttgtct  7800
gtaagcggat gccgggagca gacaagcccg tcagggcgcg tcagcgggtg ttggcgggtg  7860
tcggggctgg cttaactatg cggcatcaga gcagattgta ctgagagtgc accatatgcg  7920
gtgtgaaata ccgcacagat gcgtaaggag aaaataccgc atcaggcgcc attcgccatt  7980
caggctgcgc aactgttggg aagggcgatc ggtgcgggcc tcttcgctat tacgccagct  8040
ggcgaaaggg ggatgtgctg caaggcgatt aagttgggta acgccagggt tttcccagtc  8100
acgacgttgt aaaacgacgg ccagtgaatt g                                 8131
```

```
SEQ ID NO: 5           moltype = DNA  length = 263
FEATURE                Location/Qualifiers
misc_feature           1..263
                       note = Kozak-scvSrh(R)1-alphapro
source                 1..263
                       mol_type = other DNA
                       organism = synthetic construct
SEQUENCE: 5
aaaaaatgcg gcaattctct attgttgctc tgttcgctac tggcgctctc gccgctccag  60
tcaacactac aacagaagat gaaacggcac aaattccggc tgaagctgtc atcggttact  120
cagatttaga aggggatttc gatgttgctg ttttgccatt ttccaacagc acaaataacg  180
ggttattgtt tataaatact actattgcca gcattgctgc taaagaagaa ggggtatctc  240
tcgagaaaag agaggctgaa gct                                          263
```

```
SEQ ID NO: 6           moltype = DNA  length = 16836
FEATURE                Location/Qualifiers
misc_feature           1..16836
                       note = pPinkHC-6XscvSrh(R)1-alphapro-hIGF1
source                 1..16836
                       mol_type = other DNA
                       organism = synthetic construct
SEQUENCE: 6
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcaaaa aatgcggcaa  960
ttctctattg ttgctctgtt cgctactggc gctctcgccg ctccagtcaa cactacaaca  1020
gaagatgaaa cggcacaaat tccggctgaa gctgtcatcg gttactcaga tttagaaggg  1080
gatttcgatg ttgctgtttt gccattttcc aacagcacaa ataacgggtt attgtttata  1140
aatactacta ttgccagcat tgctgctaaa gaagaagggg tatctctcga gaaaagagag  1200
```

-continued

```
gctgaagctg gcccggaaac cctgtgtggt gcggaactgg tggatgctct gcaattcgtc  1260
tgtggtgacc gtggcttcta cttcaataaa ccgaccggct atggtagctc tagtcgtcgc  1320
gcgccgcaga ccggtattgt ggatgaatgc tgttttcgta gctgtgacct gcgtcgtctg  1380
gaaatgtatt gtgccccgct gaaaccggcg aaatcggcgt gagcatgcca aggcctcagg  1440
taccggccgg ccatttaaat acaggcccct tttcctttgt cgatatcatg taattagtta  1500
tgtcacgctt acattcacgc cctcctccca catccgctct aaccgaaaag gaaggagtta  1560
gacaacctga agtctaggtc cctatttatt ttttttaata gttatgttag tattaagaac  1620
gttatttata tttcaaattt ttcttttttt tctgtacaaa cgcgtgtacg catgtaacat  1680
tatactgaaa accttgcttg agaaggtttt gggacgctcg aaggctttaa tttgcaagct  1740
ggatctaaca tccaaagacg aaaggttgaa tgaaaccttt ttgccatccg acatccacag  1800
gtccattctc acacataagt gccaaacgca acaggagggg atacactagc agcagaccgt  1860
tgcaaacgca ggacctccac tcctcttctc ctcaacaccc acttttgcca tcgaaaaacc  1920
agcccagtta ttgggcttga ttggagctcg ctcattccaa ttccttctat taggctacta  1980
acaccatgac tttattagcc tgtctatcct ggcccccctg gcgaggttca tgtttgttta  2040
tttccgaatg caacaagctc cgcattacac ccgaacatca ctccagatga gggctttctg  2100
agtgtggggt caaatagttt catgttcccc aaatggccca aaactgacag tttaaacgct  2160
gtcttggaac ctaatatgac aaaagcgtga tctcatccaa gatgaactaa gtttggttcg  2220
ttgaaatgct aacggccagt tggtcaaaaa gaaacttcca aaagtcggca taccgtttgt  2280
cttgtttggt attgattgac gaatgctcaa aaataatctc attaatgctt agcgcagtct  2340
ctctatcgct tctgaacccc ggtgcacctg tgccgaaacg caaatgggga aacacccgct  2400
ttttggatga ttatgcattg tctccacatt gtatgcttcc aagattctgg tgggaatact  2460
gctgatagcc taacgttcat gatcaaaatt taactgttct aacccctact tgacagcaat  2520
atataaacag aaggaagctg ccctgtctta aacctttttt tttatcatca ttattagctt  2580
actttcataa ttgcgactgg ttccaattga caagcttttg attttaacga cttttaacga  2640
caacttgaga agatcaaaaa acaactaatt attcgaaacg gaattcaaaa aatgcggcaa  2700
ttctctattg ttgctctgtt cgctactggc gctctcgccg ctccagtcaa cactacaaca  2760
gaagatgaaa cggcacaaat tccggctgaa gctgtcatcg gttactcaga tttagaaggg  2820
gatttcgatg ttgctgtttt gccattttcc aacagcacaa ataacgggtt attgtttata  2880
aatactacta ttgccagcat tgctgctaaa gaagaagggg tatctctcga gaaaagagag  2940
gctgaagctg gcccggaaac cctgtgtggt gcggaactgg tggatgctct gcaattcgtc  3000
tgtggtgacc gtggcttcta cttcaataaa ccgaccggct atggtagctc tagtcgtcgc  3060
gcgccgcaga ccggtattgt ggatgaatgc tgttttcgta gctgtgacct gcgtcgtctg  3120
gaaatgtatt gtgccccgct gaaaccggcg aaatcggcgt gagcatgcca aggcctcagg  3180
taccggccgg ccatttaaat acaggcccct tttcctttgt cgatatcatg taattagtta  3240
tgtcacgctt acattcacgc cctcctccca catccgctct aaccgaaaag gaaggagtta  3300
gacaacctga agtctaggtc cctatttatt ttttttaata gttatgttag tattaagaac  3360
gttatttata tttcaaattt ttcttttttt tctgtacaaa cgcgtgtacg catgtaacat  3420
tatactgaaa accttgcttg agaaggtttt gggacgctcg aaggctttaa tttgcaagct  3480
ggatctaaca tccaaagacg aaaggttgaa tgaaaccttt ttgccatccg acatccacag  3540
gtccattctc acacataagt gccaaacgca acaggagggg atacactagc agcagaccgt  3600
tgcaaacgca ggacctccac tcctcttctc ctcaacaccc acttttgcca tcgaaaaacc  3660
agcccagtta ttgggcttga ttggagctcg ctcattccaa ttccttctat taggctacta  3720
acaccatgac tttattagcc tgtctatcct ggcccccctg gcgaggttca tgtttgttta  3780
tttccgaatg caacaagctc cgcattacac ccgaacatca ctccagatga gggctttctg  3840
agtgtggggt caaatagttt catgttcccc aaatggccca aaactgacag tttaaacgct  3900
gtcttggaac ctaatatgac aaaagcgtga tctcatccaa gatgaactaa gtttggttcg  3960
ttgaaatgct aacggccagt tggtcaaaaa gaaacttcca aaagtcggca taccgtttgt  4020
cttgtttggt attgattgac gaatgctcaa aaataatctc attaatgctt agcgcagtct  4080
ctctatcgct tctgaacccc ggtgcacctg tgccgaaacg caaatgggga aacacccgct  4140
ttttggatga ttatgcattg tctccacatt gtatgcttcc aagattctgg tgggaatact  4200
gctgatagcc taacgttcat gatcaaaatt taactgttct aacccctact tgacagcaat  4260
atataaacag aaggaagctg ccctgtctta aacctttttt tttatcatca ttattagctt  4320
actttcataa ttgcgactgg ttccaattga caagcttttg attttaacga cttttaacga  4380
caacttgaga agatcaaaaa acaactaatt attcgaaacg gaattcaaaa aatgcggcaa  4440
ttctctattg ttgctctgtt cgctactggc gctctcgccg ctccagtcaa cactacaaca  4500
gaagatgaaa cggcacaaat tccggctgaa gctgtcatcg gttactcaga tttagaaggg  4560
gatttcgatg ttgctgtttt gccattttcc aacagcacaa ataacgggtt attgtttata  4620
aatactacta ttgccagcat tgctgctaaa gaagaagggg tatctctcga gaaaagagag  4680
gctgaagctg gcccggaaac cctgtgtggt gcggaactgg tggatgctct gcaattcgtc  4740
tgtggtgacc gtggcttcta cttcaataaa ccgaccggct atggtagctc tagtcgtcgc  4800
gcgccgcaga ccggtattgt ggatgaatgc tgttttcgta gctgtgacct gcgtcgtctg  4860
gaaatgtatt gtgccccgct gaaaccggcg aaatcggcgt gagcatgcca aggcctcagg  4920
taccggccgg ccatttaaat acaggcccct tttcctttgt cgatatcatg taattagtta  4980
tgtcacgctt acattcacgc cctcctccca catccgctct aaccgaaaag gaaggagtta  5040
gacaacctga agtctaggtc cctatttatt ttttttaata gttatgttag tattaagaac  5100
gttatttata tttcaaattt ttcttttttt tctgtacaaa cgcgtgtacg catgtaacat  5160
tatactgaaa accttgcttg agaaggtttt gggacgctcg aaggctttaa tttgcaagct  5220
ggatctaaca tccaaagacg aaaggttgaa tgaaaccttt ttgccatccg acatccacag  5280
gtccattctc acacataagt gccaaacgca acaggagggg atacactagc agcagaccgt  5340
tgcaaacgca ggacctccac tcctcttctc ctcaacaccc acttttgcca tcgaaaaacc  5400
agcccagtta ttgggcttga ttggagctcg ctcattccaa ttccttctat taggctacta  5460
acaccatgac tttattagcc tgtctatcct ggcccccctg gcgaggttca tgtttgttta  5520
tttccgaatg caacaagctc cgcattacac ccgaacatca ctccagatga gggctttctg  5580
agtgtggggt caaatagttt catgttcccc aaatggccca aaactgacag tttaaacgct  5640
gtcttggaac ctaatatgac aaaagcgtga tctcatccaa gatgaactaa gtttggttcg  5700
ttgaaatgct aacggccagt tggtcaaaaa gaaacttcca aaagtcggca taccgtttgt  5760
cttgtttggt attgattgac gaatgctcaa aaataatctc attaatgctt agcgcagtct  5820
ctctatcgct tctgaacccc ggtgcacctg tgccgaaacg caaatgggga aacacccgct  5880
ttttggatga ttatgcattg tctccacatt gtatgcttcc aagattctgg tgggaatact  5940
```

-continued

```
gctgatagcc taacgttcat gatcaaaatt taactgttct aacccctact tgacagcaat  6000
atataaacag aaggaagctg ccctgtctta aacctttttt tttatcatca ttattagctt  6060
actttcataa ttgcgactgg ttccaattga caagcttttg attttaacga cttttaacga  6120
caacttgaga agatcaaaaa acaactaatt attcgaaacg gaattcaaaa aatgcggcaa  6180
ttctctattg ttgctctgtt cgctactggc gctctcgccg ctccagtcaa cactacaaca  6240
gaagatgaaa cggcacaaat tccggctgaa gctgtcatcg gttactcaga tttagaaggg  6300
gatttcgatg ttgctgtttt gccattttcc aacagcacaa ataacgggtt attgtttata  6360
aatactacta ttgccagcat tgctgctaaa gaagaagggg tatctctcga gaaaagagag  6420
gctgaagctg gcccggaaac cctgtgtggt gcggaactgg tggatgctct gcaattcgtc  6480
tgtggtgacc gtggcttcta cttcaataaa ccgaccggct atggtagctc tagtcgtcgc  6540
gcgccgcaga ccggtattgt ggatgaatgc tgttttcgta gctgtgacct gcgtcgtctg  6600
gaaatgtatt gtgccccgct gaaaccggcg aaatcggcgt gagcatgcca aggcctcagg  6660
taccggccgg ccatttaaat acaggcccct tttcctttgt cgatatcatg taattagtta  6720
tgtcacgctt acattcacgc cctcctccca catccgctct aaccgaaaag gaaggagtta  6780
gacaacctga agtctaggtc cctatttatt tttttaata gttatgttag tattaagaac  6840
gttatttata tttcaaattt ttcttttttt tctgtacaaa cgcgtgtacg catgtaacat  6900
tatactgaaa accttgcttg agaaggtttt gggacgctcg aaggctttaa tttgcaagct  6960
ggatctaaca tccaaagacg aaaggttgaa tgaaaccttt ttgccatccg acatccacag  7020
gtccattctc acacataagt gccaaacgca acaggagggg atacactagc agcagaccgt  7080
tgcaaacgca ggacctccac tcctcttctc ctcaacaccc acttttgcca tcgaaaaacc  7140
agcccagtta ttgggcttga ttggagctcg ctcattccaa ttccttctat taggctacta  7200
acaccatgac tttattagcc tgtctatcct ggcccccctg gcgaggttca tgtttgttta  7260
tttccgaatg caacaagctc cgcattacac ccgaacatca ctccagatga gggctttctg  7320
agtgtggggt caaatagttt catgttcccc aaatggccca aaactgacag tttaaacgct  7380
gtcttggaac ctaatatgac aaaagcgtga tctcatccaa gatgaactaa gtttggttcg  7440
ttgaaatgct aacggccagt tggtcaaaaa gaaacttcca aaagtcggca taccgtttgt  7500
cttgtttggt attgattgac gaatgctcaa aaataatctc attaatgctt agcgcagtct  7560
ctctatcgct tctgaacccc ggtgcacctg tgccgaaacg caaatgggga aacacccgct  7620
ttttggatga ttatgcattg tctccacatt gtatgcttcc aagattctgg tgggaatact  7680
gctgatagcc taacgttcat gatcaaaatt taactgttct aacccctact tgacagcaat  7740
atataaacag aaggaagctg ccctgtctta aacctttttt tttatcatca ttattagctt  7800
actttcataa ttgcgactgg ttccaattga caagcttttg attttaacga cttttaacga  7860
caacttgaga agatcaaaaa acaactaatt attcgaaacg gaattcaaaa aatgcggcaa  7920
ttctctattg ttgctctgtt cgctactggc gctctcgccg ctccagtcaa cactacaaca  7980
gaagatgaaa cggcacaaat tccggctgaa gctgtcatcg gttactcaga tttagaaggg  8040
gatttcgatg ttgctgtttt gccattttcc aacagcacaa ataacgggtt attgtttata  8100
aatactacta ttgccagcat tgctgctaaa gaagaagggg tatctctcga gaaaagagag  8160
gctgaagctg gcccggaaac cctgtgtggt gcggaactgg tggatgctct gcaattcgtc  8220
tgtggtgacc gtggcttcta cttcaataaa ccgaccggct atggtagctc tagtcgtcgc  8280
gcgccgcaga ccggtattgt ggatgaatgc tgttttcgta gctgtgacct gcgtcgtctg  8340
gaaatgtatt gtgccccgct gaaaccggcg aaatcggcgt gagcatgcca aggcctcagg  8400
taccggccgg ccatttaaat acaggcccct tttcctttgt cgatatcatg taattagtta  8460
tgtcacgctt acattcacgc cctcctccca catccgctct aaccgaaaag gaaggagtta  8520
gacaacctga agtctaggtc cctatttatt tttttaata gttatgttag tattaagaac  8580
gttatttata tttcaaattt ttcttttttt tctgtacaaa cgcgtgtacg catgtaacat  8640
tatactgaaa accttgcttg agaaggtttt gggacgctcg aaggctttaa tttgcaagct  8700
ggatctaaca tccaaagacg aaaggttgaa tgaaaccttt ttgccatccg acatccacag  8760
gtccattctc acacataagt gccaaacgca acaggagggg atacactagc agcagaccgt  8820
tgcaaacgca ggacctccac tcctcttctc ctcaacaccc acttttgcca tcgaaaaacc  8880
agcccagtta ttgggcttga ttggagctcg ctcattccaa ttccttctat taggctacta  8940
acaccatgac tttattagcc tgtctatcct ggcccccctg gcgaggttca tgtttgttta  9000
tttccgaatg caacaagctc cgcattacac ccgaacatca ctccagatga gggctttctg  9060
agtgtggggt caaatagttt catgttcccc aaatggccca aaactgacag tttaaacgct  9120
gtcttggaac ctaatatgac aaaagcgtga tctcatccaa gatgaactaa gtttggttcg  9180
ttgaaatgct aacggccagt tggtcaaaaa gaaacttcca aaagtcggca taccgtttgt  9240
cttgtttggt attgattgac gaatgctcaa aaataatctc attaatgctt agcgcagtct  9300
ctctatcgct tctgaacccc ggtgcacctg tgccgaaacg caaatgggga aacacccgct  9360
ttttggatga ttatgcattg tctccacatt gtatgcttcc aagattctgg tgggaatact  9420
gctgatagcc taacgttcat gatcaaaatt taactgttct aacccctact tgacagcaat  9480
atataaacag aaggaagctg ccctgtctta aacctttttt tttatcatca ttattagctt  9540
actttcataa ttgcgactgg ttccaattga caagcttttg attttaacga cttttaacga  9600
caacttgaga agatcaaaaa acaactaatt attcgaaacg gaattcaaaa aatgcggcaa  9660
ttctctattg ttgctctgtt cgctactggc gctctcgccg ctccagtcaa cactacaaca  9720
gaagatgaaa cggcacaaat tccggctgaa gctgtcatcg gttactcaga tttagaaggg  9780
gatttcgatg ttgctgtttt gccattttcc aacagcacaa ataacgggtt attgtttata  9840
aatactacta ttgccagcat tgctgctaaa gaagaagggg tatctctcga gaaaagagag  9900
gctgaagctg gcccggaaac cctgtgtggt gcggaactgg tggatgctct gcaattcgtc  9960
tgtggtgacc gtggcttcta cttcaataaa ccgaccggct atggtagctc tagtcgtcgc  10020
gcgccgcaga ccggtattgt ggatgaatgc tgttttcgta gctgtgacct gcgtcgtctg  10080
gaaatgtatt gtgccccgct gaaaccggcg aaatcggcgt gagcatgcca aggcctcagg  10140
taccggccgg ccatttaaat acaggcccct tttcctttgt cgatatcatg taattagtta  10200
tgtcacgctt acattcacgc cctcctccca catccgctct aaccgaaaag gaaggagtta  10260
gacaacctga agtctaggtc cctatttatt tttttaata gttatgttag tattaagaac  10320
gttatttata tttcaaattt ttcttttttt tctgtacaaa cgcgtgtacg catgtaacat  10380
tatactgaaa accttgcttg agaaggtttt gggacgctcg aaggctttaa tttgcaagct  10440
ggatccgcgg ccgccttcca aactctcatg gattctcagg taataggtat tctaggagga  10500
ggccagctag gccgaatgat tgttgaggcc gctagcaggc tcaatatcaa gaccgtgatt  10560
cttgatgatg gtttttcacc tgctaagcac attaatgctg cgcaagacca catcgacgga  10620
tcattcaaag atgaggaggc tatcgccaag ttagctgcca aatgtgatgt tctcactgta  10680
```

-continued

```
gagattgagc atgtcaacac agatgctcta aagagagttc aagacagaac tggaatcaag  10740
atatatcctt taccagagac aatcgaacta atcaaggata agtacttgca aaaggaacat  10800
ttgatcaagc acaacatttc ggtgacaaag tctcagggta tagaatctaa tgaaaaggcg  10860
ctgcttttgt ttggagaaga gaatggattt ccatatctgt tgaagtcccg gactatggct  10920
tatgatggaa gaggcaattt tgtagtggag tctaaagagg acatcagtaa ggcattagag  10980
ttcttgaaag atcgtccatt gtatgccgag aagtttgctc cttttgttaa agaattagcg  11040
gtaatggttg tgagatcact ggaaggcgaa gtattctcct acccaaccgt agaaactgtg  11100
cacaaggaca atatctgtca tattgtgtat gctccggcca gagttaatga caccatccaa  11160
aagaaagctc aaatattagc tgaaaacact gtgaagactt tcccaggcgc tggaatcttc  11220
ggagttgaga tgttcctatt gtctgatgga gaacttcttg taaatgagat tgctccaagg  11280
ccccacaatt ctggtcacta tacaatcgat gcatgtgtaa catctcagtt cgaagcacat  11340
gtaagagcca taactggtct gccaatgcca ctagatttca ccaaactatc tacttccaac  11400
accaacgcta ttatgctcaa tgttttgggt gctgaaaaat ctcacgggga attagagttt  11460
tgtagaagag ccttagaaac acccggtgct tctgtatatc tgtacggaaa gaccacccga  11520
ttggctcgta agatgggtca tatcaacata ataggatctt ccatgttgga agcagaacaa  11580
aagttagagt acattctaga agaatcaacc cacttaccat ccagtactgt atcagctgac  11640
actaaaccgt tggttggagt tatcatgggt tcagactctg atctacctgt gatttcgaaa  11700
ggttgcgata ttttaaaaca gtttggtgtt ccattcgaag ttactattgt ctctgctcat  11760
agaacaccac agagaatgac cagatatgcc tttgaagccg ctagtagagg tatcaaggct  11820
atcattgcag gtgctggtgg tgctgctcat cttccaggaa tggttgctgc catgactccg  11880
ttgccagtca ttggtgttcc tgtcaagggc tctacgttgg atggtgtaga ctcgctacac  11940
tcgattgtcc aaatgcctag aggtgttcct gtggctacgg ttgctatcaa caacgccacc  12000
aatgccgctc tgttggccat caggatttta ggtacaattg accacaaatg gcaaaaggaa  12060
atgtccaagt atatgaatgc aatggagacc gaagtgttgg ggaaggcatc caacttggaa  12120
tctgaagggt atgaatccta tttgaagaat cgtctttgaa tttagtattg ttttttaata  12180
gatgtatata taatagtaca cgtaacttat ctattccatt cataatttta ttttaaaggt  12240
tcggtagaaa tttgtcctcc aaaaagttgg ttagagcctg gcagttttga taggcattat  12300
tatagattgg gtaatattta ccctgcacct ggaggaactt tgcaaagagc ctcatgtgcg  12360
gcgcgccagg ccataatggc caaacggttt ctcaattact atatactact aaccatttac  12420
ctgtagcgta tttcttttcc ctcttcgcga aagctcaagg gcatcttctt gactcatgaa  12480
aaatatctgg atttcttctg acagatcatc acccttgagc ccaactctct agcctatgag  12540
tgtaagtgat agtcatcttg caacagatta ttttggaacg caactaacaa agcagataca  12600
cccttcagca gaatcctttc tggatattgt gaagaatgat cgccaaagtc acagtcctga  12660
gacagttcct aatctttacc ccatttacaa gttcatccaa tcagacttct taacgcctca  12720
tctggcttat atcaagctta ccaacagttc agaaactccc agtccaagtt tcttgcttga  12780
aagtgcgaag aatggtgaca ccgttgacag gtacaccttt atgggacatt cccccagaaa  12840
aataatcaag actgggcctt tagagggtgc tgaagttgac cccttggtgc ttctggaaaa  12900
agaactgaag ggcaccagac aagcgcaact tcctggtatt cctcgtctaa gtggtggtgc  12960
cataggatac atctcgtacg attgtattaa gtactttgaa ccaaaaactg aaagaaaact  13020
gaaagatgtt ttgcaacttc cggaagcagc tttgatgttg ttcgacacga tcgtggcttt  13080
tgacaatgtt tatcaaagat tccaggtaat tggaaacgtt tctctatccg ttgatgactc  13140
ggacgaagct attcttgaga aatattataa gacaagagaa gaagtggaaa agatcagtaa  13200
agtggtattt gacaataaaa ctgttcccta ctatgaacag aaagatatta ttcaaggcca  13260
aacgttcacc tctaatattg gtcaggaagg gtatgaaaac catgttcgca agctgaaaga  13320
acatattctg aaaggagaca tcttccaagc tgttccctct caaagggtag ccaggccgac  13380
ctcattgcac cctttcaaca tctatcgtca tttgagaact gtcaatcctt ctccatacat  13440
gttctatatt gactatctag acttccaagt tgttggtgct tcacctgaat tactagttaa  13500
atccgacaac aacaacaaaa tcatcacaca tcctattgct ggaactcttc ccagaggtaa  13560
aactatcgaa gaggacgaca attatgctaa gcaattgaag tcgtctttga aagacagggc  13620
cgagcacgtc atgctggtag atttggccag aaatgatatt aaccgtgtgt gtgagcccac  13680
cagtaccacg gttgatcgtt tattgactgt ggagagattt tctcatgtga tgcatcttgt  13740
gtcagaagtc agtggaacat tgagaccaaa caagactcgc ttcgatgctt tcagatccat  13800
tttcccagca ggaaccgtct ccggtgctcc gaaggtaaga gcaatgcaac tcataggaga  13860
attggaagga gaaaagagag gtgtttatgc gggggccgta ggacactggt cgtacgatgg  13920
aaaatcgatg gacacatgta ttgccttaag aacaatggtc gtcaaggacg gtgtcgctta  13980
ccttcaagcc ggaggtggaa ttgtctacga ttctgacccc tatgacgagt acatcgaaac  14040
catgaacaaa atgagatcca acaataacac catcttggag gctgagaaaa tctggaccga  14100
taggttggcc agagacgaga atcaaagtga atccgaagaa aacgatcaat gaacggagga  14160
cgtaagtagg aatttatggt ttggccataa tggcctagct tggcgtaatc atggtcatag  14220
ctgtttcctg tgtgaaattg ttatccgctc acaattccac acaacatacg agccggaagc  14280
ataaagtgta aagcctgggg tgcctaatga gtgagctaac tcacattaat tgcgttgcgc  14340
tcactgcccg ctttccagtc gggaaacctg tcgtgccagc tgcattaatg aatcggccaa  14400
cgcgcgggga gaggcggttt gcgtattggg cgctcttccg cttcctcgct cactgactcg  14460
ctgcgctcgg tcgttcggct gcggcgagcg gtatcagctc actcaaaggc ggtaatacgg  14520
ttatccacag aatcagggga taacgcagga aagaacatgt gagcaaaagg ccagcaaaag  14580
gccaggaacc gtaaaaaggc cgcgttgctg gcgtttttcc ataggctccg cccccctgac  14640
gagcatcaca aaaatcgacg ctcaagtcag aggtggcgaa acccgacagg actataaaga  14700
taccaggcgt ttccccctgg aagctccctc gtgcgctctc ctgttccgac cctgccgctt  14760
accggatacc tgtccgcctt tctcccttcg ggaagcgtgg cgctttctca tagctcacgc  14820
tgtaggtatc tcagttcggt gtaggtcgtt cgctccaagc tgggctgtgt gcacgaaccc  14880
cccgttcagc ccgaccgctg cgccttatcc ggtaactatc gtcttgagtc caacccggta  14940
agacacgact tatcgccact ggcagcagcc actggtaaca ggattagcag agcgaggtat  15000
gtaggcggtg ctacagagtt cttgaagtgg tggcctaact acggctacac tagaaggaca  15060
gtatttggta tctgcgctct gctgaagcca gttaccttcg gaaaaagagt tggtagctct  15120
tgatccggca aacaaaccac cgctggtagc ggtggttttt ttgtttgcaa gcagcagatt  15180
acgcgcagaa aaaaaggatc tcaagaagat cctttgatct tttctacggg gtctgacgct  15240
cagtggaacg aaaactcacg ttaagggatt ttggtcatga gattatcaaa aaggatcttc  15300
acctagatcc ttttaaatta aaaatgaagt tttaaatcaa tctaaagtat atatgagtaa  15360
acttggtctg acagttacca atgcttaatc agtgaggcac ctatctcagc gatctgtcta  15420
```

```
tttcgttcat ccatagttgc ctgactcccc gtcgtgtaga taactacgat acgggagggc  15480
ttaccatctg gccccagtgc tgcaatgata ccgcgagacc cacgctcacc ggctccagat  15540
ttatcagcaa taaaccagcc agccggaagg gccgagcgca gaagtggtcc tgcaacttta  15600
tccgcctcca tccagtctat taattgttgc cgggaagcta gagtaagtag ttcgccagtt  15660
aatagtttgc gcaacgttgt tgccattgct acaggcatcg tggtgtcacg ctcgtcgttt  15720
ggtatggctt cattcagctc cggttcccaa cgatcaaggc gagttacatg atcccccatg  15780
ttgtgcaaaa aagcggttag ctccttcggt cctccgatcg ttgtcagaag taagttggcc  15840
gcagtgttat cactcatggt tatggcagca ctgcataatt ctcttactgt catgccatcc  15900
gtaagatgct tttctgtgac tggtgagtac tcaaccaagt cattctgaga atagtgtatg  15960
cggcgaccga gttgctcttg cccggcgtca atacgggata ataccgcgcc acatagcaga  16020
actttaaaag tgctcatcat tggaaaacgt tcttcggggc gaaaactctc aaggatctta  16080
ccgctgttga gatccagttc gatgtaaccc actcgtgcac ccaactgatc ttcagcatct  16140
tttactttca ccagcgtttc tgggtgagca aaaacaggaa ggcaaaatgc cgcaaaaaag  16200
ggaataaggg cgacacggaa atgttgaata ctcatactct tcctttttca atattattga  16260
agcatttatc agggttattg tctcatgagc ggatacatat ttgaatgtat ttagaaaaat  16320
aaacaaatag gggttccgcg cacatttccc cgaaaagtgc cacctgacgt ctaagaaacc  16380
attattatca tgacattaac ctataaaaat aggcgtatca cgaggccctt tcgtctcgcg  16440
cgtttcggtg atgacggtga aaacctctga cacatgcagc tcccggagac ggtcacagct  16500
tgtctgtaag cggatgccgg gagcagacaa gcccgtcagg gcgcgtcagc gggtgttggc  16560
gggtgtcggg gctggcttaa ctatgcggca tcagagcaga ttgtactgag agtgcaccat  16620
atgcggtgtg aaataccgca cagatgcgta aggagaaaat accgcatcag gcgccattcg  16680
ccattcaggc tgcgcaactg ttgggaaggg cgatcggtgc gggcctcttc gctattacgc  16740
cagctggcga aagggggatg tgctgcaagg cgattaagtt gggtaacgcc agggttttcc  16800
cagtcacgac gttgtaaaac gacggccagt gaattg                            16836

SEQ ID NO: 7           moltype = DNA  length = 8136
FEATURE                Location/Qualifiers
misc_feature           1..8136
                       note = pPinkHC-alphahIGF1
misc_feature           957
                       note = n is A, T, G, or C
source                 1..8136
                       mol_type = other DNA
                       organism = synthetic construct
SEQUENCE: 7
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcwama matgcgncag  960
ttctccatcg ttgccctctt cgctactggc gctctcgccg ctccagtcaa cactacaaca  1020
gaagatgaaa cggcacaaat tccggctgaa gctgtcatcg gttactcaga tttagaaggg  1080
gatttcgatg ttgctgtttt gccattttcc aacagcacaa ataacgggtt attgtttata  1140
aatactacta ttgccagcat tgctgctaaa gaagaagggg tatctctcga gaaaagagag  1200
gctgaagctg gcccggaaac cctgtgtggt gcggaactgg tggatgctct gcaattcgtc  1260
tgtggtgacc gtggcttcta cttcaataaa ccgaccggct atggtagctc tagtcgtcgc  1320
gcgccgcaga ccggtattgt ggatgaatgc tgttttcgta gctgtgacct gcgtcgtctg  1380
gaaatgtatt gtgccccgct gaaaccggcg aaatcggcgt gagcatgcca aggcctcagg  1440
taccggccgg ccatttaaat acaggcccct tttcctttgt cgatatcatg taattagtta  1500
tgtcacgctt acattcacgc cctcctccca catccgctct aaccgaaaag gaaggagtta  1560
gacaacctga agtctaggtc cctatttatt ttttttaata gttatgttag tattaagaac  1620
gttatttata tttcaaattt ttcttttttt tctgtacaaa cgcgtgtacg catgtaacat  1680
tatactgaaa accttgcttg agaaggtttt gggacgctcg aaggctttaa tttgcaagct  1740
ggatccgcgg ccgccttcca aactctcatg gattctcagg taataggtat tctaggagga  1800
ggccagctag gccgaatgat tgttgaggcc gctagcaggc tcaatatcaa gaccgtgatt  1860
cttgatgatg gtttttcacc tgctaagcac attaatgctg cgcaagacca catcgacgga  1920
tcattcaaag atgaggaggc tatcgccaag ttagctgcca aatgtgatgt tctcactgta  1980
gagattgagc atgtcaacac agatgctcta aagagagttc aagacagaac tggaatcaag  2040
atatatcctt taccagagac aatcgaacta atcaaggata agtacttgca aaaggaacat  2100
ttgatcaagc acaacatttc ggtgacaaag tctcagggta tagaatctaa tgaaaaggcg  2160
ctgcttttgt ttggagaaga gaatggattt ccatatctgt tgaagtcccg gactatggct  2220
tatgatggaa gaggcaattt tgtagtggag tctaaagagg acatcagtaa ggcattagag  2280
ttcttgaaag atcgtccatt gtatgccgag aagtttgctc cttttgttaa agaattagcg  2340
gtaatggttg tgagatcact ggaaggcgaa gtattctcct acccaaccgt agaaactgtg  2400
cacaaggaca atatctgtca tattgtgtat gctccggcca gagttaatga caccatccaa  2460
aagaaagctc aaatattagc tgaaaacact gtgaagactt tcccaggcgc tggaatcttc  2520
ggagttgaga tgttcctatt gtctgatgga gaacttcttg taaatgagat tgctccaagg  2580
ccccacaatt ctggtcacta tacaatcgat gcatgtgtaa catctcagtt cgaagcacat  2640
```

```
gtaagagcca taactggtct gccaatgcca ctagatttca ccaaactatc tacttccaac  2700
accaacgcta ttatgctcaa tgttttgggt gctgaaaaat ctcacgggga attagagttt  2760
tgtagaagag ccttagaaac acccggtgct tctgtatatc tgtacggaaa gaccacccga  2820
ttggctcgta agatgggtca tatcaacata ataggatctt ccatgttgga agcagaacaa  2880
aagttagagt acattctaga agaatcaacc cacttaccat ccagtactgt atcagctgac  2940
actaaaccgt tggttggagt tatcatgggt tcagactctg atctacctgt gatttcgaaa  3000
ggttgcgata ttttaaaaca gtttggtgtt ccattcgaag ttactattgt ctctgctcat  3060
agaacaccac agagaatgac cagatatgcc tttgaagccg ctagtagagg tatcaaggct  3120
atcattgcag gtgctggtgg tgctgctcat cttccaggaa tggttgctgc catgactccg  3180
ttgccagtca ttggtgttcc tgtcaagggc tctacgttgg atggtgtaga ctcgctacac  3240
tcgattgtcc aaatgcctag aggtgttcct gtggctacgg ttgctatcaa caacgccacc  3300
aatgccgctc tgttggccat caggatttta ggtacaattg accacaaatg gcaaaaggaa  3360
atgtccaagt atatgaatgc aatggagacc gaagtgttgg ggaaggcatc caacttggaa  3420
tctgaagggt atgaatccta tttgaagaat cgtctttgaa tttagtattg tttttttaata  3480
gatgtatata taatagtaca cgtaacttat ctattccatt cataatttta ttttaaaggt  3540
tcggtagaaa tttgtcctcc aaaaagttgg ttagagcctg gcagttttga taggcattat  3600
tatagattgg gtaatattta ccctgcacct ggaggaactt tgcaaagagc ctcatgtgcg  3660
gcgcgccagg ccataatggc caaacggttt ctcaattact atatactact aaccatttac  3720
ctgtagcgta tttcttttcc ctcttcgcga aagctcaagg gcatcttctt gactcatgaa  3780
aaatatctgg atttcttctg acagatcatc acccttgagc ccaactctct agcctatgag  3840
tgtaagtgat agtcatcttg caacagatta ttttggaacg caactaacaa agcagataca  3900
cccttcagca gaatcctttc tggatattgt gaagaatgat cgccaaagtc acagtcctga  3960
gacagttcct aatctttacc ccatttacaa gttcatccaa tcagacttct taacgcctca  4020
tctggcttat atcaagctta ccaacagttc agaaactccc agtccaagtt tcttgcttga  4080
aagtgcgaag aatggtgaca ccgttgacag gtacaccttt atgggacatt cccccagaaa  4140
aataatcaag actgggcctt tagagggtgc tgaagttgac cccttggtgc ttctggaaaa  4200
agaactgaag ggcaccagac aagcgcaact tcctggtatt cctcgtctaa gtggtggtgc  4260
cataggatac atctcgtacg attgtattaa gtactttgaa ccaaaaactg aaagaaaact  4320
gaaagatgtt ttgcaacttc cggaagcagc tttgatgttg ttcgacacga tcgtggcttt  4380
tgacaatgtt tatcaaagat tccaggtaat tggaaacgtt tctctatccg ttgatgactc  4440
ggacgaagct attcttgaga aatattataa gacaagagaa gaagtggaaa agatcagtaa  4500
agtggtattt gacaataaaa ctgttcccta ctatgaacag aaagatatta ttcaaggcca  4560
aacgttcacc tctaatattg gtcaggaagg gtatgaaaac catgttcgca agctgaaaga  4620
acatattctg aaaggagaca tcttccaagc tgttccctct caaagggtag ccaggccgac  4680
ctcattgcac cctttcaaca tctatcgtca tttgagaact gtcaatcctt ctccatacat  4740
gttctatatt gactatctag acttccaagt tgttggtgct tcacctgaat tactagttaa  4800
atccgacaac aacaacaaaa tcatcacaca tcctattgct ggaactcttc ccagaggtaa  4860
aactatcgaa gaggacgaca attatgctaa gcaattgaag tcgtctttga aagacagggc  4920
cgagcacgtc atgctggtag atttggccag aaatgatatt aaccgtgtgt gtgagcccac  4980
cagtaccacg gttgatcgtt tattgactgt ggagagattt tctcatgtga tgcatcttgt  5040
gtcagaagtc agtggaacat tgagaccaaa caagactcgc ttcgatgctt tcagatccat  5100
tttcccagca ggaaccgtct ccggtgctcc gaaggtaaga gcaatgcaac tcataggaga  5160
attggaagga gaaaagagag gtgtttatgc gggggccgta ggacactggt cgtacgatgg  5220
aaaatcgatg gacacatgta ttgccttaag aacaatggtc gtcaaggacg gtgtcgctta  5280
ccttcaagcc ggaggtggaa ttgtctacga ttctgacccc tatgacgagt acatcgaaac  5340
catgaacaaa atgagatcca acaataacac catcttggag gctgagaaaa tctggaccga  5400
taggttggcc agagacgaga atcaaagtga atccgaagaa aacgatcaat gaacggagga  5460
cgtaagtagg aatttatggt ttggccataa tggcctagct tggcgtaatc atggtcatag  5520
ctgtttcctg tgtgaaattg ttatccgctc acaattccac acaacatacg agccggaagc  5580
ataaagtgta aagcctgggg tgcctaatga gtgagctaac tcacattaat tgcgttgcgc  5640
tcactgcccg ctttccagtc gggaaacctg tcgtgccagc tgcattaatg aatcggccaa  5700
cgcgcgggga gaggcggttt gcgtattggg cgctcttccg cttcctcgct cactgactcg  5760
ctgcgctcgg tcgttcggct gcggcgagcg gtatcagctc actcaaaggc ggtaatacgg  5820
ttatccacag aatcagggga taacgcagga aagaacatgt gagcaaaagg ccagcaaaag  5880
gccaggaacc gtaaaaaggc cgcgttgctg gcgtttttcc ataggctccg cccccctgac  5940
gagcatcaca aaaatcgacg ctcaagtcag aggtggcgaa acccgacagg actataaaga  6000
taccaggcgt ttccccctgg aagctccctc gtgcgctctc ctgttccgac cctgccgctt  6060
accggatacc tgtccgcctt tctcccttcg ggaagcgtgg cgctttctca tagctcacgc  6120
tgtaggtatc tcagttcggt gtaggtcgtt cgctccaagc tgggctgtgt gcacgaaccc  6180
cccgttcagc ccgaccgctg cgccttatcc ggtaactatc gtcttgagtc caacccggta  6240
agacacgact tatcgccact ggcagcagcc actggtaaca ggattagcag agcgaggtat  6300
gtaggcggtg ctacagagtt cttgaagtgg tggcctaact acggctacac tagaaggaca  6360
gtatttggta tctgcgctct gctgaagcca gttaccttcg gaaaaagagt tggtagctct  6420
tgatccggca aacaaaccac cgctggtagc ggtggttttt ttgtttgcaa gcagcagatt  6480
acgcgcagaa aaaaaggatc tcaagaagat cctttgatct tttctacggg gtctgacgct  6540
cagtggaacg aaaactcacg ttaagggatt ttggtcatga gattatcaaa aaggatcttc  6600
acctagatcc ttttaaatta aaaatgaagt tttaaatcaa tctaaagtat atatgagtaa  6660
acttggtctg acagttacca atgcttaatc agtgaggcac ctatctcagc gatctgtcta  6720
tttcgttcat ccatagttgc ctgactcccc gtcgtgtaga taactacgat acgggagggc  6780
ttaccatctg gccccagtgc tgcaatgata ccgcgagacc cacgctcacc ggctccagat  6840
ttatcagcaa taaaccagcc agccggaagg gccgagcgca gaagtggtcc tgcaacttta  6900
tccgcctcca tccagtctat taattgttgc cgggaagcta gagtaagtag ttcgccagtt  6960
aatagtttgc gcaacgttgt tgccattgct acaggcatcg tggtgtcacg ctcgtcgttt  7020
ggtatggctt cattcagctc cggttcccaa cgatcaaggc gagttacatg atcccccatg  7080
ttgtgcaaaa aagcggttag ctccttcggt cctccgatcg ttgtcagaag taagttggcc  7140
gcagtgttat cactcatggt tatggcagca ctgcataatt ctcttactgt catgccatcc  7200
gtaagatgct tttctgtgac tggtgagtac tcaaccaagt cattctgaga atagtgtatg  7260
cggcgaccga gttgctcttg cccggcgtca atacgggata ataccgcgcc acatagcaga  7320
actttaaaag tgctcatcat tggaaaacgt tcttcggggc gaaaactctc aaggatctta  7380
```

```
ccgctgttga gatccagttc gatgtaaccc actcgtgcac ccaactgatc ttcagcatct  7440
tttactttca ccagcgtttc tgggtgagca aaaacaggaa ggcaaaatgc cgcaaaaaag  7500
ggaataaggg cgacacggaa atgttgaata ctcatactct tcctttttca atattattga  7560
agcatttatc agggttattg tctcatgagc ggatacatat ttgaatgtat ttagaaaaat  7620
aaacaaatag gggttccgcg cacatttccc cgaaaagtgc cacctgacgt ctaagaaacc  7680
attattatca tgacattaac ctataaaaat aggcgtatca cgaggccctt tcgtctcgcg  7740
cgtttcggtg atgacggtga aaacctctga cacatgcagc tcccggagac ggtcacagct  7800
tgtctgtaag cggatgccgg gagcagacaa gcccgtcagg gcgcgtcagc gggtgttggc  7860
gggtgtcggg gctggcttaa ctatgcggca tcagagcaga ttgtactgag agtgcaccat  7920
atgcggtgtg aaataccgca cagatgcgta aggagaaaat accgcatcag gcgccattcg  7980
ccattcaggc tgcgcaactg ttgggaaggg cgatcggtgc gggcctcttc gctattacgc  8040
cagctggcga aagggggatg tgctgcaagg cgattaagtt gggtaacgcc agggttttcc  8100
cagtcacgac gttgtaaaac gacggccagt gaattg                            8136

SEQ ID NO: 8           moltype = DNA  length = 16915
FEATURE                Location/Qualifiers
misc_feature           1..16915
                       note = pPinkHC-6XalphahIGF1
source                 1..16915
                       mol_type = other DNA
                       organism = synthetic construct
SEQUENCE: 8
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcatga gatttccttc  960
aatttttact gcagttttat tcgcagcatc ctccgcatta gctgctccag tcaacactac  1020
aacagaagat gaaacggcac aaattccggc tgaagctgtc atcggttact cagatttaga  1080
aggggatttc gatgttgctg ttttgccatt ttccaacagc acaaataacg ggttattgtt  1140
tataaatact actattgcca gcattgctgc taaagaagaa ggggtatctc tcgagaaaag  1200
agaggctgaa gctggcccgg aaaccctgtg tggtgcggaa ctggtggatg ctctgcaatt  1260
cgtctgtggt gaccgtggct tctacttcaa taaaccgacc ggctatggta gctctagtcg  1320
tcgcgcgccg cagaccggta ttgtggatga atgctgtttt cgtagctgtg acctgcgtcg  1380
tctggaaatg tattgtgccc cgctgaaacc ggcgaaatcg gcgtgagcat gccaaggcct  1440
caggtaccgg ccggccattt aaatacaggc ccccttttcct ttgtcgatat catgtaatta  1500
gttatgtcac gcttacattc acgccctcct cccacatccg ctctaaccga aaaggaagga  1560
gttagacaac ctgaagtcta ggtccctatt tattttttt aatagttatg ttagtattaa  1620
gaacgttatt tatatttcaa attttcttt tttttctgta caaacgcgtg tacgcatgta  1680
acattatact gaaaaccttg cttgagaagg ttttgggacg ctcgaaggct ttaatttgca  1740
agctggatcc aagctggatc taacatccaa agacgaaagg ttgaatgaaa cctttttgcc  1800
atccgacatc cacaggtcca ttctcacaca taagtgccaa acgcaacagg aggggataca  1860
ctagcagcag accgttgcaa acgcaggacc tccactcctc ttctcctcaa cacccacttt  1920
tgccatcgaa aaaccagccc agttattggg cttgattgga gctcgctcat tccaattcct  1980
tctattaggc tactaacacc atgactttat tagcctgtct atcctggccc ccctggcgag  2040
gttcatgttt gtttatttcc gaatgcaaca agctccgcat tacacccgaa catcactcca  2100
gatgagggct ttctgagtgt ggggtcaaat agtttcatgt tccccaaatg gcccaaaact  2160
gacagtttaa acgctgtctt ggaacctaat atgacaaaag cgtgatctca tccaagatga  2220
actaagtttg gttcgttgaa atgctaacgg ccagttggtc aaaaagaaac ttccaaaagt  2280
cggcataccg tttgtcttgt ttggtattga ttgacgaatg ctcaaaaata atctcattaa  2340
tgcttagcgc agtctctcta tcgcttctga accccggtgc acctgtgccg aaacgcaaat  2400
ggggaaacac ccgctttttg gatgattatg cattgtctcc acattgtatg cttccaagat  2460
tctggtggga atactgctga tagcctaacg ttcatgatca aaatttaact gttctaaccc  2520
ctacttgaca gcaatatata aacagaagga agctgccctg tcttaaacct ttttttttat  2580
catcattatt agcttacttt cataattgcg actggttcca attgacaagc ttttgatttt  2640
aacgactttt aacgacaact tgagaagatc aaaaaacaac taattattcg aaacggaatt  2700
catgagattt ccttcaattt ttactgcagt tttattcgca gcatcctccg cattagctgc  2760
tccagtcaac actacaacag aagatgaaac ggcacaaatt ccggctgaag ctgtcatcgg  2820
ttactcagat ttagaagggg atttcgatgt tgctgttttg ccattttcca acagcacaaa  2880
taacgggtta ttgtttataa atactactat tgccagcatt gctgctaaag aagaaggggt  2940
atctctcgag aaaagagagg ctgaagctgg cccggaaacc ctgtgtggtg cggaactggt  3000
ggatgctctg caattcgtct gtggtgaccg tggcttctac ttcaataaac cgaccggcta  3060
tggtagctct agtcgtcgcg cgccgcagac cggtattgtg gatgaatgct gttttcgtag  3120
ctgtgacctg cgtcgtctgg aaatgtattg tgccccgctg aaaccggcga aatcggcgtg  3180
agcatgccaa ggcctcaggt accggccggc catttaaata caggcccctt ttcctttgtc  3240
gatatcatgt aattagttat gtcacgctta cattcacgcc ctcctcccac atccgctcta  3300
accgaaaagg aaggagttag acaacctgaa gtctaggtcc ctatttattt tttttaatag  3360
ttatgttagt attaagaacg ttatttatat ttcaaatttt tctttttttt ctgtacaaac  3420
```

-continued

```
gcgtgtacgc atgtaacatt atactgaaaa ccttgcttga gaaggttttg ggacgctcga  3480
aggctttaat ttgcaagctg gatccaagct ggatctaaca tccaaagacg aaaggttgaa  3540
tgaaaccttt ttgccatccg acatccacag gtccattctc acacataagt gccaaacgca  3600
acaggagggg atacactagc agcagaccgt tgcaaacgca ggacctccac tcctcttctc  3660
ctcaacaccc acttttgcca tcgaaaaacc agcccagtta ttgggcttga ttggagctcg  3720
ctcattccaa ttccttctat taggctacta acaccatgac tttattagcc tgtctatcct  3780
ggccccccctg gcgaggttca tgtttgttta tttccgaatg caacaagctc cgcattacac  3840
ccgaacatca ctccagatga gggctttctg agtgtggggt caaatagttt catgttcccc  3900
aaatggccca aaactgacag tttaaacgct gtcttggaac ctaatatgac aaaagcgtga  3960
tctcatccaa gatgaactaa gtttggttcg ttgaaatgct aacggccagt tggtcaaaaa  4020
gaaacttcca aaagtcggca taccgtttgt cttgtttggt attgattgac gaatgctcaa  4080
aaataatctc attaatgctt agcgcagtct ctctatcgct tctgaacccc ggtgcacctg  4140
tgccgaaacg caaatgggga aacacccgct tttggatga ttatgcattg tctccacatt  4200
gtatgcttcc aagattctgg tgggaatact gctgatagcc taacgttcat gatcaaaatt  4260
taactgttct aacccctact tgacagcaat atataaacag aaggaagctg ccctgtctta  4320
aacctttttt tttatcatca ttattagctt actttcataa ttgcgactgg ttccaattga  4380
caagcttttg attttaacga cttttaacga caacttgaga agatcaaaaa acaactaatt  4440
attcgaaacg gaattcatga gatttccttc aatttttact gcagttttat tcgcagcatc  4500
ctccgcatta gctgctccag tcaacactac aacagaagat gaaacggcac aaattccggc  4560
tgaagctgtc atcggttact cagatttaga aggggatttc gatgttgctg ttttgccatt  4620
ttccaacagc acaaataacg ggttattgtt tataaatact actattgcca gcattgctgc  4680
taaagaagaa ggggtatctc tcgagaaaag agaggctgaa gctggcccgg aaaccctgtg  4740
tggtgcggaa ctggtggatg ctctgcaatt cgtctgtggt gaccgtggct tctacttcaa  4800
taaaccgacc ggctatggta gctctagtcg tcgcgcgccg cagaccggta ttgtggatga  4860
atgctgtttt cgtagctgtg acctgcgtcg tctggaaatg tattgtgccc cgctgaaacc  4920
ggcgaaatcg gcgtgagcat gccaaggcct caggtaccgg ccggccattt aaatacaggc  4980
cccttttcct ttgtcgatat catgtaatta gttatgtcac gcttacattc acgccctcct  5040
cccacatccg ctctaaccga aaaggaagga gttagacaac ctgaagtcta ggtccctatt  5100
tattttttt aatagttatg ttagtattaa gaacgttatt tatatttcaa atttttcttt  5160
tttttctgta caaacgcgtg tacgcatgta acattatact gaaaaccttg cttgagaagg  5220
ttttgggacg ctcgaaggct ttaatttgca agctggatcc aagctggatc taacatccaa  5280
agacgaaagg ttgaatgaaa cctttttgcc atccgacatc cacaggtcca ttctcacaca  5340
taagtgccaa acgcaacagg aggggataca ctagcagcag accgttgcaa acgcaggacc  5400
tccactcctc ttctcctcaa cacccacttt tgccatcgaa aaaccagccc agttattggg  5460
cttgattgga gctcgctcat tccaattcct tctattaggc tactaacacc atgactttat  5520
tagcctgtct atcctggccc ccctggcgag gttcatgttt gtttatttcc gaatgcaaca  5580
agctccgcat tacacccgaa catcactcca gatgagggct ttctgagtgt ggggtcaaat  5640
agtttcatgt tccccaaatg gcccaaaact gacagtttaa acgctgtctt ggaacctaat  5700
atgacaaaag cgtgatctca tccaagatga actaagtttg gttcgttgaa atgctaacgg  5760
ccagttggtc aaaaagaaac ttccaaaagt cggcataccg tttgtcttgt ttggtattga  5820
ttgacgaatg ctcaaaaata atctcattaa tgcttagcgc agtctctcta tcgcttctga  5880
accccggtgc acctgtgccg aaacgcaaat ggggaaacac ccgcttttg gatgattatg  5940
cattgtctcc acattgtatg cttccaagat tctggtggga atactgctga tagcctaacg  6000
ttcatgatca aaatttaact gttctaaccc ctacttgaca gcaatatata aacagaagga  6060
agctgccctg tcttaaacct tttttttat catcattatt agcttacttt cataattgcg  6120
actggttcca attgacaagc ttttgatttt aacgactttt aacgacaact tgagaagatc  6180
aaaaaacaac taattattcg aaacggaatt catgagattt ccttcaattt ttactgcagt  6240
tttattcgca gcatcctccg cattagctgc tccagtcaac actacaacag aagatgaaac  6300
ggcacaaatt ccggctgaag ctgtcatcgg ttactcagat ttagaagggg atttcgatgt  6360
tgctgttttg ccattttcca acagcacaaa taacgggtta ttgtttataa atactactat  6420
tgccagcatt gctgctaaag aagaaggggt atctctcgag aaaagagagg ctgaagctgg  6480
cccggaaacc ctgtgtggtg cggaactggt ggatgctctg caattcgtct gtggtgaccg  6540
tggcttctac ttcaataaac cgaccggcta tggtagctct agtcgtcgcg cgccgcagac  6600
cggtattgtg gatgaatgct gttttcgtag ctgtgacctg cgtcgtctgg aaatgtattg  6660
tgccccgctg aaaccggcga aatcggcgtg agcatgccaa ggcctcaggt accggccggc  6720
catttaaata caggcccctt ttcctttgtc gatatcatgt aattagttat gtcacgctta  6780
cattcacgcc ctcctcccac atccgctcta accgaaaagg aaggagttag acaacctgaa  6840
gtctaggtcc ctatttattt tttttaatag ttatgttagt attaagaacg ttatttatat  6900
ttcaaatttt tctttttttt ctgtacaaac gcgtgtacgc atgtaacatt atactgaaaa  6960
ccttgcttga gaaggttttg ggacgctcga aggctttaat ttgcaagctg gatccaagct  7020
ggatctaaca tccaaagacg aaaggttgaa tgaaaccttt ttgccatccg acatccacag  7080
gtccattctc acacataagt gccaaacgca acaggagggg atacactagc agcagaccgt  7140
tgcaaacgca ggacctccac tcctcttctc ctcaacaccc acttttgcca tcgaaaaacc  7200
agcccagtta ttgggcttga ttggagctcg ctcattccaa ttccttctat taggctacta  7260
acaccatgac tttattagcc tgtctatcct ggccccccctg gcgaggttca tgtttgttta  7320
tttccgaatg caacaagctc cgcattacac ccgaacatca ctccagatga gggctttctg  7380
agtgtggggt caaatagttt catgttcccc aaatggccca aaactgacag tttaaacgct  7440
gtcttggaac ctaatatgac aaaagcgtga tctcatccaa gatgaactaa gtttggttcg  7500
ttgaaatgct aacggccagt tggtcaaaaa gaaacttcca aaagtcggca taccgtttgt  7560
cttgtttggt attgattgac gaatgctcaa aaataatctc attaatgctt agcgcagtct  7620
ctctatcgct tctgaacccc ggtgcacctg tgccgaaacg caaatgggga aacacccgct  7680
tttggatga ttatgcattg tctccacatt gtatgcttcc aagattctgg tgggaatact  7740
gctgatagcc taacgttcat gatcaaaatt taactgttct aacccctact tgacagcaat  7800
atataaacag aaggaagctg ccctgtctta aacctttttt tttatcatca ttattagctt  7860
actttcataa ttgcgactgg ttccaattga caagcttttg attttaacga cttttaacga  7920
caacttgaga agatcaaaaa acaactaatt attcgaaacg gaattcatga gatttccttc  7980
aatttttact gcagttttat tcgcagcatc ctccgcatta gctgctccag tcaacactac  8040
aacagaagat gaaacggcac aaattccggc tgaagctgtc atcggttact cagatttaga  8100
aggggatttc gatgttgctg ttttgccatt ttccaacagc acaaataacg ggttattgtt  8160
```

-continued

```
tataaatact actattgcca gcattgctgc taaagaagaa ggggtatctc tcgagaaaag  8220
agaggctgaa gctggcccgg aaaccctgtg tggtgcggaa ctggtggatg ctctgcaatt  8280
cgtctgtggt gaccgtggct tctacttcaa taaaccgacc ggctatggta gctctagtcg  8340
tcgcgcgccg cagaccggta ttgtggatga atgctgtttt cgtagctgtg acctgcgtcg  8400
tctggaaatg tattgtgccc cgctgaaacc ggcgaaatcg gcgtgagcat gccaaggcct  8460
caggtaccgg ccggccattt aaatacaggc cccttttcct ttgtcgatat catgtaatta  8520
gttatgtcac gcttacattc acgccctcct cccacatccg ctctaaccga aaaggaagga  8580
gttagacaac ctgaagtcta ggtccctatt tattttttt aatagttatg ttagtattaa  8640
gaacgttatt tatatttcaa atttttcttt tttttctgta caaacgcgtg tacgcatgta  8700
acattatact gaaaaccttg cttgagaagg ttttgggacg ctcgaaggct ttaatttgca  8760
agctggatcc aagctggatc taacatccaa agacgaaagg ttgaatgaaa cctttttgcc  8820
atccgacatc cacaggtcca ttctcacaca taagtgccaa acgcaacagg aggggataca  8880
ctagcagcag accgttgcaa acgcaggacc tccactcctc ttctcctcaa cacccacttt  8940
tgccatcgaa aaaccagccc agttattggg cttgattgga gctcgctcat tccaattcct  9000
tctattaggc tactaacacc atgactttat tagcctgtct atcctggccc ccctggcgag  9060
gttcatgttt gtttatttcc gaatgcaaca agctccgcat tacacccgaa catcactcca  9120
gatgagggct ttctgagtgt ggggtcaaat agtttcatgt tccccaaatg gcccaaaact  9180
gacagtttaa acgctgtctt ggaacctaat atgacaaaag cgtgatctca tccaagatga  9240
actaagtttg gttcgttgaa atgctaacgg ccagttggtc aaaaagaaac ttccaaaagt  9300
cggcataccg tttgtcttgt ttggtattga ttgacgaatg ctcaaaaata atctcattaa  9360
tgcttagcgc agtctctcta tcgcttctga accccggtgc acctgtgccg aaacgcaaat  9420
ggggaaacac ccgctttttg gatgattatg cattgtctcc acattgtatg cttccaagat  9480
tctggtggga atactgctga tagcctaacg ttcatgatca aaatttaact gttctaaccc  9540
ctacttgaca gcaatatata aacagaagga agctgccctg tcttaaacct tttttttat  9600
catcattatt agcttacttt cataattgcg actggttcca attgacaagc ttttgatttt  9660
aacgactttt aacgacaact tgagaagatc aaaaaacaac taattattcg aaacggaatt  9720
catgagattt ccttcaattt ttactgcagt tttattcgca gcatcctccg cattagctgc  9780
tccagtcaac actacaacag aagatgaaac ggcacaaatt ccggctgaag ctgtcatcgg  9840
ttactcagat ttagaagggg atttcgatgt tgctgttttg ccattttcca acagcacaaa  9900
taacgggtta ttgtttataa atactactat tgccagcatt gctgctaaag aagaaggggt  9960
atctctcgag aaaagagagg ctgaagctgg cccggaaacc ctgtgtggtg cggaactggt  10020
ggatgctctg caattcgtct gtggtgaccg tggcttctac ttcaataaac cgaccggcta  10080
tggtagctct agtcgtcgcg cgccgcagac cggtattgtg gatgaatgct gttttcgtag  10140
ctgtgacctg cgtcgtctgg aaatgtattg tgccccgctg aaaccggcga aatcggcgtg  10200
agcatgccaa ggcctcaggt accggccggc catttaaata caggcccctt ttcctttgtc  10260
gatatcatgt aattagttat gtcacgctta cattcacgcc ctcctcccac atccgctcta  10320
accgaaaagg aaggagttag acaacctgaa gtctaggtcc ctatttattt tttttaatag  10380
ttatgttagt attaagaacg ttatttatat ttcaaatttt tcttttttt ctgtacaaac  10440
gcgtgtacgc atgtaacatt atactgaaaa ccttgcttga gaaggttttg ggacgctcga  10500
aggctttaat ttgcaagctg gatccgcggc cgccttccaa actctcatgg attctcaggt  10560
aataggtatt ctaggaggag gccagctagg ccgaatgatt gttgaggccg ctagcaggct  10620
caatatcaag accgtgattc ttgatgatgg tttttcacct gctaagcaca ttaatgctgc  10680
gcaagaccac atcgacggat cattcaaaga tgaggaggct atcgccaagt tagctgccaa  10740
atgtgatgtt ctcactgtag agattgagca tgtcaacaca gatgctctaa agagagttca  10800
agacagaact ggaatcaaga tatatccttt accagagaca atcgaactaa tcaaggataa  10860
gtacttgcaa aaggaacatt tgatcaagca caacatttcg gtgacaaagt ctcagggtat  10920
agaatctaat gaaaaggcgc tgcttttgtt tggagaagag aatggatttc catatctgtt  10980
gaagtcccgg actatggctt atgatggaag aggcaatttt gtagtggagt ctaaagagga  11040
catcagtaag gcattagagt tcttgaaaga tcgtccattg tatgccgaga agtttgctcc  11100
ttttgttaaa gaattagcgg taatggttgt gagatcactg gaaggcgaag tattctccta  11160
cccaaccgta gaaactgtgc acaaggacaa tatctgtcat attgtgtatg ctccggccag  11220
agttaatgac accatccaaa agaaagctca aatattagct gaaaacactg tgaagacttt  11280
cccaggcgct ggaatcttcg gagttgagat gttcctattg tctgatggag aacttcttgt  11340
aaatgagatt gctccaaggc cccacaattc tggtcactat acaatcgatg catgtgtaac  11400
atctcagttc gaagcacatg taagagccat aactggtctg ccaatgccac tagatttcac  11460
caaactatct acttccaaca ccaacgctat tatgctcaat gttttgggtg ctgaaaaatc  11520
tcacggggaa ttagagtttt gtagaagagc cttagaaaca cccggtgctt ctgtatatct  11580
gtacggaaag accacccgat tggctcgtaa gatgggtcat atcaacataa taggatcttc  11640
catgttggaa gcagaacaaa agttagagta cattctagaa gaatcaaccc acttaccatc  11700
cagtactgta tcagctgaca ctaaaccgtt ggttggagtt atcatgggtt cagactctga  11760
tctacctgtg atttcgaaag gttgcgatat tttaaaacag tttggtgttc cattcgaagt  11820
tactattgtc tctgctcata gaacaccaca gagaatgacc agatatgcct ttgaagccgc  11880
tagtagaggt atcaaggcta tcattgcagg tgctggtggt gctgctcatc ttccaggaat  11940
ggttgctgcc atgactccgt tgccagtcat tggtgttcct gtcaagggct ctacgttgga  12000
tggtgtagac tcgctacact cgattgtcca aatgcctaga ggtgttcctg tggctacggt  12060
tgctatcaac aacgccacca atgccgctct gttggccatc aggattttag gtacaattga  12120
ccacaaatgg caaaaggaaa tgtccaagta tatgaatgca atggagaccg aagtgttggg  12180
gaaggcatcc aacttggaat ctgaagggta tgaatcctat ttgaagaatc gtctttgaat  12240
ttagtattgt tttttaatag atgtatatat aatagtacac gtaacttatc tattccattc  12300
ataattttat tttaaaggtt cggtagaaat ttgtcctcca aaaagttggt tagagcctgg  12360
cagttttgat aggcattatt atagattggg taatatttac cctgcacctg gaggaacttt  12420
gcaaagagcc tcatgtgcgg cgcgccaggc cataatggcc aaacggtttc tcaattacta  12480
tatactacta accatttacc tgtagcgtat ttcttttccc tcttcgcgaa agctcaaggg  12540
catcttcttg actcatgaaa aatatctgga tttcttctga cagatcatca cccttgagcc  12600
caactctcta gcctatgagt gtaagtgata gtcatcttgc aacagattat tttggaacgc  12660
aactaacaaa gcagatacac ccttcagcag aatcctttct ggatattgtg aagaatgatc  12720
gccaaagtca cagtcctgag acagttccta atctttaccc catttacaag ttcatccaat  12780
cagacttctt aacgcctcat ctggcttata tcaagcttac caacagttca gaaactccca  12840
gtccaagttt cttgcttgaa agtgcgaaga atggtgacac cgttgacagg tacaccttta  12900
```

```
tgggacattc ccccagaaaa ataatcaaga ctgggccttt agagggtgct gaagttgacc  12960
ccttggtgct tctggaaaaa gaactgaagg gcaccagaca agcgcaactt cctggtattc  13020
ctcgtctaag tggtggtgcc ataggataca tctcgtacga ttgtattaag tactttgaac  13080
caaaaactga aagaaaactg aaagatgttt tgcaacttcc ggaagcagct ttgatgttgt  13140
tcgacacgat cgtggctttt gacaatgttt atcaaagatt ccaggtaatt ggaaacgttt  13200
ctctatccgt tgatgactcg gacgaagcta ttcttgagaa atattataag acaagagaag  13260
aagtggaaaa gatcagtaaa gtggtatttg acaataaaac tgttccctac tatgaacaga  13320
aagatattat tcaaggccaa acgttcacct ctaatattgg tcaggaaggg tatgaaaacc  13380
atgttcgcaa gctgaaagaa catattctga aaggagacat cttccaagct gttccctctc  13440
aaagggtagc caggccgacc tcattgcacc ctttcaacat ctatcgtcat ttgagaactg  13500
tcaatccttc tccatacatg ttctatattg actatctaga cttccaagtt gttggtgctt  13560
cacctgaatt actagttaaa tccgacaaca acaacaaaat catcacacat cctattgctg  13620
gaactcttcc cagaggtaaa actatcgaag aggacgacaa ttatgctaag caattgaagt  13680
cgtctttgaa agacagggcc gagcacgtca tgctggtaga tttggccaga aatgatatta  13740
accgtgtgtg tgagcccacc agtaccacgg ttgatcgttt attgactgtg gagagatttt  13800
ctcatgtgat gcatcttgtg tcagaagtca gtggaacatt gagaccaaac aagactcgct  13860
tcgatgcttt cagatccatt ttcccagcag gaaccgtctc cggtgctccg aaggtaagag  13920
caatgcaact cataggagaa ttggaaggag aaaagagagg tgtttatgcg ggggccgtag  13980
gacactggtc gtacgatgga aaatcgatgg acacatgtat tgccttaaga acaatggtcg  14040
tcaaggacgg tgtcgcttac cttcaagccg gaggtggaat tgtctacgat tctgacccct  14100
atgacgagta catcgaaacc atgaacaaaa tgagatccaa caataacacc atcttggagg  14160
ctgagaaaat ctggaccgat aggttggcca gagacgagaa tcaaagtgaa tccgaagaaa  14220
acgatcaatg aacggaggac gtaagtagga atttatggtt tggccataat ggcctagctt  14280
ggcgtaatca tggtcatagc tgtttcctgt gtgaaattgt tatccgctca caattccaca  14340
caacatacga gccggaagca taaagtgtaa agcctggggt gcctaatgag tgagctaact  14400
cacattaatt gcgttgcgct cactgcccgc tttccagtcg ggaaacctgt cgtgccagct  14460
gcattaatga atcggccaac gcgcggggag aggcggtttg cgtattgggc gctcttccgc  14520
ttcctcgctc actgactcgc tgcgctcggt cgttcggctg cggcgagcgg tatcagctca  14580
ctcaaaggcg gtaatacggt tatccacaga atcaggggat aacgcaggaa agaacatgtg  14640
agcaaaaggc cagcaaaagg ccaggaaccg taaaaaggcc gcgttgctgg cgtttttcca  14700
taggctccgc ccccctgacg agcatcacaa aaatcgacgc tcaagtcaga ggtggcgaaa  14760
cccgacagga ctataaagat accaggcgtt tccccctgga agctccctcg tgcgctctcc  14820
tgttccgacc ctgccgctta ccggatacct gtccgccttt ctcccttcgg gaagcgtggc  14880
gctttctcat agctcacgct gtaggtatct cagttcggtg taggtcgttc gctccaagct  14940
gggctgtgtg cacgaacccc ccgttcagcc cgaccgctgc gccttatccg gtaactatcg  15000
tcttgagtcc aacccggtaa gacacgactt atcgccactg gcagcagcca ctggtaacag  15060
gattagcaga gcgaggtatg taggcggtgc tacagagttc ttgaagtggt ggcctaacta  15120
cggctacact agaaggacag tatttggtat ctgcgctctg ctgaagccag ttaccttcgg  15180
aaaaagagtt ggtagctctt gatccggcaa acaaaccacc gctggtagcg gtggtttttt  15240
tgtttgcaag cagcagatta cgcgcagaaa aaaaggatct caagaagatc ctttgatctt  15300
ttctacgggg tctgacgctc agtggaacga aaactcacgt taagggattt tggtcatgag  15360
attatcaaaa aggatcttca cctagatcct tttaaattaa aaatgaagtt ttaaatcaat  15420
ctaaagtata tatgagtaaa cttggtctga cagttaccaa tgcttaatca gtgaggcacc  15480
tatctcagcg atctgtctat ttcgttcatc catagttgcc tgactccccg tcgtgtagat  15540
aactacgata cgggagggct taccatctgg ccccagtgct gcaatgatac cgcgagaccc  15600
acgctcaccg gctccagatt tatcagcaat aaaccagcca gccggaaggg ccgagcgcag  15660
aagtggtcct gcaactttat ccgcctccat ccagtctatt aattgttgcc gggaagctag  15720
agtaagtagt tcgccagtta atagtttgcg caacgttgtt gccattgcta caggcatcgt  15780
ggtgtcacgc tcgtcgtttg gtatggcttc attcagctcc ggttcccaac gatcaaggcg  15840
agttacatga tcccccatgt tgtgcaaaaa agcggttagc tccttcggtc ctccgatcgt  15900
tgtcagaagt aagttggccg cagtgttatc actcatggtt atggcagcac tgcataattc  15960
tcttactgtc atgccatccg taagatgctt ttctgtgact ggtgagtact caaccaagtc  16020
attctgagaa tagtgtatgc ggcgaccgag ttgctcttgc ccggcgtcaa tacgggataa  16080
taccgcgcca catagcagaa ctttaaaagt gctcatcatt ggaaaacgtt cttcggggcg  16140
aaaactctca aggatcttac cgctgttgag atccagttcg atgtaaccca ctcgtgcacc  16200
caactgatct tcagcatctt ttactttcac cagcgtttct gggtgagcaa aaacaggaag  16260
gcaaaatgcc gcaaaaaagg gaataagggc gacacggaaa tgttgaatac tcatactctt  16320
cctttttcaa tattattgaa gcatttatca gggttattgt ctcatgagcg gatacatatt  16380
tgaatgtatt tagaaaaata aacaaatagg ggttccgcgc acatttcccc gaaaagtgcc  16440
acctgacgtc taagaaacca ttattatcat gacattaacc tataaaaata ggcgtatcac  16500
gaggcccttt cgtctcgcgc gtttcggtga tgacggtgaa aacctctgac acatgcagct  16560
cccggagacg gtcacagctt gtctgtaagc ggatgccggg agcagacaag cccgtcaggg  16620
cgcgtcagcg ggtgttggcg ggtgtcgggg ctggcttaac tatgcggcat cagagcagat  16680
tgtactgaga gtgcaccata tgcggtgtga aataccgcac agatgcgtaa ggagaaaata  16740
ccgcatcagg cgccattcgc cattcaggct gcgcaactgt tgggaagggc gatcggtgcg  16800
ggcctcttcg ctattacgcc agctggcgaa agggggatgt gctgcaaggc gattaagttg  16860
ggtaacgcca gggttttccc agtcacgacg ttgtaaaacg acggccagtg aattg       16915

SEQ ID NO: 9             moltype = DNA  length = 8100
FEATURE                  Location/Qualifiers
misc_feature             1..8100
                         note = pPinkHC-scvSrh(R)1-alphapro-GR-hIGF1
source                   1..8100
                         mol_type = other DNA
                         organism = synthetic construct
SEQUENCE: 9
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc actttgccca tcgaaaaacc  180
```

```
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcaaaa aatgcgacag  960
ttctccatcg ttgccctctt cgctactggc gctctcgccg ctccagtcaa cactacaaca  1020
gaagatgaaa cggcacaaat tccggctgaa gctgtcatcg gttactcaga tttagaaggg  1080
gatttcgatg ttgctgtttt gccattttcc gccagcattg ctgctaaaga agaaggggta  1140
tctctcgaga aaagagaggc tgaagctggt cggggcccgg aaaccctgtg tggtgcggaa  1200
ctggtggatg ctctgcaatt cgtctgtggt gaccgtggct tctacttcaa taaaccgacc  1260
ggctatggta gctctagtcg tcgcgcgccg cagaccggta ttgtggatga atgctgtttt  1320
cgtagctgtg acctgcgtcg tctggaaatg tattgtgccc cgctgaaacc ggcgaaatcg  1380
gcgtgagcat gccaaggcct caggtaccgg ccggccattt aaatacaggc ccctttttcct  1440
ttgtcgatat catgtaatta gttatgtcac gcttacattc acgccctcct cccacatccg  1500
ctctaaccga aaggaaggga gttagacaac ctgaagtcta ggtccctatt tattttttt  1560
aatagttatg ttagtattaa gaacgttatt tatatttcaa atttttcttt ttttctgta  1620
caaacgcgtg tacgcatgta acattatact gaaaaccttg cttgagaagg ttttgggacg  1680
ctcgaaggct ttaatttgca agctggatcc gcggccgcct tccaaactct catggattct  1740
caggtaatag gtattctagg aggaggccag ctaggccgaa tgattgttga ggccgctagc  1800
aggctcaata tcaagaccgt gattcttgat gatggttttt cacctgctaa gcacattaat  1860
gctgcgcaag accacatcga cggatcattc aaagatgagg aggctatcgc caagttagct  1920
gccaaatgtg atgttctcac tgtagagatt gagcatgtca acacagatgc tctaaagaga  1980
gttcaagaca gaactggaat caagatatat cctttaccag agacaatcga actaatcaag  2040
gataagtact tgcaaaagga acatttgatc aagcacaaca tttcggtgac aaagtctcag  2100
ggtatagaat ctaatgaaaa ggcgctgctt ttgtttggag aagagaatgg atttccatat  2160
ctgttgaagt cccggactat ggcttatgat ggaagaggca attttgtagt ggagtctaaa  2220
gaggacatca gtaaggcatt agagttcttg aaagatcgtc cattgtatgc cgagaagttt  2280
gctcoctttg ttaaagaatt agcggtaatg gttgtgagat cactggaagg cgaagtattc  2340
tcctacccaa ccgtagaaac tgtgcacaag gacaatatct gtcatattgt gtatgctccg  2400
gccagagtta atgacaccat ccaaaagaaa gctcaaatat tagctgaaaa cactgtgaag  2460
actttcccag gcgctggaat cttcggagtt gagatgttcc tattgtctga tggagaactt  2520
cttgtaaatg agattgctcc aaggccccac aattctggtc actatacaat cgatgcatgt  2580
gtaacatctc agttcgaagc acatgtaaga gccataactg gtctgccaat gccactagat  2640
ttcaccaaac tatctacttc caacaccaac gctattatgc tcaatgtttt gggtgctgaa  2700
aaatctcacg gggaattaga gttttgtaga agagccttag aaacacccgg tgcttctgta  2760
tatctgtacg gaaagaccac ccgattggct cgtaagatgg gtcatatcaa cataatagga  2820
tcttccatgt tggaagcaga acaaaagtta gagtacattc tagaagaatc aacccactta  2880
ccatccagta ctgtatcagc tgacactaaa ccgttggttg gagttatcat gggttcagac  2940
tctgatctac ctgtgatttc gaaaggttgc gatattttaa aacagtttgg tgttccattc  3000
gaagttacta ttgtctctgc tcatagaaca cccacagagaa tgaccagata tgcctttgaa  3060
gccgctagta gaggtatcaa ggctatcatt gcaggtgctg gtggtgctgc tcatcttcca  3120
ggaatggttg ctgccatgac tccgttgcca gtcattggtg ttcctgtcaa gggctctacg  3180
ttggatggtg tagactcgct acactcgatt gtccaaatgc ctagaggtgt tcctgtggct  3240
acggttgcta tcaacaacgc caccaatgcc gctctgttgg ccatcaggat tttaggtaca  3300
attgaccaca aatggcaaaa ggaaatgtcc aagtatatga atgcaatgga gaccgaagtg  3360
ttggggaagg catccaactt ggaatctgaa gggtatgaat cctatttgaa gaatcgtctt  3420
tgaatttagt attgtttttt aatagatgta tatataatag tacacgtaac ttatctattc  3480
cattcataat tttattttaa aggttcggta gaaatttgtc ctccaaaaag ttggttagag  3540
cctggcagtt ttgataggca ttattataga ttgggtaata tttaccctgc acctggagga  3600
actttgcaaa gagcctcatg tgcggcgcgc caggccataa tggccaaacg gtttctcaat  3660
tactatatac tactaaccat ttacctgtag cgtatttctt ttccctcttc gcgaaagctc  3720
aagggcatct tcttgactca tgaaaaatat ctggatttct tctgacagat catcacccctt  3780
gagcccaact ctctagccta tgagtgtaag tgatagtcat cttgcaacag attattttgg  3840
aacgcaacta acaaagcaga tacacccttc agcagaatcc tttctggata ttgtgaagaa  3900
tgatcgccaa agtcacagtc ctgagacagt tcctaatctt taccccattt acaagttcat  3960
ccaatcagac ttcttaacgc ctcatctggc ttatatcaag cttaccaaca gttcagaaac  4020
tcccagtcca agtttcttgc ttgaaagtgc gaagaatggt gacaccgttg acaggtacac  4080
ctttatggga cattccccca gaaaaataat caagactggg cctttagagg gtgctgaagt  4140
tgacccccttg gtgcttctgg aaaaagaact gaagggcacc agacaagcgc aacttcctgg  4200
tattcctcgt ctaagtggtg gtgccatagg atacatctcg tacgattgta ttaagtactt  4260
tgaaccaaaa actgaaagaa aactgaaaga tgttttgcaa cttccggaag cagctttgat  4320
gttgttcgac acgatcgtgg cttttgacaa tgtttatcaa agattccagg taattggaaa  4380
cgtttctcta tccgttgatg actcggacga agctattctt gagaaatatt ataagacaag  4440
agaagaagtg gaaaagatca gtaaagtggt atttgacaat aaaactgttc cctactatga  4500
acagaaagat attattcaag gccaaacgtt cacctctaat attggtcagg aagggtatga  4560
aaaccatgtt cgcaagctga aagaacatat tctgaaagga gacatcttcc aagctgttcc  4620
ctctcaaagg gtagccaggc cgacctcatt gcaccctttc aacatctatc gtcatttgag  4680
aactgtcaat ccttctccat acatgttcta tattgactat ctagacttcc aagttgttgg  4740
tgcttcacct gaattactag ttaaatccga caacaacaac aaaatcatca cacatcctat  4800
tgctggaact cttcccagag gtaaaactat cgaagaggac gacaattatg ctaagcaatt  4860
gaagtcgtct ttgaaagaca gggccgagca cgtcatgctg gtagatttgg ccagaaatga  4920
```

```
tattaaccgt gtgtgtgagc ccaccagtac cacggttgat cgtttattga ctgtggagag  4980
attttctcat gtgatgcatc ttgtgtcaga agtcagtgga acattgagac caaacaagac  5040
tcgcttcgat gctttcagat ccattttccc agcaggaacc gtctccggtg ctccgaaggt  5100
aagagcaatg caactcatag gagaattgga aggagaaaag agaggtgttt atgcgggggc  5160
cgtaggacac tggtcgtacg atggaaaatc gatggacaca tgtattgcct taagaacaat  5220
ggtcgtcaag gacggtgtcg cttaccttca agccggaggt ggaattgtct acgattctga  5280
cccctatgac gagtacatcg aaaccatgaa caaaatgaga tccaacaata acaccatctt  5340
ggaggctgag aaaatctgga ccgataggtt ggccagagac gagaatcaaa gtgaatccga  5400
agaaaacgat caatgaacgg aggacgtaag taggaattta tggtttggcc ataatggcct  5460
agcttggcgt aatcatggtc atagctgttt cctgtgtgaa attgttatcc gctcacaatt  5520
ccacacaaca tacgagccgg aagcataaag tgtaaagcct ggggtgccta atgagtgagc  5580
taactcacat taattgcgtt gcgctcactg cccgctttcc agtcgggaaa cctgtcgtgc  5640
cagctgcatt aatgaatcgg ccaacgcgcg gggagaggcg gtttgcgtat tgggcgctct  5700
tccgcttcct cgctcactga ctcgctgcgc tcggtcgttc ggctgcggcg agcggtatca  5760
gctcactcaa aggcggtaat acggttatcc acagaatcag gggataacgc aggaaagaac  5820
atgtgagcaa aaggccagca aaaggccagg aaccgtaaaa aggccgcgtt gctggcgttt  5880
ttccataggc tccgcccccc tgacgagcat cacaaaaatc gacgctcaag tcagaggtgg  5940
cgaaacccga caggactata aagataccag gcgtttcccc ctggaagctc cctcgtgcgc  6000
tctcctgttc cgaccctgcc gcttaccgga tacctgtccg cctttctccc ttcgggaagc  6060
gtggcgcttt ctcatagctc acgctgtagg tatctcagtt cggtgtaggt cgttcgctcc  6120
aagctgggct gtgtgcacga accccccgtt cagcccgacc gctgcgcctt atccggtaac  6180
tatcgtcttg agtccaaccc ggtaagacac gacttatcgc cactggcagc agccactggt  6240
aacaggatta gcagagcgag gtatgtaggc ggtgctacag agttcttgaa gtggtggcct  6300
aactacggct acactagaag gacagtattt ggtatctgcg ctctgctgaa gccagttacc  6360
ttcggaaaaa gagttggtag ctcttgatcc ggcaaacaaa ccaccgctgg tagcggtggt  6420
ttttttgttt gcaagcagca gattacgcgc agaaaaaaag gatctcaaga agatcctttg  6480
atcttttcta cggggtctga cgctcagtgg aacgaaaact cacgttaagg gattttggtc  6540
atgagattat caaaaaggat cttcacctag atccttttaa attaaaaatg aagttttaaa  6600
tcaatctaaa gtatatatga gtaaacttgg tctgacagtt accaatgctt aatcagtgag  6660
gcacctatct cagcgatctg tctatttcgt tcatccatag ttgcctgact ccccgtcgtg  6720
tagataacta cgatacggga gggcttacca tctggcccca gtgctgcaat gataccgcga  6780
gacccacgct caccggctcc agatttatca gcaataaacc agccagccgg aagggccgag  6840
cgcagaagtg gtcctgcaac tttatccgcc tccatccagt ctattaattg ttgccgggaa  6900
gctagagtaa gtagttcgcc agttaatagt ttgcgcaacg ttgttgccat tgctacaggc  6960
atcgtggtgt cacgctcgtc gtttggtatg gcttcattca gctccggttc ccaacgatca  7020
aggcgagtta catgatcccc catgttgtgc aaaaaagcgg ttagctcctt cggtcctccg  7080
atcgttgtca gaagtaagtt ggccgcagtg ttatcactca tggttatggc agcactgcat  7140
aattctctta ctgtcatgcc atccgtaaga tgcttttctg tgactggtga gtactcaacc  7200
aagtcattct gagaatagtg tatgcggcga ccgagttgct cttgcccggc gtcaatacgg  7260
gataataccg cgccacatag cagaacttta aaagtgctca tcattggaaa acgttcttcg  7320
gggcgaaaac tctcaaggat cttaccgctg ttgagatcca gttcgatgta acccactcgt  7380
gcacccaact gatcttcagc atcttttact ttcaccagcg tttctgggtg agcaaaaaca  7440
ggaaggcaaa atgccgcaaa aaagggaata agggcgacac ggaaatgttg aatactcata  7500
ctcttccttt ttcaatatta ttgaagcatt tatcagggtt attgtctcat gagcggatac  7560
atatttgaat gtatttagaa aaataaacaa ataggggttc cgcgcacatt tccccgaaaa  7620
gtgccacctg acgtctaaga aaccattatt atcatgacat taacctataa aaataggcgt  7680
atcacgaggc cctttcgtct cgcgcgtttc ggtgatgacg gtgaaaacct ctgacacatg  7740
cagctcccgg agacggtcac agcttgtctg taagcggatg ccgggagcag acaagcccgt  7800
cagggcgcgt cagcgggtgt tggcgggtgt cggggctggc ttaactatgc ggcatcagag  7860
cagattgtac tgagagtgca ccatatgcgg tgtgaaatac cgcacagatg cgtaaggaga  7920
aaataccgca tcaggcgcca ttcgccattc aggctgcgca actgttggga agggcgatcg  7980
gtgcgggcct cttcgctatt acgccagctg gcgaaagggg gatgtgctgc aaggcgatta  8040
agttgggtaa cgccagggtt ttcccagtca cgacgttgta aaacgacggc cagtgaattg  8100
```

```
SEQ ID NO: 10          moltype = DNA  length = 8097
FEATURE                Location/Qualifiers
misc_feature           1..8097
                       note = pPinkHC-scvSrh(R)1-alphapro-N-hIGF1
source                 1..8097
                       mol_type = other DNA
                       organism = synthetic construct
SEQUENCE: 10
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcaaaa aatgcgacag  960
ttctccatcg ttgccctctt cgctactggc gctctcgccg ctccagtcaa cactacaaca  1020
```

-continued

```
gaagatgaaa cggcacaaat tccggctgaa gctgtcatcg gttactcaga tttagaaggg  1080
gatttcgatg ttgctgtttt gccattttcc gccagcattg ctgctaaaga agaaggggta  1140
tctctcgaga aaagagaggc tgaagctaac ggcccggaaa ccctgtgtgg tgcggaactg  1200
gtggatgctc tgcaattcgt ctgtggtgac cgtggcttct acttcaataa accgaccggc  1260
tatggtagct ctagtcgtcg cgcgccgcag accggtattg tggatgaatg ctgttttcgt  1320
agctgtgacc tgcgtcgtct ggaaatgtat tgtgccccgc tgaaaccggc gaaatcggcg  1380
tgagcatgcc aaggcctcag gtaccggccg gccatttaaa tacaggcccc ttttcctttg  1440
tcgatatcat gtaattagtt atgtcacgct tacattcacg ccctcctccc acatccgctc  1500
taaccgaaaa ggaaggagtt agacaacctg aagtctaggt ccctatttat ttttttaat  1560
agttatgtta gtattaagaa cgttatttat atttcaaatt tttctttttt ttctgtacaa  1620
acgcgtgtac gcatgtaaca ttatactgaa aaccttgctt gagaaggttt tgggacgctc  1680
gaaggcttta atttgcaagc tggatccgcg gccgccttcc aaactctcat ggattctcag  1740
gtaataggta ttctaggagg aggccagcta ggccgaatga ttgttgaggc cgctagcagg  1800
ctcaatatca agaccgtgat tcttgatgat ggtttttcac ctgctaagca cattaatgct  1860
gcgcaagacc acatcgacgg atcattcaaa gatgaggagg ctatcgccaa gttagctgcc  1920
aaatgtgatg ttctcactgt agagattgag catgtcaaca cagatgctct aaagagagtt  1980
caagacagaa ctggaatcaa gatatatcct ttaccagaga caatcgaact aatcaaggat  2040
aagtacttgc aaaaggaaca tttgatcaag cacaacattt cggtgacaaa gtctcagggt  2100
atagaatcta atgaaaaggc gctgcttttg tttggagaag agaatggatt tccatatctg  2160
ttgaagtccc ggactatggc ttatgatgga agaggcaatt ttgtagtgga gtctaaagag  2220
gacatcagta aggcattaga gttcttgaaa gatcgtccat tgtatgccga gaagtttgct  2280
ccttttgtta aagaattagc ggtaatggtt gtgagatcac tggaaggcga agtattctcc  2340
tacccaaccg tagaaactgt gcacaaggac aatatctgtc atattgtgta tgctccggcc  2400
agagttaatg acaccatcca aaagaaagct caaatattag ctgaaaacac tgtgaagact  2460
ttcccaggcg ctggaatctt cggagttgag atgttcctat tgtctgatgg agaacttctt  2520
gtaaatgaga ttgctccaag gccccacaat tctggtcact atacaatcga tgcatgtgta  2580
acatctcagt tcgaagcaca tgtaagagcc ataactggtc tgccaatgcc actagatttc  2640
accaaactat ctacttccaa caccaacgct attatgctca atgttttggg tgctgaaaaa  2700
tctcacgggg aattagagtt ttgtagaaga gccttagaaa cacccggtgc ttctgtatat  2760
ctgtacggaa agaccacccg attggctcgt aagatgggtc atatcaacat aataggatct  2820
tccatgttgg aagcagaaca aaagttagag tacattctag aagaatcaac ccacttacca  2880
tccagtactg tatcagctga cactaaaccg ttggttggag ttatcatggg ttcagactct  2940
gatctacctg tgatttcgaa aggttgcgat attttaaaac agtttggtgt tccattcgaa  3000
gttactattg tctctgctca tagaacacca cagagaatga ccagatatgc ctttgaagcc  3060
gctagtagag gtatcaaggc tatcattgca ggtgctggtg gtgctgctca tcttccagga  3120
atggttgctg ccatgactcc gttgccagtc attggtgttc ctgtcaaggg ctctacgttg  3180
gatggtgtag actcgctaca ctcgattgtc caaatgccta gaggtgttcc tgtggctacg  3240
gttgctatca acaacgccac caatgccgct ctgttggcca tcaggatttt aggtacaatt  3300
gaccacaaat ggcaaaagga aatgtccaag tatatgaatg caatggagac cgaagtgttg  3360
gggaaggcat ccaacttgga atctgaaggg tatgaatcct atttgaagaa tcgtctttga  3420
atttagtatt gtttttaat agatgtatat ataatagtac acgtaactta tctattccat  3480
tcataatttt attttaaagg ttcggtagaa atttgtcctc caaaaagttg gttagagcct  3540
ggcagttttg ataggcatta ttatagattg ggtaatattt accctgcacc tggaggaact  3600
ttgcaaagag cctcatgtgc ggcgcgccag gccataatgg ccaaacggtt tctcaattac  3660
tatatactac taaccattta cctgtagcgt atttcttttc cctcttcgcg aaagctcaag  3720
ggcatcttct tgactcatga aaaatatctg gatttcttct gacagatcat caccccttgag  3780
cccaactctc tagcctatga gtgtaagtga tagtcatctt gcaacagatt attttggaac  3840
gcaactaaca aagcagatac acccttcagc agaatccttt ctggatattg tgaagaatga  3900
tcgccaaagt cacagtcctg agacagttcc taatctttac cccatttaca agttcatcca  3960
atcagacttc ttaacgcctc atctggctta tatcaagctt accaacagtt cagaaactcc  4020
cagtccaagt ttcttgcttg aaagtgcgaa gaatggtgac accgttgaca ggtacacctt  4080
tatgggacat tcccccagaa aaataatcaa gactgggcct ttagagggtg ctgaagttga  4140
ccccttggtg cttctggaaa aagaactgaa gggcaccaga caagcgcaac ttcctggtat  4200
tcctcgtcta agtggtggtg ccataggata catctcgtac gattgtatta agtactttga  4260
accaaaaact gaaagaaaac tgaaagatgt tttgcaactt ccggaagcag ctttgatgtt  4320
gttcgacacg atcgtggctt ttgacaatgt ttatcaaaga ttccaggtaa ttggaaacgt  4380
ttctctatcc gttgatgact cggacgaagc tattcttgag aaatattata agacaagaga  4440
agaagtggaa aagatcagta aagtggtatt tgacaataaa actgttccct actatgaaca  4500
gaaagatatt attcaaggcc aaacgttcac ctctaatatt ggtcaggaag ggtatgaaaa  4560
ccatgttcgc aagctgaaag aacatattct gaaaggagac atcttccaag ctgttccctc  4620
tcaaagggta gccaggccga cctcattgca ccctttcaac atctatcgtc atttgagaac  4680
tgtcaatcct tctccataca tgttctatat tgactatcta gacttccaag ttgttggtgc  4740
ttcacctgaa ttactagtta aatccgacaa caacaacaaa atcatcacac atcctattgc  4800
tggaactctt cccagaggta aaactatcga agaggacgac aattatgcta agcaattgaa  4860
gtcgtctttg aaagacaggg ccgagcacgt catgctggta gatttggcca gaaatgatat  4920
taaccgtgtg tgtgagccca ccagtaccac ggttgatcgt ttattgactg tggagagatt  4980
ttctcatgtg atgcatcttg tgtcagaagt cagtggaaca ttgagaccaa acaagactcg  5040
cttcgatgct ttcagatcca ttttcccagc aggaaccgtc tccggtgctc cgaaggtaag  5100
agcaatgcaa ctcataggag aattggaagg agaaaagaga ggtgtttatg cgggggccgt  5160
aggacactgg tcgtacgatg gaaaatcgat ggacacatgt attgccttaa gaacaatggt  5220
cgtcaaggac ggtgtcgctt accttcaagc cggaggtgga attgtctacg attctgaccc  5280
ctatgacgag tacatcgaaa ccatgaacaa aatgagatcc aacaataaca ccatcttgga  5340
ggctgagaaa atctggaccg ataggttggc cagagacgag aatcaaagtg aatccgaaga  5400
aaacgatcaa tgaacggagg acgtaagtag gaatttatgg tttggccata atggcctagc  5460
ttggcgtaat catggtcata gctgtttcct gtgtgaaatt gttatccgct cacaattcca  5520
cacaacatac gagccggaag cataaagtgt aaagcctggg gtgcctaatg agtgagctaa  5580
ctcacattaa ttgcgttgcg ctcactgccc gctttccagt cgggaaacct gtcgtgccag  5640
ctgcattaat gaatcggcca acgcgcgggg agaggcggtt tgcgtattgg gcgctcttcc  5700
gcttcctcgc tcactgactc gctgcgctcg gtcgttcggc tgcggcgagc ggtatcagct  5760
```

```
cactcaaagg cggtaatacg gttatccaca gaatcagggg ataacgcagg aaagaacatg  5820
tgagcaaaag gccagcaaaa ggccaggaac cgtaaaaagg ccgcgttgct ggcgtttttc  5880
cataggctcc gcccccctga cgagcatcac aaaaatcgac gctcaagtca gaggtggcga  5940
aacccgacag gactataaag ataccaggcg tttccccctg gaagctccct cgtgcgctct  6000
cctgttccga ccctgccgct taccggatac ctgtccgcct ttctcccttc gggaagcgtg  6060
gcgctttctc atagctcacg ctgtaggtat ctcagttcgg tgtaggtcgt tcgctccaag  6120
ctgggctgtg tgcacgaacc ccccgttcag cccgaccgct gcgccttatc cggtaactat  6180
cgtcttgagt ccaacccggt aagacacgac ttatcgccac tggcagcagc cactggtaac  6240
aggattagca gagcgaggta tgtaggcggt gctacagagt tcttgaagtg gtggcctaac  6300
tacggctaca ctagaaggac agtatttggt atctgcgctc tgctgaagcc agttaccttc  6360
ggaaaaagag ttggtagctc ttgatccggc aaacaaacca ccgctggtag cggtggtttt  6420
tttgtttgca agcagcagat tacgcgcaga aaaaaaggat ctcaagaaga tcctttgatc  6480
ttttctacgg ggtctgacgc tcagtggaac gaaaactcac gttaagggat tttggtcatg  6540
agattatcaa aaaggatctt cacctagatc cttttaaatt aaaaatgaag ttttaaatca  6600
atctaaagta tatatgagta aacttggtct gacagttacc aatgcttaat cagtgaggca  6660
cctatctcag cgatctgtct atttcgttca tccatagttg cctgactccc cgtcgtgtag  6720
ataactacga tacgggaggg cttaccatct ggccccagtg ctgcaatgat accgcgagac  6780
ccacgctcac cggctccaga tttatcagca ataaaccagc cagccggaag ggccgagcgc  6840
agaagtggtc ctgcaacttt atccgcctcc atccagtcta ttaattgttg ccgggaagct  6900
agagtaagta gttcgccagt taatagtttg cgcaacgttg ttgccattgc tacaggcatc  6960
gtggtgtcac gctcgtcgtt tggtatggct tcattcagct ccggttccca acgatcaagg  7020
cgagttacat gatcccccat gttgtgcaaa aaagcggtta gctccttcgg tcctccgatc  7080
gttgtcagaa gtaagttggc cgcagtgtta tcactcatgg ttatggcagc actgcataat  7140
tctcttactg tcatgccatc cgtaagatgc ttttctgtga ctggtgagta ctcaaccaag  7200
tcattctgag aatagtgtat gcggcgaccg agttgctctt gcccggcgtc aatacgggat  7260
aataccgcgc cacatagcag aactttaaaa gtgctcatca ttggaaaacg ttcttcgggg  7320
cgaaaactct caaggatctt accgctgttg agatccagtt cgatgtaacc cactcgtgca  7380
cccaactgat cttcagcatc ttttactttc accagcgttt ctgggtgagc aaaaacagga  7440
aggcaaaatg ccgcaaaaaa gggaataagg gcgacacgga aatgttgaat actcatactc  7500
ttcctttttc aatattattg aagcatttat cagggttatt gtctcatgag cggatacata  7560
tttgaatgta tttagaaaaa taaacaaata ggggttccgc gcacatttcc ccgaaaagtg  7620
ccacctgacg tctaagaaac cattattatc atgacattaa cctataaaaa taggcgtatc  7680
acgaggccct ttcgtctcgc gcgtttcggt gatgacggtg aaaacctctg acacatgcag  7740
ctcccggaga cggtcacagc ttgtctgtaa gcggatgccg ggagcagaca agcccgtcag  7800
ggcgcgtcag cgggtgttgg cgggtgtcgg ggctggctta actatgcggc atcagagcag  7860
attgtactga gagtgcacca tatgcggtgt gaaataccgc acagatgcgt aaggagaaaa  7920
taccgcatca ggcgccattc gccattcagg ctgcgcaact gttgggaagg gcgatcggtg  7980
cgggcctctt cgctattacg ccagctggcg aaagggggat gtgctgcaag gcgattaagt  8040
tgggtaacgc cagggttttc ccagtcacga cgttgtaaaa cgacggccag tgaattg     8097

SEQ ID NO: 11          moltype = DNA  length = 16650
FEATURE                Location/Qualifiers
misc_feature           1..16650
                       note = pPinkHC-6XscvSrh(R)1-alphapro-GR-hIGF1
source                 1..16650
                       mol_type = other DNA
                       organism = synthetic construct
SEQUENCE: 11
ggaaccgatc taacatccaa agacgaaagg ttgaatgaaa ccttttttgcc atccgacatc  60
cacaggtcca ttctcacaca taagtgccaa acgcaacagg aggggataca ctagcagcag  120
accgttgcaa acgcaggacc tccactcctc ttctcctcaa cacccacttt tgccatcgaa  180
aaaccagccc agttattggg cttgattgga gctcgctcat tccaattcct tctattaggc  240
tactaacacc atgactttat tagcctgtct atcctggccc ccctggcgag gttcatgttt  300
gtttatttcc gaatgcaaca agctccgcat tacacccgaa catcactcca gatgagggct  360
ttctgagtgt ggggtcaaat agtttcatgt tccccaaatg gcccaaaact gacagtttaa  420
acgctgtctt ggaacctaat atgacaaaag cgtgatctca tccaagatga actaagtttg  480
gttcgttgaa atgctaacgg ccagttggtc aaaaagaaac ttccaaaagt cggcataccg  540
tttgtcttgt ttggtattga ttgacgaatg ctcaaaaata atctcattaa tgcttagcgc  600
agtctctcta tcgcttctga accccggtgc acctgtgccg aaacgcaaat ggggaaacac  660
ccgctttttg gatgattatg cattgtctcc acattgtatg cttccaagat tctggtggga  720
atactgctga tagcctaacg ttcatgatca aaatttaact gttctaaccc ctacttgaca  780
gcaatatata aacagaagga agctgccctg tcttaaacct ttttttttat catcattatt  840
agcttacttt cataattgcg actggttcca attgacaagc ttttgatttt aacgactttt  900
aacgacaact tgagaagatc aaaaaacaac taattattcg aaacggaatt caaaaaatgc  960
gacagttctc catcgttgcc ctcttcgcta ctggcgctct cgccgctcca gtcaacacta  1020
caacagaaga tgaaacggca caaattccgg ctgaagctgt catcggttac tcagatttag  1080
aaggggattt cgatgttgct gttttgccat tttccgccag cattgctgct aaagaagaag  1140
gggtatctct cgagaaaaga gaggctgaag ctggtcgggg cccggaaacc ctgtgtggtg  1200
cggaactggt ggatgctctg caattcgtct gtggtgaccg tggcttctac ttcaataaac  1260
cgaccggcta tggtagctct agtcgtcgcg cgccgcagac cggtattgtg gatgaatgct  1320
gttttcgtag ctgtgacctg cgtcgtctgg aaatgtattg tgccccgctg aaaccggcga  1380
aatcggcgtg agcatgccaa ggcctcaggt accggccggc catttaaata caggcccctt  1440
ttcctttgtc gatatcatgt aattagttat gtcacgctta cattcacgcc ctcctcccac  1500
atccgctcta accgaaaagg aaggagttag acaacctgaa gtctaggtcc ctatttattt  1560
tttttaatag ttatgttagt attaagaacg ttatttatat ttcaaatttt tcttttttttt  1620
ctgtacaaac gcgtgtacgc atgtaacatt atactgaaaa ccttgcttga gaaggttttg  1680
ggacgctcga aggctttaat ttgcaagctg gaaccgatct aacatccaaa gacgaaaggt  1740
tgaatgaaac ctttttgcca tccgacatcc acaggtccat tctcacacat aagtgccaaa  1800
cgcaacagga ggggatacac tagcagcaga ccgttgcaaa cgcaggacct ccactcctct  1860
```

```
tctcctcaac acccactttt gccatcgaaa aaccagccca gttattgggc ttgattggag  1920
ctcgctcatt ccaattcctt ctattaggct actaacacca tgactttatt agcctgtcta  1980
tcctggcccc cctggcgagg ttcatgtttg tttatttccg aatgcaacaa gctccgcatt  2040
acacccgaac atcactccag atgagggctt tctgagtgtg gggtcaaata gtttcatgtt  2100
ccccaaatgg cccaaaactg acagtttaaa cgctgtcttg gaacctaata tgacaaaagc  2160
gtgatctcat ccaagatgaa ctaagtttgg ttcgttgaaa tgctaacggc cagttggtca  2220
aaaagaaact tccaaaagtc ggcataccgt ttgtcttgtt tggtattgat tgacgaatgc  2280
tcaaaaataa tctcattaat gcttagcgca gtctctctat cgcttctgaa ccccggtgca  2340
cctgtgccga aacgcaaatg ggaaacacc cgctttttgg atgattatgc attgtctcca  2400
cattgtatgc ttccaagatt ctggtgggaa tactgctgat agcctaacgt tcatgatcaa  2460
aatttaactg ttctaacccc tacttgacag caatatataa acagaaggaa gctgccctgt  2520
cttaaacctt ttttttatc atcattatta gcttactttc ataattgcga ctggttccaa  2580
ttgacaagct tttgatttta acgactttta acgacaactt gagaagatca aaaaacaact  2640
aattattcga aacggaattc aaaaaatgcg acagttctcc atcgttgccc tcttcgctac  2700
tggcgctctc gccgctccag tcaacactac aacagaagat gaaacggcac aaattccggc  2760
tgaagctgtc atcggttact cagatttaga aggggatttc gatgttgctg ttttgccatt  2820
ttccgccagc attgctgcta aagaagaagg ggtatctctc gagaaaagag aggctgaagc  2880
tggtcggggc ccggaaaccc tgtgtggtgc ggaactggtg gatgctctgc aattcgtctg  2940
tggtgaccgt ggcttctact tcaataaacc gaccggctat ggtagctcta gtcgtcgcgc  3000
gccgcagacc ggtattgtgg atgaatgctg ttttcgtagc tgtgacctgc gtcgtctgga  3060
aatgtattgt gccccgctga aaccggcgaa atcggcgtga gcatgccaag gcctcaggta  3120
ccggccggcc atttaaatac aggccccttt tcctttgtcg atatcatgta attagttatg  3180
tcacgcttac attcacgccc tcctccccaca tccgctctaa ccgaaaagga aggagttaga  3240
caacctgaag tctaggtccc tatttatttt ttttaatagt tatgttagta ttaagaacgt  3300
tatttatatt tcaaattttt cttttttttc tgtacaaacg cgtgtacgca tgtaacatta  3360
tactgaaaac cttgcttgag aaggttttgg gacgctcgaa ggctttaatt tgcaagctgg  3420
aaccgatcta acatccaaag acgaaaggtt gaatgaaacc tttttgccat ccgacatcca  3480
caggtccatt ctcacacata agtgccaaac gcaacaggag gggatacact agcagcagac  3540
cgttgcaaac gcaggacctc cactcctctt ctcctcaaca cccacttttg ccatcgaaaa  3600
accagcccag ttattgggct tgattggagc tcgctcattc caattccttc tattaggcta  3660
ctaacaccat gactttatta gcctgtctat cctggccccc ctggcgaggt tcatgtttgt  3720
ttatttccga atgcaacaag ctccgcatta cacccgaaca tcactccaga tgagggcttt  3780
ctgagtgtgg ggtcaaatag tttcatgttc cccaaatggc ccaaaactga cagtttaaac  3840
gctgtcttgg aacctaatat gacaaaagcg tgatctcatc caagatgaac taagtttggt  3900
tcgttgaaat gctaacggcc agttggtcaa aaagaaactt ccaaaagtcg gcataccgtt  3960
tgtcttgttt ggtattgatt gacgaatgct caaaaataat ctcattaatg cttagcgcag  4020
tctctctatc gcttctgaac cccggtgcac ctgtgccgaa acgcaaatgg ggaaacaccc  4080
gctttttgga tgattatgca ttgtctccac attgtatgct tccaagattc tggtgggaat  4140
actgctgata gcctaacgtt catgatcaaa atttaactgt tctaacccct acttgacagc  4200
aatatataaa cagaaggaag ctgccctgtc ttaaaccttt ttttttatca tcattattag  4260
cttactttca taattgcgac tggttccaat tgacaagctt ttgattttaa cgacttttaa  4320
cgacaacttg agaagatcaa aaaacaacta attattcgaa acggaattca aaaaatgcga  4380
cagttctcca tcgttgccct cttcgctact ggcgctctcg ccgctccagt caacactaca  4440
acagaagatg aaacggcaca aattccggct gaagctgtca tcggttactc agatttagaa  4500
ggggatttcg atgttgctgt tttgccattt tccgccagca ttgctgctaa agaagaaggg  4560
gtatctctcg agaaaagaga ggctgaagct ggtcggggcc cggaaaccct gtgtggtgcg  4620
gaactggtgg atgctctgca attcgtctgt ggtgaccgtg gcttctactt caataaaccg  4680
accggctatg gtagctctag tcgtcgcgcg ccgcagaccg gtattgtgga tgaatgctgt  4740
tttcgtagct gtgacctgcg tcgtctggaa atgtattgtg ccccgctgaa accggcgaaa  4800
tcggcgtgag catgccaagg cctcaggtac cggccggcca tttaaataca ggccccttt  4860
cctttgtcga tatcatgtaa ttagttatgt cacgcttaca ttcacgccct cctcccacat  4920
ccgctctaac cgaaaaggaa ggagttagac aacctgaagt ctaggtccct atttattttt  4980
tttaatagtt atgttagtat taagaacgtt atttatattt caaatttttc ttttttttct  5040
gtacaaacgc gtgtacgcat gtaacattat actgaaaacc ttgcttgaga aggttttggg  5100
acgctcgaag gctttaattt gcaagctgga accgatctaa catccaaaga cgaaaggttg  5160
aatgaaacct ttttgccatc cgacatccac aggtccattc tcacacataa gtgccaaacg  5220
caacaggagg ggatacacta gcagcagacc gttgcaaacg caggacctcc actcctcttc  5280
tcctcaacac ccacttttgc catcgaaaaa ccagcccagt tattgggctt gattggagct  5340
cgctcattcc aattccttct attaggctac taacaccatg actttattag cctgtctatc  5400
ctggcccccc tggcgaggtt catgtttgtt tatttccgaa tgcaacaagc tccgcattac  5460
acccgaacat cactccagat gagggctttc tgagtgtggg gtcaaatagt ttcatgttcc  5520
ccaaatggcc caaaactgac agtttaaacg ctgtcttgga acctaatatg acaaaagcgt  5580
gatctcatcc aagatgaact aagtttggtt cgttgaaatg ctaacggcca gttggtcaaa  5640
aagaaacttc caaaagtcgg cataccgttt gtcttgtttg gtattgattg acgaatgctc  5700
aaaaataatc tcattaatgc ttagcgcagt ctctctatcg cttctgaacc ccggtgcacc  5760
tgtgccgaaa cgcaaatggg gaaacacccg ctttttggat gattatgcat tgtctccaca  5820
ttgtatgctt ccaagattct ggtgggaata ctgctgatag cctaacgttc atgatcaaaa  5880
tttaactgtt ctaaccccta cttgacagca atatataaac agaaggaagc tgccctgtct  5940
taaacctttt tttttatcat cattattagc ttactttcat aattgcgact ggttccaatt  6000
gacaagcttt tgattttaac gacttttaac gacaacttga gaagatcaaa aaacaactaa  6060
ttattcgaaa cggaattcaa aaaatgcgac agttctccat cgttgccctc ttcgctactg  6120
gcgctctcgc cgctccagtc aacactacaa cagaagatga aacggcacaa attccggctg  6180
aagctgtcat cggttactca gatttagaag gggatttcga tgttgctgtt ttgccatttt  6240
ccgccagcat tgctgctaaa gaagaagggg tatctctcga gaaaagagag gctgaagctg  6300
gtcggggccc ggaaaccctg tgtggtgcgg aactggtgga tgctctgcaa ttcgtctgtg  6360
gtgaccgtgg cttctacttc aataaaccga ccggctatgg tagctctagt cgtcgcgcgc  6420
cgcagaccgg tattgtggat gaatgctgtt ttcgtagctg tgacctgcgt cgtctggaaa  6480
tgtattgtgc cccgctgaaa ccggcgaaat cggcgtgagc atgccaaggc ctcaggtacc  6540
ggccggccat ttaaatacag gccccttttc ctttgtcgat atcatgtaat tagttatgtc  6600
```

```
acgcttacat tcacgccctc ctcccacatc cgctctaacc gaaaaggaag gagttagaca  6660
acctgaagtc taggtcccta tttatttttt ttaatagtta tgttagtatt aagaacgtta  6720
tttatatttc aaatttttct tttttttctg tacaaacgcg tgtacgcatg taacattata  6780
ctgaaaacct tgcttgagaa ggttttggga cgctcgaagg ctttaatttg caagctggaa  6840
ccgatctaac atccaaagac gaaaggttga atgaaacctt tttgccatcc gacatccaca  6900
ggtccattct cacacataag tgccaaacgc aacaggaggg gatacactag cagcagaccg  6960
ttgcaaacgc aggacctcca ctcctcttct cctcaacacc cacttttgcc atcgaaaaac  7020
cagcccagtt attgggcttg attggagctc gctcattcca attccttcta ttaggctact  7080
aacaccatga ctttattagc ctgtctatcc tggccccccct ggcgaggttc atgtttgttt  7140
atttccgaat gcaacaagct ccgcattaca cccgaacatc actccagatg agggctttct  7200
gagtgtgggg tcaaatagtt tcatgttccc caaatggccc aaaactgaca gtttaaacgc  7260
tgtcttggaa cctaatatga caaaagcgtg atctcatcca agatgaacta agtttggttc  7320
gttgaaatgc taacggccag ttggtcaaaa agaaacttcc aaaagtcggc ataccgtttg  7380
tcttgtttgg tattgattga cgaatgctca aaaataatct cattaatgct tagcgcagtc  7440
tctctatcgc ttctgaaccc cggtgcacct gtgccgaaac gcaaatgggg aaacacccgc  7500
tttttggatg attatgcatt gtctccacat tgtatgcttc caagattctg gtgggaatac  7560
tgctgatagc ctaacgttca tgatcaaaat ttaactgttc taacccctac ttgacagcaa  7620
tatataaaca gaaggaagct gccctgtctt aaaccttttt ttttatcatc attattagct  7680
tactttcata attgcgactg gttccaattg acaagctttt gattttaacg acttttaacg  7740
acaacttgag aagatcaaaa aacaactaat tattcgaaac ggaattcaaa aaatgcgaca  7800
gttctccatc gttgccctct tcgctactgg cgctctcgcc gctccagtca acactacaac  7860
agaagatgaa acggcacaaa ttccggctga agctgtcatc ggttactcag atttagaagg  7920
ggatttcgat gttgctgttt tgccattttc cgccagcatt gctgctaaag aagaaggggt  7980
atctctcgag aaaagagagg ctgaagctgg tcggggcccg gaaaccctgt gtggtgcgga  8040
actggtggat gctctgcaat tcgtctgtgg tgaccgtggc ttctacttca ataaaccgac  8100
cggctatggt agctctagtc gtcgcgcgcc gcagaccggt attgtggatg aatgctgttt  8160
tcgtagctgt gacctgcgtc gtctggaaat gtattgtgcc ccgctgaaac cggcgaaatc  8220
ggcgtgagca tgccaaggcc tcaggtaccg gccggccatt taaatacagg cccctttttcc  8280
tttgtcgata tcatgtaatt agttatgtca cgcttacatt cacgccctcc tcccacatcc  8340
gctctaaccg aaaaggaagg agttagacaa cctgaagtct aggtccctat ttattttttt  8400
taatagttat gttagtatta agaacgttat ttatatttca aatttttctt ttttttctgt  8460
acaaacgcgt gtacgcatgt aacattatac tgaaaacctt gcttgagaag gttttgggac  8520
gctcgaaggc tttaatttgc aagctggaac cgatctaaca tccaaagacg aaaggttgaa  8580
tgaaaccttt ttgccatccg acatccacag gtccattctc acacataagt gccaaacgca  8640
acaggagggg atacactagc agcagaccgt tgcaaacgca ggacctccac tcctcttctc  8700
ctcaacaccc acttttgcca tcgaaaaacc agcccagtta ttgggcttga ttggagctcg  8760
ctcattccaa ttccttctat taggctacta acaccatgac tttattagcc tgtctatcct  8820
ggcccccctg gcgaggttca tgtttgttta tttccgaatg caacaagctc cgcattacac  8880
ccgaacatca ctccagatga gggctttctg agtgtggggt caaatagttt catgttcccc  8940
aaatggccca aaactgacag tttaaacgct gtcttggaac ctaatatgac aaaagcgtga  9000
tctcatccaa gatgaactaa gtttggttcg ttgaaatgct aacggccagt tggtcaaaaa  9060
gaaacttcca aaagtcggca taccgtttgt cttgtttggt attgattgac gaatgctcaa  9120
aaataatctc attaatgctt agcgcagtct ctctatcgct tctgaacccc ggtgcacctg  9180
tgccgaaacg caaatgggga aacacccgct ttttggatga ttatgcattg tctccacatt  9240
gtatgcttcc aagattctgg tgggaatact gctgatagcc taacgttcat gatcaaaatt  9300
taactgttct aacccctact tgacagcaat atataaacag aaggaagctg ccctgtctta  9360
aacctttttt tttatcatca ttattagctt actttcataa ttgcgactgg ttccaattga  9420
caagcttttg attttaacga cttttaacga caacttgaga agatcaaaaa acaactaatt  9480
attcgaaacg gaattcaaaa aatgcgacag ttctccatcg ttgccctctt cgctactggc  9540
gctctcgccg ctccagtcaa cactacaaca gaagatgaaa cggcacaaat tccggctgaa  9600
gctgtcatcg gttactcaga tttagaaggg gatttcgatg ttgctgtttt gccattttcc  9660
gccagcattg ctgctaaaga agaaggggta tctctcgaga aaagagaggc tgaagctggt  9720
cggggcccgg aaaccctgtg tggtgcggaa ctggtggatg ctctgcaatt cgtctgtggt  9780
gaccgtggct tctacttcaa taaaccgacc ggctatggta gctctagtcg tcgcgcgccg  9840
cagaccggta ttgtggatga atgctgtttt cgtagctgtg acctgcgtcg tctggaaatg  9900
tattgtgccc cgctgaaacc ggcgaaatcg gcgtgagcat gccaaggcct caggtaccgg  9960
ccggccattt aaatacaggc ccctttttcct ttgtcgatat catgtaatta gttatgtcac  10020
gcttacattc acgccctcct cccacatccg ctctaaccga aaaggaagga gttagacaac  10080
ctgaagtcta ggtccctatt tatttttttt aatagttatg ttagtattaa gaacgttatt  10140
tatatttcaa atttttcttt tttttctgta caaacgcgtg tacgcatgta acattatact  10200
gaaaaccttg cttgagaagg ttttgggacg ctcgaaggct ttaatttgca agctggatcc  10260
gcggccgcct tccaaactct catggattct caggtaatag gtattctagg aggaggccag  10320
ctaggccgaa tgattgttga ggccgctagc aggctcaata tcaagaccgt gattcttgat  10380
gatggttttt cacctgctaa gcacattaat gctgcgcaag accacatcga cggatcattc  10440
aaagatgagg aggctatcgc caagttagct gccaaatgtg atgttctcac tgtagagatt  10500
gagcatgtca acacagatgc tctaaagaga gttcaagaca gaactggaat caagatatat  10560
cctttaccag agacaatcga actaatcaag gataagtact tgcaaaagga acatttgatc  10620
aagcacaaca tttcggtgac aaagtctcag ggtatagaat ctaatgaaaa ggcgctgctt  10680
ttgtttggag aagagaatgg atttccatat ctgttgaagt cccggactat ggcttatgat  10740
ggaagaggca attttgtagt ggagtctaaa gaggacatca gtaaggcatt agagttcttg  10800
aaagatcgtc cattgtatgc cgagaagttt gctccttttg ttaaagaatt agcggtaatg  10860
gttgtgagat cactggaagg cgaagtattc tcctacccaa ccgtagaaac tgtgcacaag  10920
gacaatatct gtcatattgt gtatgctccg gccagagtta atgacaccat ccaaaagaaa  10980
gctcaaatat tagctgaaaa cactgtgaag actttcccag gcgctggaat cttcggagtt  11040
gagatgttcc tattgtctga tggagaactt cttgtaaatg agattgctcc aaggccccac  11100
aattctggtc actatacaat cgatgcatgt gtaacatctc agttcgaagc acatgtaaga  11160
gccataactg gtctgccaat gccactagat ttcaccaaac tatctacttc caacaccaac  11220
gctattatgc tcaatgtttt gggtgctgaa aaatctcacg ggaattaga gttttgtaga  11280
agagccttag aaacacccgg tgcttctgta tatctgtacg gaaagaccac ccgattggct  11340
```

```
cgtaagatgg gtcatatcaa cataatagga tcttccatgt tggaagcaga acaaaagtta  11400
gagtacattc tagaagaatc aacccactta ccatccagta ctgtatcagc tgacactaaa  11460
ccgttggttg gagttatcat gggttcagac tctgatctac ctgtgatttc gaaaggttgc  11520
gatattttaa aacagtttgg tgttccattc gaagttacta ttgtctctgc tcatagaaca  11580
ccacagagaa tgaccagata tgcctttgaa gccgctagta gaggtatcaa ggctatcatt  11640
gcaggtgctg gtggtgctgc tcatcttcca ggaatggttg ctgccatgac tccgttgcca  11700
gtcattggtg ttcctgtcaa gggctctacg ttggatggtg tagactcgct acactcgatt  11760
gtccaaatgc ctagaggtgt tcctgtggct acggttgcta tcaacaacgc caccaatgcc  11820
gctctgttgg ccatcaggat tttaggtaca attgaccaca aatggcaaaa ggaaatgtcc  11880
aagtatatga atgcaatgga gaccgaagtg ttggggaagg catccaactt ggaatctgaa  11940
gggtatgaat cctatttgaa gaatcgtctt tgaatttagt attgtttttt aatagatgta  12000
tatataatag tacacgtaac ttatctattc cattcataat tttattttaa aggttcggta  12060
gaaatttgtc ctccaaaaag ttggttagag cctggcagtt ttgataggca ttattataga  12120
ttgggtaata tttaccctgc acctggagga actttgcaaa gagcctcatg tgcggcgcgc  12180
caggccataa tggccaaacg gtttctcaat tactatatac tactaaccat ttacctgtag  12240
cgtatttctt ttccctcttc gcgaaagctc aagggcatct tcttgactca tgaaaaatat  12300
ctggatttct tctgacagat catcaccctt gagcccaact ctctagccta tgagtgtaag  12360
tgatagtcat cttgcaacag attattttgg aacgcaacta acaaagcaga tacacccttc  12420
agcagaatcc tttctggata ttgtgaagaa tgatcgccaa agtcacagtc ctgagacagt  12480
tcctaatctt taccccattt acaagttcat ccaatcagac ttcttaacgc ctcatctggc  12540
ttatatcaag cttaccaaca gttcagaaac tcccagtcca agtttcttgc ttgaaagtgc  12600
gaagaatggt gacaccgttg acaggtacac ctttatggga cattccccca gaaaaataat  12660
caagactggg cctttagagg gtgctgaagt tgaccccttg gtgcttctgg aaaaagaact  12720
gaagggcacc agacaagcgc aacttcctgg tattcctcgt ctaagtggtg gtgccatagg  12780
atacatctcg tacgattgta ttaagtactt tgaaccaaaa actgaaagaa aactgaaaga  12840
tgttttgcaa cttccggaag cagctttgat gttgttcgac acgatcgtgg cttttgacaa  12900
tgtttatcaa agattccagg taattggaaa cgtttctcta tccgttgatg actcggacga  12960
agctattctt gagaaatatt ataagacaag agaagaagtg gaaaagatca gtaaagtggt  13020
atttgacaat aaaactgttc cctactatga acagaaagat attattcaag gccaaacgtt  13080
cacctctaat attggtcagg aagggtatga aaaccatgtt cgcaagctga aagaacatat  13140
tctgaaagga gacatcttcc aagctgttcc ctctcaaagg gtagccaggc cgacctcatt  13200
gcaccctttc aacatctatc gtcatttgag aactgtcaat ccttctccat acatgttcta  13260
tattgactat ctagacttcc aagttgttgg tgcttcacct gaattactag ttaaatccga  13320
caacaacaac aaaatcatca cacatcctat tgctggaact cttcccagag gtaaaactat  13380
cgaagaggac gacaattatg ctaagcaatt gaagtcgtct ttgaaagaca gggccgagca  13440
cgtcatgctg gtagatttgg ccagaaatga tattaaccgt gtgtgtgagc ccaccagtac  13500
cacggttgat cgtttattga ctgtggagag attttctcat gtgatgcatc ttgtgtcaga  13560
agtcagtgga acattgagac caaacaagac tcgcttcgat gctttcagat ccattttccc  13620
agcaggaacc gtctccggtg ctccgaaggt aagagcaatg caactcatag gagaattgga  13680
aggagaaaag agaggtgttt atgcgggggc cgtaggacac tggtcgtacg atggaaaatc  13740
gatggacaca tgtattgcct taagaacaat ggtcgtcaag gacggtgtcg cttaccttca  13800
agccggaggt ggaattgtct acgattctga cccctatgac gagtacatcg aaaccatgaa  13860
caaaatgaga tccaacaata acaccatctt ggaggctgag aaaatctgga ccgataggtt  13920
ggccagagac gagaatcaaa gtgaatccga agaaaacgat caatgaacgg aggacgtaag  13980
taggaattta tggtttggcc ataatggcct agcttggcgt aatcatggtc atagctgttt  14040
cctgtgtgaa attgttatcc gctcacaatt ccacacaaca tacgagccgg aagcataaag  14100
tgtaaagcct ggggtgccta atgagtgagc taactcacat taattgcgtt gcgctcactg  14160
cccgctttcc agtcgggaaa cctgtcgtgc cagctgcatt aatgaatcgg ccaacgcgcg  14220
gggagaggcg gtttgcgtat tgggcgctct tccgcttcct cgctcactga ctcgctgcgc  14280
tcggtcgttc ggctgcggcg agcggtatca gctcactcaa aggcggtaat acggttatcc  14340
acagaatcag gggataacgc aggaaagaac atgtgagcaa aaggccagca aaaggccagg  14400
aaccgtaaaa aggccgcgtt gctggcgttt ttccataggc tccgcccccc tgacgagcat  14460
cacaaaaatc gacgctcaag tcagaggtgg cgaaacccga caggactata aagataccag  14520
gcgtttcccc ctggaagctc cctcgtgcgc tctcctgttc cgaccctgcc gcttaccgga  14580
tacctgtccg cctttctccc ttcgggaagc gtggcgcttt ctcatagctc acgctgtagg  14640
tatctcagtt cggtgtaggt cgttcgctcc aagctgggct gtgtgcacga accccccgtt  14700
cagcccgacc gctgcgcctt atccggtaac tatcgtcttg agtccaaccc ggtaagacac  14760
gacttatcgc cactggcagc agccactggt aacaggatta gcagagcgag gtatgtaggc  14820
ggtgctacag agttcttgaa gtggtggcct aactacggct acactagaag gacagtattt  14880
ggtatctgcg ctctgctgaa gccagttacc ttcggaaaaa gagttggtag ctcttgatcc  14940
ggcaaacaaa ccaccgctgg tagcggtggt ttttttgttt gcaagcagca gattacgcgc  15000
agaaaaaaag gatctcaaga agatcctttg atcttttcta cggggtctga cgctcagtgg  15060
aacgaaaact cacgttaagg gattttggtc atgagattat caaaaaggat cttcacctag  15120
atccttttaa attaaaaatg aagttttaaa tcaatctaaa gtatatatga gtaaacttgg  15180
tctgacagtt accaatgctt aatcagtgag gcacctatct cagcgatctg tctatttcgt  15240
tcatccatag ttgcctgact ccccgtcgtg tagataacta cgatacggga gggcttacca  15300
tctggcccca gtgctgcaat gataccgcga gacccacgct caccggctcc agatttatca  15360
gcaataaacc agccagccgg aagggccgag cgcagaagtg gtcctgcaac tttatccgcc  15420
tccatccagt ctattaattg ttgccgggaa gctagagtaa gtagttcgcc agttaatagt  15480
ttgcgcaacg ttgttgccat tgctacaggc atcgtggtgt cacgctcgtc gtttggtatg  15540
gcttcattca gctccggttc ccaacgatca aggcgagtta catgatcccc catgttgtgc  15600
aaaaaagcgg ttagctcctt cggtcctccg atcgttgtca gaagtaagtt ggccgcagtg  15660
ttatcactca tggttatggc agcactgcat aattctctta ctgtcatgcc atccgtaaga  15720
tgcttttctg tgactggtga gtactcaacc aagtcattct gagaatagtg tatgcggcga  15780
ccgagttgct cttgcccggc gtcaatacgg gataataccg cgccacatag cagaacttta  15840
aaagtgctca tcattggaaa acgttcttcg gggcgaaaac tctcaaggat cttaccgctg  15900
ttgagatcca gttcgatgta acccactcgt gcacccaact gatcttcagc atcttttact  15960
ttcaccagcg tttctgggtg agcaaaaaca ggaaggcaaa atgccgcaaa aaagggaata  16020
agggcgacac ggaaatgttg aatactcata ctcttccttt ttcaatatta ttgaagcatt  16080
```

```
tatcagggtt attgtctcat gagcggatac atatttgaat gtatttagaa aaataaacaa  16140
ataggggttc cgcgcacatt tccccgaaaa gtgccacctg acgtctaaga aaccattatt  16200
atcatgacat taacctataa aaataggcgt atcacgaggc cctttcgtct cgcgcgtttc  16260
ggtgatgacg gtgaaaacct ctgacacatg cagctcccgg agacggtcac agcttgtctg  16320
taagcggatg ccgggagcag acaagcccgt cagggcgcgt cagcgggtgt tggcgggtgt  16380
cggggctggc ttaactatgc ggcatcagag cagattgtac tgagagtgca ccatatgcgg  16440
tgtgaaatac cgcacagatg cgtaaggaga aaataccgca tcaggcgcca ttcgccattc  16500
aggctgcgca actgttggga agggcgatcg gtgcgggcct cttcgctatt acgccagctg  16560
gcgaaagggg gatgtgctgc aaggcgatta agttgggtaa cgccagggtt ttcccagtca  16620
cgacgttgta aaacgacggc cagtgaattg                                  16650

SEQ ID NO: 12          moltype = DNA  length = 16607
FEATURE                Location/Qualifiers
misc_feature           1..16607
                       note = pPinkHC-6XscvSrh(R)1-alphapro-N-hIGF1
source                 1..16607
                       mol_type = other DNA
                       organism = synthetic construct
SEQUENCE: 12
agatctaaca tccaaagacg aaaggttgaa tgaaaccttt ttgccatccg acatccacag  60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggcccccctg gcgaggttca tgtttgttta  300
tttccgaatg caacaagctc cgcattacac ccgaacatca ctccagatga gggctttctg  360
agtgtggggt caaatagttt catgttcccc aaatggccca aaactgacag tttaaacgct  420
gtcttggaac ctaatatgac aaaagcgtga tctcatccaa gatgaactaa gtttggttcg  480
ttgaaatgct aacggccagt tggtcaaaaa gaaacttcca aaagtcggca taccgtttgt  540
cttgtttggt attgattgac gaatgctcaa aaataatctc attaatgctt agcgcagtct  600
ctctatcgct tctgaacccc ggtgcacctg tgccgaaacg caaatgggga aacacccgct  660
ttttggatga ttatgcattg tctccacatt gtatgcttcc aagattctgg tgggaatact  720
gctgatagcc taacgttcat gatcaaaatt taactgttct aacccctact tgacagcaat  780
atataaacag aaggaagctg ccctgtctta aacctttttt tttatcatca ttattagctt  840
actttcataa ttgcgactgg ttccaattga caagcttttg attttaacga cttttaacga  900
caacttgaga agatcaaaaa acaactaatt attcgaaacg gaattcaaaa aatgcgacag  960
ttctccatcg ttgccctctt cgctactggc gctctcgccg ctccagtcaa cactacaaca  1020
gaagatgaaa cggcacaaat tccggctgaa gctgtcatcg gttactcaga tttagaaggg  1080
gatttcgatg ttgctgtttt gccattttcc gccagcattg ctgctaaaga agaaggggta  1140
tctctcgaga aaagagaggc tgaagctaac ggcccggaaa ccctgtgtgg tgcggaactg  1200
gtggatgctc tgcaattcgt ctgtggtgac cgtggcttct acttcaataa accgaccggc  1260
tatggtagct ctagtcgtcg cgcgccgcag accggtattg tggatgaatg ctgttttcgt  1320
agctgtgacc tgcgtcgtct ggaaatgtat tgtgccccgc tgaaaccggc gaaatcggcg  1380
tgagcatgcc aaggcctcag gtaccggccg gccatttaaa tacaggcccc ttttcctttg  1440
tcgatatcat gtaattagtt atgtcacgct tacattcacg ccctcctccc acatccgctc  1500
taaccgaaaa ggaaggagtt agacaacctg aagtctaggt ccctatttat tttttttaat  1560
agttatgtta gtattaagaa cgttatttat atttcaaatt tttctttttt ttctgtacaa  1620
acgcgtgtac gcatgtaaca ttatactgaa aaccttgctt gagaaggttt tgggacgctc  1680
gaaggcttta atttgcaagc tgagatctaa catccaaaga cgaaaggttg aatgaaacct  1740
ttttgccatc cgacatccac aggtccattc tcacacataa gtgccaaacg caacaggagg  1800
ggatacacta gcagcagacc gttgcaaacg caggacctcc actcctcttc tcctcaacac  1860
ccacttttgc catcgaaaaa ccagcccagt tattgggctt gattggagct cgctcattcc  1920
aattccttct attaggctac taacaccatg actttattag cctgtctatc ctggcccccc  1980
tggcgaggtt catgtttgtt tatttccgaa tgcaacaagc tccgcattac acccgaacat  2040
cactccagat gagggctttc tgagtgtggg gtcaaatagt ttcatgttcc ccaaatggcc  2100
caaaactgac agtttaaacg ctgtcttgga acctaatatg acaaaagcgt gatctcatcc  2160
aagatgaact aagtttggtt cgttgaaatg ctaacggcca gttggtcaaa aagaaacttc  2220
caaaagtcgg cataccgttt gtcttgtttg gtattgattg acgaatgctc aaaaataatc  2280
tcattaatgc ttagcgcagt ctctctatcg cttctgaacc ccggtgcacc tgtgccgaaa  2340
cgcaaatggg gaaacacccg ctttttggat gattatgcat tgtctccaca ttgtatgctt  2400
ccaagattct ggtgggaata ctgctgatag cctaacgttc atgatcaaaa tttaactgtt  2460
ctaaccccta cttgacagca atatataaac agaaggaagc tgccctgtct taaacctttt  2520
tttttatcat cattattagc ttactttcat aattgcgact ggttccaatt gacaagcttt  2580
tgattttaac gacttttaac gacaacttga gaagatcaaa aaacaactaa ttattcgaaa  2640
cggaattcaa aaaatgcgac agttctccat cgttgccctc ttcgctactg gcgctctcgc  2700
cgctccagtc aacactacaa cagaagatga aacggcacaa attccggctg aagctgtcat  2760
cggttactca gatttagaag gggatttcga tgttgctgtt ttgccatttt ccgccagcat  2820
tgctgctaaa gaagaagggg tatctctcga gaaaagagag gctgaagcta acggcccgga  2880
aaccctgtgt ggtgcggaac tggtggatgc tctgcaattc gtctgtggtg accgtggctt  2940
ctacttcaat aaaccgaccg gctatggtag ctctagtcgt cgcgcgccgc agaccggtat  3000
tgtggatgaa tgctgttttc gtagctgtga cctgcgtcgt ctggaaatgt attgtgcccc  3060
gctgaaaccg gcgaaatcgg cgtgagcatg ccaaggcctc aggtaccggc cggccattta  3120
aatacaggcc ccttttcctt tgtcgatatc atgtaattag ttatgtcacg cttacattca  3180
cgccctcctc ccacatccgc tctaaccgaa aaggaaggag ttagacaacc tgaagtctag  3240
gtccctattt attttttttta atagttatgt tagtattaag aacgttattt atatttcaaa  3300
tttttctttt ttttctgtac aaacgcgtgt acgcatgtaa cattatactg aaaaccttgc  3360
ttgagaaggt tttgggacgc tcgaaggctt taatttgcaa gctgagatct aacatccaaa  3420
gacgaaaggt tgaatgaaac ctttttgcca tccgacatcc acaggtccat tctcacacat  3480
aagtgccaaa cgcaacagga ggggatacac tagcagcaga ccgttgcaaa cgcaggacct  3540
ccactcctct tctcctcaac acccactttt gccatcgaaa aaccagccca gttattgggc  3600
```

-continued

```
ttgattggag ctcgctcatt ccaattcctt ctattaggct actaacacca tgactttatt  3660
agcctgtcta tcctggcccc cctggcgagg ttcatgtttg tttatttccg aatgcaacaa  3720
gctccgcatt acacccgaac atcactccag atgagggctt tctgagtgtg gggtcaaata  3780
gtttcatgtt ccccaaatgg cccaaaactg acagtttaaa cgctgtcttg gaacctaata  3840
tgacaaaagc gtgatctcat ccaagatgaa ctaagtttgg ttcgttgaaa tgctaacggc  3900
cagttggtca aaaagaaact tccaaaagtc ggcataccgt ttgtcttgtt tggtattgat  3960
tgacgaatgc tcaaaaataa tctcattaat gcttagcgca gtctctctat cgcttctgaa  4020
ccccggtgca cctgtgccga aacgcaaatg gggaaacacc cgctttttgg atgattatgc  4080
attgtctcca cattgtatgc ttccaagatt ctggtgggaa tactgctgat agcctaacgt  4140
tcatgatcaa aatttaactg ttctaacccc tacttgacag caatatataa acagaaggaa  4200
gctgccctgt cttaaacctt ttttttatc atcattatta gcttactttc ataattgcga  4260
ctggttccaa ttgacaagct tttgatttta acgactttta acgacaactt gagaagatca  4320
aaaaacaact aattattcga aacggaattc aaaaaatgcg acagttctcc atcgttgccc  4380
tcttcgctac tggcgctctc gccgctccag tcaacactac aacagaagat gaaacggcac  4440
aaattccggc tgaagctgtc atcggttact cagatttaga aggggatttc gatgttgctg  4500
ttttgccatt ttccgccagc attgctgcta aagaagaagg ggtatctctc gagaaaagag  4560
aggctgaagc taacggcccg gaaaccctgt gtggtgcgga actggtggat gctctgcaat  4620
tcgtctgtgg tgaccgtggc ttctacttca ataaaccgac cggctatggt agctctagtc  4680
gtcgcgcgcc gcagaccggt attgtggatg aatgctgttt tcgtagctgt gacctgcgtc  4740
gtctggaaat gtattgtgcc ccgctgaaac cggcgaaatc ggcgtgagca tgccaaggcc  4800
tcaggtaccg gccggccatt taaatacagg ccccttttcc tttgtcgata tcatgtaatt  4860
agttatgtca cgcttacatt cacgccctcc tcccacatcc gctctaaccg aaaaggaagg  4920
agttagacaa cctgaagtct aggtccctat ttattttttt taatagttat gttagtatta  4980
agaacgttat ttatatttca aatttttctt ttttttctgt acaaacgcgt gtacgcatgt  5040
aacattatac tgaaaacctt gcttgagaag gttttgggac gctcgaaggc tttaatttgc  5100
aagctgagat ctaacatcca aagacgaaag gttgaatgaa accttttgc catccgacat  5160
ccacaggtcc attctcacac ataagtgcca aacgcaacag gaggggatac actagcagca  5220
gaccgttgca aacgcaggac ctccactcct cttctcctca acacccactt ttgccatcga  5280
aaaaccagcc cagttattgg gcttgattgg agctcgctca ttccaattcc ttctattagg  5340
ctactaacac catgacttta ttagcctgtc tatcctggcc cccctggcga ggttcatgtt  5400
tgtttatttc cgaatgcaac aagctccgca ttacacccga acatcactcc agatgagggc  5460
tttctgagtg tggggtcaaa tagtttcatg ttccccaaat ggcccaaaac tgacagttta  5520
aacgctgtct tggaacctaa tatgacaaaa gcgtgatctc atccaagatg aactaagttt  5580
ggttcgttga aatgctaacg gccagttggt caaaaagaaa cttccaaaag tcggcatacc  5640
gtttgtcttg tttggtattg attgacgaat gctcaaaaat aatctcatta atgcttagcg  5700
cagtctctct atcgcttctg aaccccggtg cacctgtgcc gaaacgcaaa tggggaaaca  5760
cccgcttttt ggatgattat gcattgtctc cacattgtat gcttccaaga ttctggtggg  5820
aatactgctg atagcctaac gttcatgatc aaaatttaac tgttctaacc cctacttgac  5880
agcaatatat aaacagaagg aagctgccct gtcttaaacc ttttttttta tcatcattat  5940
tagcttactt tcataattgc gactggttcc aattgacaag cttttgattt taacgacttt  6000
taacgacaac ttgagaagat caaaaaacaa ctaattattc gaaacggaat tcaaaaaatg  6060
cgacagttct ccatcgttgc cctcttcgct actggcgctc tcgccgctcc agtcaacact  6120
acaacagaag atgaaacggc acaaattccg gctgaagctg tcatcggtta ctcagattta  6180
gaaggggatt tcgatgttgc tgttttgcca ttttccgcca gcattgctgc taaagaagaa  6240
ggggtatctc tcgagaaaag agaggctgaa gctaacggcc cggaaaccct gtgtggtgcg  6300
gaactggtgg atgctctgca attcgtctgt ggtgaccgtg gcttctactt caataaaccg  6360
accggctatg gtagctctag tcgtcgcgcg ccgcagaccg gtattgtgga tgaatgctgt  6420
tttcgtagct gtgacctgcg tcgtctggaa atgtattgtg ccccgctgaa accggcgaaa  6480
tcggcgtgag catgccaagg cctcaggtac cggccggcca tttaaataca ggcccctttt  6540
cctttgtcga tatcatgtaa ttagttatgt cacgcttaca ttcacgccct cctcccacat  6600
ccgctctaac cgaaaaggaa ggagttagac aacctgaagt ctaggtccct atttattttt  6660
tttaatagtt atgttagtat taagaacgtt atttatattt caaatttttc ttttttttct  6720
gtacaaacgc gtgtacgcat gtaacattat actgaaaacc ttgcttgaga aggttttggg  6780
acgctcgaag gctttaattt gcaagctgag atctaacatc caaagacgaa aggttgaatg  6840
aaaccttttt gccatccgac atccacaggt ccattctcac acataagtgc caaacgcaac  6900
aggaggggat acactagcag cagaccgttg caaacgcagg acctccactc ctcttctcct  6960
caacacccac ttttgccatc gaaaaaccag cccagttatt gggcttgatt ggagctcgct  7020
cattccaatt ccttctatta ggctactaac accatgactt tattagcctg tctatcctgg  7080
cccccctggc gaggttcatg tttgtttatt tccgaatgca acaagctccg cattacaccc  7140
gaacatcact ccagatgagg gctttctgag tgtggggtca aatagtttca tgttccccaa  7200
atggcccaaa actgacagtt taaacgctgt cttggaacct aatatgacaa aagcgtgatc  7260
tcatccaaga tgaactaagt ttggttcgtt gaaatgctaa cggccagttg gtcaaaaaga  7320
aacttccaaa agtcggcata ccgtttgtct tgtttggtat tgattgacga atgctcaaaa  7380
ataatctcat taatgcttag cgcagtctct ctatcgcttc tgaaccccgg tgcacctgtg  7440
ccgaaacgca aatggggaaa cacccgcttt ttggatgatt atgcattgtc tccacattgt  7500
atgcttccaa gattctggtg ggaatactgc tgatagccta acgttcatga tcaaaattta  7560
actgttctaa cccctacttg acagcaatat ataaacagaa ggaagctgcc ctgtcttaaa  7620
cctttttttt tatcatcatt attagcttac tttcataatt gcgactggtt ccaattgaca  7680
agcttttgat tttaacgact tttaacgaca acttgagaag atcaaaaaac aactaattat  7740
tcgaaacgga attcaaaaaa tgcgacagtt ctccatcgtt gccctcttcg ctactggcgc  7800
tctcgccgct ccagtcaaca ctacaacaga agatgaaacg gcacaaattc cggctgaagc  7860
tgtcatcggt tactcagatt tagaagggga tttcgatgtt gctgttttgc cattttccgc  7920
cagcattgct gctaaagaag aaggggtatc tctcgagaaa agagaggctg aagctaacgg  7980
cccggaaacc ctgtgtggtg cggaactggt ggatgctctg caattcgtct gtggtgaccg  8040
tggcttctac ttcaataaac cgaccggcta tggtagctct agtcgtcgcg cgccgcagac  8100
cggtattgtg gatgaatgct gttttcgtag ctgtgacctg cgtcgtctgg aaatgtattg  8160
tgccccgctg aaaccggcga aatcggcgtg agcatgccaa ggcctcaggt accggccggc  8220
catttaaata caggcccctt ttcctttgtc gatatcatgt aattagttat gtcacgctta  8280
cattcacgcc ctcctcccac atccgctcta accgaaaagg aaggagttag acaacctgaa  8340
```

```
gtctaggtcc ctatttattt tttttaatag ttatgttagt attaagaacg ttatttatat  8400
ttcaaatttt tctttttttt ctgtacaaac gcgtgtacgc atgtaacatt atactgaaaa  8460
ccttgcttga gaaggttttg ggacgctcga aggctttaat ttgcaagctg agatctaaca  8520
tccaaagacg aaaggttgaa tgaaaccttt ttgccatccg acatccacag gtccattctc  8580
acacataagt gccaaacgca acaggagggg atacactagc agcagaccgt tgcaaacgca  8640
ggacctccac tcctcttctc ctcaacaccc actttttgcca tcgaaaaacc agcccagtta  8700
ttgggcttga ttggagctcg ctcattccaa ttccttctat taggctacta acaccatgac  8760
tttattagcc tgtctatcct ggcccccctg gcgaggttca tgtttgttta tttccgaatg  8820
caacaagctc cgcattacac ccgaacatca ctccagatga gggctttctg agtgtggggt  8880
caaatagttt catgttcccc aaatggccca aaactgacag tttaaacgct gtcttggaac  8940
ctaatatgac aaaagcgtga tctcatccaa gatgaactaa gtttggttcg ttgaaatgct  9000
aacggccagt tggtcaaaaa gaaacttcca aaagtcggca taccgtttgt cttgtttggt  9060
attgattgac gaatgctcaa aaataatctc attaatgctt agcgcagtct ctctatcgct  9120
tctgaacccc ggtgcacctg tgccgaaacg caaatgggga aacacccgct ttttggatga  9180
ttatgcattg tctccacatt gtatgcttcc aagattctgg tgggaatact gctgatagcc  9240
taacgttcat gatcaaaatt taactgttct aacccctact tgacagcaat atataaacag  9300
aaggaagctg ccctgtctta aaccttttt tttatcatca ttattagctt actttcataa  9360
ttgcgactgg ttccaattga caagcttttg attttaacga cttttaacga caacttgaga  9420
agatcaaaaa acaactaatt attcgaaacg gaattcaaaa aatgcgacag ttctccatcg  9480
ttgccctctt cgctactggc gctctcgccg ctccagtcaa cactacaaca gaagatgaaa  9540
cggcacaaat tccggctgaa gctgtcatcg gttactcaga tttagaaggg gatttcgatg  9600
ttgctgtttt gccattttcc gccagcattg ctgctaaaga agaaggggta tctctcgaga  9660
aaagagaggc tgaagctaac ggcccggaaa ccctgtgtgg tgcggaactg gtggatgctc  9720
tgcaattcgt ctgtggtgac cgtggcttct acttcaataa accgaccggc tatggtagct  9780
ctagtcgtcg cgcgccgcag accggtattg tggatgaatg ctgttttcgt agctgtgacc  9840
tgcgtcgtct ggaaatgtat tgtgccccgc tgaaaccggc gaaatcggcg tgagcatgcc  9900
aaggcctcag gtaccggccg gccatttaaa tacaggcccc ttttcctttg tcgatatcat  9960
gtaattagtt atgtcacgct tacattcacg ccctcctccc acatccgctc taaccgaaaa  10020
ggaaggagtt agacaacctg aagtctaggt ccctatttat ttttttaat agttatgtta  10080
gtattaagaa cgttatttat atttcaaatt tttctttttt ttctgtacaa acgcgtgtac  10140
gcatgtaaca ttatactgaa aaccttgctt gagaaggttt tgggacgctc gaaggcttta  10200
atttgcaagc tggatccgcg gccgccttcc aaactctcat ggattctcag gtaataggta  10260
ttctaggagg aggccagcta ggccgaatga ttgttgaggc cgctagcagg ctcaatatca  10320
agaccgtgat tcttgatgat ggtttttcac ctgctaagca cattaatgct gcgcaagacc  10380
acatcgacgg atcattcaaa gatgaggagg ctatcgccaa gttagctgcc aaatgtgatg  10440
ttctcactgt agagattgag catgtcaaca cagatgctct aaagagagtt caagacagaa  10500
ctggaatcaa gatatatcct ttaccagaga caatcgaact aatcaaggat aagtacttgc  10560
aaaaggaaca tttgatcaag cacaacattt cggtgacaaa gtctcagggt atagaatcta  10620
atgaaaaggc gctgcttttg tttggagaag agaatggatt tccatatctg ttgaagtccc  10680
ggactatggc ttatgatgga agaggcaatt ttgtagtgga gtctaaagag gacatcagta  10740
aggcattaga gttcttgaaa gatcgtccat tgtatgccga gaagtttgct ccttttgtta  10800
aagaattagc ggtaatggtt gtgagatcac tggaaggcga agtattctcc tacccaaccg  10860
tagaaactgt gcacaaggac aatatctgtc atattgtgta tgctccggcc agagttaatg  10920
acaccatcca aaagaaagct caaatattag ctgaaaacac tgtgaagact ttcccaggcg  10980
ctggaatctt cggagttgag atgttcctat tgtctgatgg agaacttctt gtaaatgaga  11040
ttgctccaag gccccacaat tctggtcact atacaatcga tgcatgtgta acatctcagt  11100
tcgaagcaca tgtaagagcc ataactggtc tgccaatgcc actagatttc accaaactat  11160
ctacttccaa caccaacgct attatgctca atgttttggg tgctgaaaaa tctcacgggg  11220
aattagagtt ttgtagaaga gccttagaaa caccggtgc ttctgtatat ctgtacggaa  11280
agaccacccg attggctcgt aagatgggtc atatcaacat aataggatct tccatgttgg  11340
aagcagaaca aaagttagag tacattctag aagaatcaac ccacttacca tccagtactg  11400
tatcagctga cactaaaccg ttggttggag ttatcatggg ttcagactct gatctacctg  11460
tgatttcgaa aggttgcgat attttaaaac agtttggtgt tccattcgaa gttactattg  11520
tctctgctca tagaacacca cagagaatga ccagatatgc ctttgaagcc gctagtagag  11580
gtatcaaggc tatcattgca ggtgctggtg gtgctgctca tcttccagga atggttgctg  11640
ccatgactcc gttgccagtc attggtgttc ctgtcaaggg ctctacgttg gatggtgtag  11700
actcgctaca ctcgattgtc caaatgccta gaggtgttcc tgtggctacg gttgctatca  11760
acaacgccac caatgccgct ctgttggcca tcaggatttt aggtacaatt gaccacaaat  11820
ggcaaaagga aatgtccaag tatatgaatg caatggagac cgaagtgttg gggaaggcat  11880
ccaacttgga atctgaaggg tatgaatcct atttgaagaa tcgtctttga atttagtatt  11940
gtttttaat agatgtatat ataatagtac acgtaactta tctattccat tcataatttt  12000
attttaaagg ttcggtagaa atttgtcctc caaaaagttg gttagagcct ggcagttttg  12060
ataggcatta ttatagattg ggtaatattt accctgcacc tggaggaact ttgcaaagag  12120
cctcatgtgc ggcgcgccag gccataatgg ccaaacggtt tctcaattac tatatactac  12180
taaccattta cctgtagcgt atttcttttc cctcttcgcg aaagctcaag ggcatcttct  12240
tgactcatga aaaatatctg gatttcttct gacagatcat caccccttgag cccaactctc  12300
tagcctatga gtgtaagtga tagtcatctt gcaacagatt attttggaac gcaactaaca  12360
aagcagatac acccttcagc agaatccttt ctggatattg tgaagaatga tcgccaaagt  12420
cacagtcctg agacagttcc taatctttac cccatttaca agttcatcca atcagacttc  12480
ttaacgcctc atctggctta tatcaagctt accaacagtt cagaaactcc cagtccaagt  12540
ttcttgcttg aaagtgcgaa gaatggtgac accgttgaca ggtacacctt tatgggacat  12600
tcccccagaa aaataatcaa gactgggcct ttagagggtg ctgaagttga ccccttggtg  12660
cttctggaaa aagaactgaa gggcaccaga caagcgcaac ttcctggtat tcctcgtcta  12720
agtggtggtg ccataggata catctcgtac gattgtatta agtactttga accaaaaact  12780
gaaagaaaac tgaaagatgt tttgcaactt ccggaagcag ctttgatgtt gttcgacacg  12840
atcgtggctt ttgacaatgt ttatcaaaga ttccaggtaa ttggaaacgt ttctctatcc  12900
gttgatgact cggacgaagc tattcttgag aaatattata agacaagaga agaagtggaa  12960
aagatcagta aagtggtatt tgacaataaa actgttccct actatgaaca gaaagatatt  13020
attcaaggcc aaacgttcac ctctaatatt ggtcaggaag ggtatgaaaa ccatgttcgc  13080
```

```
aagctgaaag aacatattct gaaaggagac atcttccaag ctgttccctc tcaaagggta  13140
gccaggccga cctcattgca ccctttcaac atctatcgtc atttgagaac tgtcaatcct  13200
tctccataca tgttctatat tgactatcta gacttccaag ttgttggtgc ttcacctgaa  13260
ttactagtta aatccgacaa caacaacaaa atcatcacac atcctattgc tggaactctt  13320
cccagaggta aaactatcga agaggacgac aattatgcta agcaattgaa gtcgtctttg  13380
aaagacaggg ccgagcacgt catgctggta gatttggcca gaaatgatat taaccgtgtg  13440
tgtgagccca ccagtaccac ggttgatcgt ttattgactg tggagagatt ttctcatgtg  13500
atgcatcttg tgtcagaagt cagtggaaca ttgagaccaa acaagactcg cttcgatgct  13560
ttcagatcca ttttcccagc aggaaccgtc tccggtgctc cgaaggtaag agcaatgcaa  13620
ctcataggag aattggaagg agaaaagaga ggtgtttatg cgggggccgt aggacactgg  13680
tcgtacgatg gaaaatcgat ggacacatgt attgccttaa gaacaatggt cgtcaaggac  13740
ggtgtcgctt accttcaagc cggaggtgga attgtctacg attctgaccc ctatgacgag  13800
tacatcgaaa ccatgaacaa aatgagatcc aacaataaca ccatcttgga ggctgagaaa  13860
atctggaccg ataggttggc cagagacgag aatcaaagtg aatccgaaga aaacgatcaa  13920
tgaacggagg acgtaagtag gaatttatgg tttggccata atggcctagc ttggcgtaat  13980
catggtcata gctgtttcct gtgtgaaatt gttatccgct cacaattcca cacaacatac  14040
gagccggaag cataaagtgt aaagcctggg gtgcctaatg agtgagctaa ctcacattaa  14100
ttgcgttgcg ctcactgccc gctttccagt cgggaaacct gtcgtgccag ctgcattaat  14160
gaatcggcca acgcgcgggg agaggcggtt tgcgtattgg gcgctcttcc gcttcctcgc  14220
tcactgactc gctgcgctcg gtcgttcggc tgcggcgagc ggtatcagct cactcaaagg  14280
cggtaatacg gttatccaca gaatcagggg ataacgcagg aaagaacatg tgagcaaaag  14340
gccagcaaaa ggccaggaac cgtaaaaagg ccgcgttgct ggcgtttttc cataggctcc  14400
gcccccctga cgagcatcac aaaaatcgac gctcaagtca gaggtggcga aacccgacag  14460
gactataaag ataccaggcg tttccccctg gaagctccct cgtgcgctct cctgttccga  14520
ccctgccgct taccggatac ctgtccgcct ttctcccttc gggaagcgtg gcgctttctc  14580
atagctcacg ctgtaggtat ctcagttcgg tgtaggtcgt tcgctccaag ctgggctgtg  14640
tgcacgaacc ccccgttcag cccgaccgct gcgccttatc cggtaactat cgtcttgagt  14700
ccaacccggt aagacacgac ttatcgccac tggcagcagc cactggtaac aggattagca  14760
gagcgaggta tgtaggcggt gctacagagt tcttgaagtg gtggcctaac tacggctaca  14820
ctagaaggac agtatttggt atctgcgctc tgctgaagcc agttaccttc ggaaaaagag  14880
ttggtagctc ttgatccggc aaacaaacca ccgctggtag cggtggtttt tttgtttgca  14940
agcagcagat tacgcgcaga aaaaaaggat ctcaagaaga tcctttgatc ttttctacgg  15000
ggtctgacgc tcagtggaac gaaaactcac gttaagggat tttggtcatg agattatcaa  15060
aaaggatctt cacctagatc cttttaaatt aaaaatgaag ttttaaatca atctaaagta  15120
tatatgagta aacttggtct gacagttacc aatgcttaat cagtgaggca cctatctcag  15180
cgatctgtct atttcgttca tccatagttg cctgactccc cgtcgtgtag ataactacga  15240
tacgggaggg cttaccatct ggccccagtg ctgcaatgat accgcgagac ccacgctcac  15300
cggctccaga tttatcagca ataaaccagc cagccggaag ggccgagcgc agaagtggtc  15360
ctgcaacttt atccgcctcc atccagtcta ttaattgttg ccgggaagct agagtaagta  15420
gttcgccagt taatagtttg cgcaacgttg ttgccattgc tacaggcatc gtggtgtcac  15480
gctcgtcgtt tggtatggct tcattcagct ccggttccca acgatcaagg cgagttacat  15540
gatcccccat gttgtgcaaa aaagcggtta gctccttcgg tcctccgatc gttgtcagaa  15600
gtaagttggc cgcagtgtta tcactcatgg ttatggcagc actgcataat tctcttactg  15660
tcatgccatc cgtaagatgc ttttctgtga ctggtgagta ctcaaccaag tcattctgag  15720
aatagtgtat gcggcgaccg agttgctctt gcccggcgtc aatacgggat aataccgcgc  15780
cacatagcag aactttaaaa gtgctcatca ttggaaaacg ttcttcgggg cgaaaactct  15840
caaggatctt accgctgttg agatccagtt cgatgtaacc cactcgtgca cccaactgat  15900
cttcagcatc ttttactttc accagcgttt ctgggtgagc aaaaacagga aggcaaaatg  15960
ccgcaaaaaa gggaataagg gcgacacgga aatgttgaat actcatactc ttcctttttc  16020
aatattattg aagcatttat cagggttatt gtctcatgag cggatacata tttgaatgta  16080
tttagaaaaa taaacaaata ggggttccgc gcacatttcc ccgaaaagtg ccacctgacg  16140
tctaagaaac cattattatc atgacattaa cctataaaaa taggcgtatc acgaggccct  16200
ttcgtctcgc gcgtttcggt gatgacggtg aaaacctctg acacatgcag ctcccggaga  16260
cggtcacagc ttgtctgtaa gcggatgccg ggagcagaca agcccgtcag ggcgcgtcag  16320
cgggtgttgg cgggtgtcgg ggctggctta actatgcggc atcagagcag attgtactga  16380
gagtgcacca tatgcggtgt gaaataccgc acagatgcgt aaggagaaaa taccgcatca  16440
ggcgccattc gccattcagg ctgcgcaact gttgggaagg gcgatcggtg cgggcctctt  16500
cgctattacg ccagctggcg aaagggggat gtgctgcaag gcgattaagt tgggtaacgc  16560
cagggttttc ccagtcacga cgttgtaaaa cgacggccag tgaattg                16607
```

```
SEQ ID NO: 13          moltype = AA  length = 102
FEATURE                Location/Qualifiers
REGION                 1..102
                       note = Ophiostoma novo-ulmi - cu signal sequence
source                 1..102
                       mol_type = protein
                       organism = synthetic construct
SEQUENCE: 13
MQFSIATIAL FLSSAMAAAA PYSGNSNSDS YDPCTGLLQK SPQCCNTDIL GVANLDCHGP  60
PSVPTSPSQF QASCVADGGR SARCCTLSLL GLALVCTDPV GI                     102

SEQ ID NO: 14          moltype = AA  length = 100
FEATURE                Location/Qualifiers
REGION                 1..100
                       note = Trichoderma reesei - hfb1 signal sequence
source                 1..100
                       mol_type = protein
                       organism = synthetic construct
```

```
SEQUENCE: 14
MKFFAIAALF AAAAVAAAQP LEDRSNGNGN VCPPGLFSNP QCCATQVLGL IGLDCKKVPS  60
QNVYDGTDFR NVCAKTGAQP LCCVAPVAGQ ALLCQTAVGA                        100

SEQ ID NO: 15          moltype = AA  length = 89
FEATURE                Location/Qualifiers
REGION                 1..89
                       note = Trichoderma reesei - hfb2 signal sequence
source                 1..89
                       mol_type = protein
                       organism = synthetic construct
SEQUENCE: 15
MQFFAVALFA TSALAAAAVC PTGLFSNPLC CATNVLDLIG VDCKKTPTIA VDTGAIFQAH  60
CASKGSKPLC CVAPVADQAL LCQKAIGTF                                    89

SEQ ID NO: 16          moltype = AA  length = 90
FEATURE                Location/Qualifiers
REGION                 1..90
                       note = Trichoderma viride - srh1 signal sequence
source                 1..90
                       mol_type = protein
                       organism = synthetic construct
SEQUENCE: 16
MQFSIVALFA TGALAAASVS VCPNGLYSNP RCCGANVLGV AALDCHTPRV DVLTGPIFQA  60
VCAAEGGQPL CCVVPVAGQD LLCEEAQGTF                                   90

SEQ ID NO: 17          moltype = AA  length = 115
FEATURE                Location/Qualifiers
REGION                 1..115
                       note = Pleurotus ostreatus - fbh1 signal sequence
source                 1..115
                       mol_type = protein
                       organism = synthetic construct
SEQUENCE: 17
MFSIRIATVV LAASALLAAA AASPITNTET PVNQCGSGSI QCCESVQSAS AAQAAGILGP  60
LDILTNLQGL VASHCSPLAA VGVSGTSCSS QTVCCKDVSK SGLVNLGCSP INLNL       115

SEQ ID NO: 18          moltype = AA  length = 91
FEATURE                Location/Qualifiers
REGION                 1..91
                       note = Cladosporium fulvum - hcf5 signal sequence
source                 1..91
                       mol_type = protein
                       organism = synthetic construct
SEQUENCE: 18
MQFLVLALAS LAAAAAAPSI KLRAPSDVCP ALDTPLCCQA DVLGVLDLTC EAPSDDTSVS  60
NFEAACAATT GLTARCCTLP LLGEALLCTT P                                  91

SEQ ID NO: 19          moltype = AA  length = 138
FEATURE                Location/Qualifiers
REGION                 1..138
                       note = Aspergillus nidulans FGSC A4 - dewA signal sequence
source                 1..138
                       mol_type = protein
                       organism = synthetic construct
SEQUENCE: 19
MRFIVSLLAF TAAATATAAA LPASAAKNKA LATSAAFAKQ AEGTCNVGSI ACCNSPAETN  60
NDSLLSGLLG AGLLNGLSGN TGSACAKASL IDQLGLLALV DHTEEGPVCK KNIVACCPEG  120
TTNCVVAVDN AGAGTKAE                                                138

SEQ ID NO: 20          moltype = AA  length = 120
FEATURE                Location/Qualifiers
REGION                 1..120
                       note = Endothia parasitica cryparin - crp signal sequence
source                 1..120
                       mol_type = protein
                       organism = synthetic construct
SEQUENCE: 20
MQFSIIAISF LASLAMAAAS PAKRGGGGGG SGSGSGSGSG SGSGGGSTTY TACSSTLYSE  60
AQCCATDVLG VADLDCETVP ETPTSASSFE SICATSGRDA KCCTIPLLGQ ALLCQDPVGL  120

SEQ ID NO: 21          moltype = AA  length = 104
FEATURE                Location/Qualifiers
REGION                 1..104
                       note = Magnaporthe grisea magnaporin - mhp1 signal sequence
source                 1..104
                       mol_type = protein
                       organism = synthetic construct
```

```
SEQUENCE: 21
MQFSTIIATI FVAATGAVAA ALPAEVQERQ VPYTPCSGLY GSAQCCATDI LGLANLDCGQ  60
PSDAPVDADN FSEICAAIGQ RARCCVLPIL DQGILCNTPA GVTP                   104

SEQ ID NO: 22          moltype = DNA  length = 62
FEATURE                Location/Qualifiers
misc_feature           1..62
                       note = CU(R) F
misc_feature           15
                       note = N is A, T, G, or C
source                 1..62
                       mol_type = other DNA
                       organism = synthetic construct
SEQUENCE: 22
atagaattca tgcgncagtt ctccattgcc accatcgccc tcttcctgtc ctccgccatg  60
gc                                                                 62

SEQ ID NO: 23          moltype = DNA  length = 43
FEATURE                Location/Qualifiers
misc_feature           1..43
                       note = CU(R)_alpha F
source                 1..43
                       mol_type = other DNA
                       organism = synthetic construct
SEQUENCE: 23
ttcctgtcct ccgccatggc ggctccagtc aacactacaa cag                    43

SEQ ID NO: 24          moltype = DNA  length = 40
FEATURE                Location/Qualifiers
misc_feature           1..40
                       note = alpha_IGF1 R
source                 1..40
                       mol_type = other DNA
                       organism = synthetic construct
SEQUENCE: 24
cacacagggt ttccgggcca gcttcagcct ctcttttctc                        40

SEQ ID NO: 25          moltype = DNA  length = 41
FEATURE                Location/Qualifiers
misc_feature           1..41
                       note = alpha_IGF1 F
source                 1..41
                       mol_type = other DNA
                       organism = synthetic construct
SEQUENCE: 25
gagaaaagag aggctgaagc tggcccggaa accctgtgtg g                      41

SEQ ID NO: 26          moltype = DNA  length = 31
FEATURE                Location/Qualifiers
misc_feature           1..31
                       note = IGF1 R
source                 1..31
                       mol_type = other DNA
                       organism = synthetic construct
SEQUENCE: 26
atagcatgct cacgccgatt tcgccggttt c                                 31

SEQ ID NO: 27          moltype = DNA  length = 66
FEATURE                Location/Qualifiers
misc_feature           1..66
                       note = HCF(R)5 F
misc_feature           18
                       note = N is A, T, G, or C
source                 1..66
                       mol_type = other DNA
                       organism = synthetic construct
SEQUENCE: 27
atagaattca tgatgcgnca attcctcgtc ctcgcccttg catcgcttgc agccgcagct  60
ccagtc                                                             66

SEQ ID NO: 28          moltype = DNA  length = 34
FEATURE                Location/Qualifiers
misc_feature           1..34
                       note = HCF5(R)_alpha F
source                 1..34
                       mol_type = other DNA
                       organism = synthetic construct
SEQUENCE: 28
cttgcagccg cagctccagt caacactaca acag                              34
```

```
SEQ ID NO: 29           moltype = DNA  length = 61
FEATURE                 Location/Qualifiers
misc_feature            1..61
                        note = MHP(R)1 F
misc_feature            15
                        note = n is A, T, G, or C
source                  1..61
                        mol_type = other DNA
                        organism = synthetic construct
SEQUENCE: 29
atagaattca tgcgncagtt ctccaccatc atcgccacca tcttcgtcgc ggccaccggt  60
g                                                                   61

SEQ ID NO: 30           moltype = DNA  length = 49
FEATURE                 Location/Qualifiers
misc_feature            1..49
                        note = MHP1(R)_alpha F
source                  1..49
                        mol_type = other DNA
                        organism = synthetic construct
SEQUENCE: 30
ttcgtcgcgg ccaccggtgc cgttgccgct ccagtcaaca ctacaacag              49

SEQ ID NO: 31           moltype = DNA  length = 62
FEATURE                 Location/Qualifiers
misc_feature            1..62
                        note = Srh(R)1 F
misc_feature            15
                        note = n is A, T, G, or C
source                  1..62
                        mol_type = other DNA
                        organism = synthetic construct
SEQUENCE: 31
atagaattca tgcgncagtt ctccatcgtt gccctcttcg ctactggcgc tctcgccgct  60
cc                                                                  62

SEQ ID NO: 32           moltype = DNA  length = 37
FEATURE                 Location/Qualifiers
misc_feature            1..37
                        note = Srh1(R)1_alpha F
source                  1..37
                        mol_type = other DNA
                        organism = synthetic construct
SEQUENCE: 32
actggcgctc tcgccgctcc agtcaacact acaacag                            37

SEQ ID NO: 33           moltype = DNA  length = 22
FEATURE                 Location/Qualifiers
misc_feature            1..22
                        note = SeqF
source                  1..22
                        mol_type = other DNA
                        organism = synthetic construct
SEQUENCE: 33
aggaagctgc cctgtcttaa ac                                            22

SEQ ID NO: 34           moltype = DNA  length = 22
FEATURE                 Location/Qualifiers
misc_feature            1..22
                        note = SeqR
source                  1..22
                        mol_type = other DNA
                        organism = synthetic construct
SEQUENCE: 34
caaattaaag ccttcgagcg tc                                            22

SEQ ID NO: 35           moltype = DNA  length = 24
FEATURE                 Location/Qualifiers
misc_feature            1..24
                        note = AOX1 F
source                  1..24
                        mol_type = other DNA
                        organism = synthetic construct
SEQUENCE: 35
gttgaatgaa accttttttgc catc                                         24

SEQ ID NO: 36           moltype = DNA  length = 22
FEATURE                 Location/Qualifiers
```

```
misc_feature            1..22
                        note = AOX1 R
source                  1..22
                        mol_type = other DNA
                        organism = synthetic construct
SEQUENCE: 36
tcatgaacgt taggctatca gc                                            22

SEQ ID NO: 37           moltype = DNA  length = 67
FEATURE                 Location/Qualifiers
misc_feature            1..67
                        note = scvSrh1
misc_feature            10
                        note = W is A or T
misc_feature            12
                        note = M is A or C
misc_feature            14
                        note = M is A or C
misc_feature            20
                        note = N is A, T, G or C
misc_feature            29
                        note = N is A, T, G, or C
misc_feature            35
                        note = N is A, T, G or C
misc_feature            38
                        note = N is A, T, G or C
misc_feature            41
                        note = N is A, T, G or C
misc_feature            47
                        note = N is A, T, G or C
source                  1..67
                        mol_type = other DNA
                        organism = synthetic construct
SEQUENCE: 37
atagaattcw amamatgcgn carttytcna thgtngcnct nttygcnact ggcgctctcg  60
ccgctcc                                                             67

SEQ ID NO: 38           moltype = DNA  length = 44
FEATURE                 Location/Qualifiers
misc_feature            1..44
                        note = In multi X F
source                  1..44
                        mol_type = other DNA
                        organism = synthetic construct
SEQUENCE: 38
ctttaatttg caagctggat ctaacatcca aagacgaaag gttg                    44

SEQ ID NO: 39           moltype = DNA  length = 21
FEATURE                 Location/Qualifiers
misc_feature            1..21
                        note = In multi X R
source                  1..21
                        mol_type = other DNA
                        organism = synthetic construct
SEQUENCE: 39
tttggaaggc ggccgcggat c                                             21

SEQ ID NO: 40           moltype = DNA  length = 45
FEATURE                 Location/Qualifiers
misc_feature            1..45
                        note = alpha F
source                  1..45
                        mol_type = other DNA
                        organism = synthetic construct
SEQUENCE: 40
tattcgaaac ggaattcatg agatttcctt caatttttac tgcag                   45

SEQ ID NO: 41           moltype = DNA  length = 40
FEATURE                 Location/Qualifiers
misc_feature            1..40
                        note = alpha_IGF1 R
source                  1..40
                        mol_type = other DNA
                        organism = synthetic construct
SEQUENCE: 41
cacacagggt ttccgggcca gcttcagcct ctcttttctc                         40

SEQ ID NO: 42           moltype = DNA  length = 41
FEATURE                 Location/Qualifiers
```

```
misc_feature          1..41
                      note = alpha_IGF1 F
source                1..41
                      mol_type = other DNA
                      organism = synthetic construct
SEQUENCE: 42
gagaaaagag aggctgaagc tggcccggaa accctgtgtg g                41

SEQ ID NO: 43         moltype = DNA  length = 31
FEATURE               Location/Qualifiers
misc_feature          1..31
                      note = IGF1 R
source                1..31
                      mol_type = other DNA
                      organism = synthetic construct
SEQUENCE: 43
atagcatgct cacgccgatt tcgccggttt c                           31

SEQ ID NO: 44         moltype = DNA  length = 20
FEATURE               Location/Qualifiers
misc_feature          1..20
                      note = IGF GR/N 2F
source                1..20
                      mol_type = other DNA
                      organism = synthetic construct
SEQUENCE: 44
ggcccggaaa ccctgtgtgg                                        20

SEQ ID NO: 45         moltype = DNA  length = 40
FEATURE               Location/Qualifiers
misc_feature          1..40
                      note = IGF N 2R
source                1..40
                      mol_type = other DNA
                      organism = synthetic construct
SEQUENCE: 45
cagggtttcc gggccgttag cttcagcctc tcttttctcg                  40

SEQ ID NO: 46         moltype = DNA  length = 43
FEATURE               Location/Qualifiers
misc_feature          1..43
                      note = InIGF GR 2R
source                1..43
                      mol_type = other DNA
                      organism = synthetic construct
SEQUENCE: 46
cagggtttcc gggccccgac cagcttcagc ctctcttttc tcg              43

SEQ ID NO: 47         moltype = AA  length = 17
FEATURE               Location/Qualifiers
REGION                1..17
                      note = Ophiostoma novo-ulmi - cu signal sequence
source                1..17
                      mol_type = protein
                      organism = synthetic construct
SEQUENCE: 47
MQFSIATIAL FLSSAMA                                           17

SEQ ID NO: 48         moltype = AA  length = 18
FEATURE               Location/Qualifiers
REGION                1..18
                      note = Ophiostoma novo-ulmi - cu(R) signal sequence
source                1..18
                      mol_type = protein
                      organism = synthetic construct
SEQUENCE: 48
MRQFSIATIA LFLSSAMA                                          18

SEQ ID NO: 49         moltype = AA  length = 19
FEATURE               Location/Qualifiers
REGION                1..19
                      note = Magnaporthe grisea magnaporin - mhp1 signal sequence
source                1..19
                      mol_type = protein
                      organism = synthetic construct
SEQUENCE: 49
MQFSTIIATI FVAATGAVA                                         19

SEQ ID NO: 50         moltype = AA  length = 20
```

```
FEATURE                Location/Qualifiers
REGION                 1..20
                       note = Magnaporthe grisea magnaporin - mhp1(R) signal
                        sequence
source                 1..20
                       mol_type = protein
                       organism = synthetic construct
SEQUENCE: 50
MRQFSTIIAT IFVAATGAVA                                              20

SEQ ID NO: 51          moltype = AA  length = 14
FEATURE                Location/Qualifiers
REGION                 1..14
                       note = Cladosporium fulvum - hcf5 signal sequence
source                 1..14
                       mol_type = protein
                       organism = synthetic construct
SEQUENCE: 51
MQFLVLALAS LAAA                                                    14

SEQ ID NO: 52          moltype = AA  length = 15
FEATURE                Location/Qualifiers
REGION                 1..15
                       note = Cladosporium fulvum - hcf5(R) signal sequence
source                 1..15
                       mol_type = protein
                       organism = synthetic construct
SEQUENCE: 52
MRQFLVLALA SLAAA                                                   15

SEQ ID NO: 53          moltype = AA  length = 15
FEATURE                Location/Qualifiers
REGION                 1..15
                       note = Trichoderma viride - srh1 signal sequence
source                 1..15
                       mol_type = protein
                       organism = synthetic construct
SEQUENCE: 53
MQFSIVALFA TGALA                                                   15

SEQ ID NO: 54          moltype = AA  length = 16
FEATURE                Location/Qualifiers
REGION                 1..16
                       note = Trichoderma viride - srh1(R) signal sequence
source                 1..16
                       mol_type = protein
                       organism = synthetic construct
SEQUENCE: 54
MRQFSIVALF ATGALA                                                  16

SEQ ID NO: 55          moltype = DNA  length = 263
FEATURE                Location/Qualifiers
misc_feature           1..263
                       note = Srh(R)1-alphapro-IGF1
misc_feature           1
                       note = W is A or T
misc_feature           3
                       note = M is A or C
misc_feature           5
                       note = M is A or C
misc_feature           11
                       note = N is A, G, C, or T
source                 1..263
                       mol_type = other DNA
                       organism = synthetic construct
SEQUENCE: 55
wamamatgcg ncagttctcc atcgttgccc tcttcgctac tggcgctctc gccgctccag  60
tcaacactac aacagaagat gaaacggcac aaattccggc tgaagctgtc atcggttact  120
cagatttaga aggggatttc gatgttgctg ttttgccatt ttccaacagc acaaataacg  180
ggttattgtt tataaatact actattgcca gcattgctgc taaagaagaa ggggtatctc  240
tcgagaaaag agaggctgaa gct                                          263

SEQ ID NO: 56          moltype = AA  length = 263
FEATURE                Location/Qualifiers
REGION                 1..263
                       note = Srh(r)1-alphapro-IGF1
```

```
VARIANT                 1
                        note = X can be W or A
VARIANT                 3
                        note = X can be M or A
VARIANT                 5
                        note = X can be M or A
VARIANT                 11
                        note = X can be N or G
VARIANT                 14
                        note = X can be G or A
VARIANT                 20
                        note = X can be C or T
VARIANT                 23
                        note = X can be C or T
VARIANT                 29
                        note = X can be C or T
VARIANT                 32
                        note = X can be C or G
source                  1..263
                        mol_type = protein
                        organism = synthetic construct
SEQUENCE: 56
XAXAXATGCG XCAXTTCTCX ATXGTTGCXC TXTTCGCTAC TGGCGCTCTC GCCGCTCCAG  60
TCAACACTAC AACAGAAGAT GAAACGGCAC AAATTCCGGC TGAAGCTGTC ATCGGTTACT  120
CAGATTTAGA AGGGGATTTC GATGTTGCTG TTTTGCCATT TTCCAACAGC ACAAATAACG  180
GGTTATTGTT TATAAATACT ACTATTGCCA GCATTGCTGC TAAAGAAGAA GGGGTATCTC  240
TCGAGAAAAG AGAGGCTGAA GCT                                          263

SEQ ID NO: 57           moltype = AA  length = 76
FEATURE                 Location/Qualifiers
REGION                  1..76
                        note = scvSrh(R)1-alphapro-GR-hIGF1
source                  1..76
                        mol_type = protein
                        organism = synthetic construct
SEQUENCE: 57
EAEAGRGPET LCGAELVDAL QFVCGDRGFY FNKPTGYGSS SRRAPQTGIV DECCFRSCDL  60
RRLEMYCAPL KPAKSA                                                  76

SEQ ID NO: 58           moltype = AA  length = 75
FEATURE                 Location/Qualifiers
REGION                  1..75
                        note = scvSrh(R)1-?pro-GR-hIGF1
source                  1..75
                        mol_type = protein
                        organism = synthetic construct
SEQUENCE: 58
AEAGRGPETL CGAELVDALQ FVCGDRGFYF NKPTGYGSSS RRAPQTGICD ECCFRSCDLR  60
RLEMYCAPLK PAKSA                                                   75

SEQ ID NO: 59           moltype = AA  length = 74
FEATURE                 Location/Qualifiers
REGION                  1..74
                        note = scvSrh(R)1-alphapro-GR-hIGF1
source                  1..74
                        mol_type = protein
                        organism = synthetic construct
SEQUENCE: 59
EAGRGPETLC GAELVDALQF VCGDRGFYFN KPTGYGSSSR RAPQTGIVDE CCFRSCDLRR  60
LEMYCAPLKP AKSA                                                    74

SEQ ID NO: 60           moltype = AA  length = 73
FEATURE                 Location/Qualifiers
REGION                  1..73
                        note = scvSrh(R)1-alphapro-GR-hIGF1
source                  1..73
                        mol_type = protein
                        organism = synthetic construct
SEQUENCE: 60
AGRGPETLCG AELVDALQFV CGDRGFYFNK PTGYGSSSRR APQTGIVDEC CFRSCDLRRL  60
EMYCAPLKPA KSA                                                     73

SEQ ID NO: 61           moltype = AA  length = 72
FEATURE                 Location/Qualifiers
REGION                  1..72
                        note = scvSrh(R)1-alphapro-GR-hIGF1
source                  1..72
                        mol_type = protein
                        organism = synthetic construct
```

```
SEQUENCE: 61
GRGPETLVGA ELVDALQFVC GDRGFYFNKP TGYGSSSRRA PQTGIVDECC FRSCDLRRLW  60
MYCAPLKPAK SA                                                      72

SEQ ID NO: 62           moltype = AA  length = 71
FEATURE                 Location/Qualifiers
REGION                  1..71
                        note = scvSrh(R)1-alphapro-GR-hIGF1
source                  1..71
                        mol_type = protein
                        organism = synthetic construct
SEQUENCE: 62
RGPETLCGAE LVDALQFVCG DRGFYFNKPT GYGSSSRRAP QTGIVDECCF RSCDLRRLEM  60
YCAPLKPAKS A                                                       71

SEQ ID NO: 63           moltype = AA  length = 70
FEATURE                 Location/Qualifiers
REGION                  1..70
                        note = scvSrh(R)1-alphapro-GR-hIGF1
source                  1..70
                        mol_type = protein
                        organism = synthetic construct
SEQUENCE: 63
GPETLCGAEL VDALQFVCGD RGFYFNKPTG YGSSSRRAPQ TGIVDECCFR SCDLRRLEMY  60
CAPLKPAKSA                                                         70

SEQ ID NO: 64           moltype = AA  length = 75
FEATURE                 Location/Qualifiers
REGION                  1..75
                        note = scvSrh(R)1-alphapro-N-hIGF1
source                  1..75
                        mol_type = protein
                        organism = synthetic construct
SEQUENCE: 64
EAEANGPETL CGAELVDALQ FVCGDRGFYF NKPTGYGSSS RRAPQTGIVD ECCFRSCDLR  60
RLEMYCAPLK PAKSA                                                   75

SEQ ID NO: 65           moltype = AA  length = 74
FEATURE                 Location/Qualifiers
REGION                  1..74
                        note = scvSrh(R)1-alphapro-N-hIGF1
source                  1..74
                        mol_type = protein
                        organism = synthetic construct
SEQUENCE: 65
AEANGPETLC GAELVDALQF VCGDRGFYFN KPTGYGSSSR RAPQTGIVDE CCFRSCDLRR  60
LEMYCAPLKP AKSA                                                    74

SEQ ID NO: 66           moltype = AA  length = 73
FEATURE                 Location/Qualifiers
REGION                  1..73
                        note = scvSrh(R)1-alphapro-N-hIGF1
source                  1..73
                        mol_type = protein
                        organism = synthetic construct
SEQUENCE: 66
EANGPETLCG AELVDALQFV CGDRGFYFNK PTGYGSSSRR APQTGIVDEC CFRSCDLRRL  60
EMYCAPLKPA KSA                                                     73

SEQ ID NO: 67           moltype = AA  length = 72
FEATURE                 Location/Qualifiers
REGION                  1..72
                        note = scvSrh(R)1-alphapro-N-hIGF1
source                  1..72
                        mol_type = protein
                        organism = synthetic construct
SEQUENCE: 67
ANGPETLCGA ELVDALQFVC GDRGFYFNKP TGYGSSSRRA PQTGIVDECC FRSCDLRRLE  60
MYCAPLKPAK SA                                                      72

SEQ ID NO: 68           moltype = AA  length = 71
FEATURE                 Location/Qualifiers
REGION                  1..71
                        note = scvSrh(R)1-alphapro-N-hIGF1
source                  1..71
                        mol_type = protein
                        organism = synthetic construct
```

-continued

```
SEQUENCE: 68
NGPETLCGAE LVDALQFVCG DRGFYFNKPT GYGSSSRRAP QTGIVDECCF RSCDLRRLEM  60
YCAPLKPAKS A                                                       71

SEQ ID NO: 69           moltype = AA  length = 70
FEATURE                 Location/Qualifiers
REGION                  1..70
                        note = scvSrh(R)1-alphapro-N-hIGF1
source                  1..70
                        mol_type = protein
                        organism = synthetic construct
SEQUENCE: 69
GPETLCGAEL VDALQFVCGD RGFYFNKPTG YGSSSRRAPQ TGIVDECCFR SCDLRRLEMY  60
CAPLKPAKSA                                                         70

SEQ ID NO: 70           moltype = AA  length = 69
FEATURE                 Location/Qualifiers
REGION                  1..69
                        note = scvSrh(R)1-alphapro-N-hIGF1
source                  1..69
                        mol_type = protein
                        organism = synthetic construct
SEQUENCE: 70
PETLCGAELV DALQFVCGDR GFYFNKPTGY GSSSRRAPQT GIVDECCFRS CDLRRLEMYC  60
APLKPAKSA                                                          69
```

The invention claimed is:

1. A hybrid signal sequence consisting of an amino acid sequence for secretory expression of a human insulin-like growth factor-1 (hIGF1) and obtained by fusing a signal sequence of an α-mating factor to the C-terminus of a signal sequence of hydrophobin Srhl containing one or two or more amino acid mutations, wherein the hydrophobin Srhl is derived from *Trichoderma viride*, and the α-mating factor is derived from *Saccharomyces cerevisiae*, wherein the hybrid signal sequence is encoded by a polynucleotide which consists of the base sequence of SEO ID NO: 5.

2. The hybrid signal sequence of claim 1, wherein the amino acid mutation is obtained by inserting arginine into between methionine, the starting amino acid, and an amino acid at position 2 of the N-terminus of the signal sequence of the hydrophobin Srh1, wherein the signal sequence of the hydrophobin Srh1 consists of the amino acid sequence of SEQ ID NO: 53.

3. A recombinant expression vector comprising the polynucleotide of claim 1 and a polynucleotide encoding a human insulin-like growth factor-1 (hIGF1).

4. The recombinant expression vector of claim 3, wherein both polynucleotides are tandemly repeated 2 to 6 times.

5. The recombinant expression vector of claim 4, wherein the recombinant expression vector consists of the base sequence of SEQ ID NO: 6.

6. A non-human transformant transformed through homologous recombination by introducing the recombinant expression vector of claim 3.

7. The transformant of claim 6, wherein the non-human transformant is *Komagataella phaffii*.

8. A polynucleotide encoding the hybrid signal sequence of claim 2.

9. A method of producing a recombinant hIGF1, the method comprising:

preparing the recombinant expression vector of claim 3;

introducing and transforming the recombinant expression vector into a non-human transformable host to obtain a transformant;

culturing the transformant to overexpress the recombinant hIGF1;

and purifying and recovering the hIGF1.

* * * * *